US007541440B2

(12) United States Patent
Goldenberg et al.

(10) Patent No.: US 7,541,440 B2
(45) Date of Patent: Jun. 2, 2009

(54) CHIMERIC, HUMAN AND HUMANIZED ANTI-GRANULOCYTE ANTIBODIES AND METHODS OF USE

(75) Inventors: David M. Goldenberg, Mendham, NJ (US); Hans J. Hansen, Picayune, MS (US); Shui-on Leung, Shatin (HK)

(73) Assignee: Immunomedics, Inc., Morris Plains, NJ (US)

( * ) Notice: Subject to any disclaimer, the term of this patent is extended or adjusted under 35 U.S.C. 154(b) by 941 days.

(21) Appl. No.: 10/672,278

(22) Filed: Sep. 29, 2003
(Under 37 CFR 1.47)

(65) Prior Publication Data

US 2007/0183970 A1 Aug. 9, 2007

Related U.S. Application Data

(60) Provisional application No. 60/414,341, filed on Sep. 30, 2002.

(51) Int. Cl.

| | |
|---|---|
| ***C12P 21/08*** | (2006.01) |
| ***C07K 16/00*** | (2006.01) |
| ***C07K 17/00*** | (2006.01) |
| ***C07K 17/14*** | (2006.01) |
| *A61K 39/00* | (2006.01) |
| *A61K 39/395* | (2006.01) |

(52) U.S. Cl. .............. 530/387.3; 530/387.1; 530/391.1; 424/133.1; 424/141.1; 424/181.1; 424/183.1

(58) Field of Classification Search ....................... None
See application file for complete search history.

(56) References Cited

U.S. PATENT DOCUMENTS

| | | | | |
|---|---|---|---|---|
| 4,816,397 | A * | 3/1989 | Boss et al. | 435/69.6 |
| 4,816,567 | A * | 3/1989 | Cabilly et al. | 530/387.3 |
| 5,258,498 | A * | 11/1993 | Huston et al. | 530/350 |
| 5,618,920 | A * | 4/1997 | Robinson et al. | 530/387.1 |
| 5,677,427 | A | 10/1997 | Goldenberg et al. | |
| 5,994,510 | A | 11/1999 | Adair et al. | |
| 6,759,045 | B2 * | 7/2004 | Goldenberg et al. | 424/153.1 |
| 2002/0006379 | A1 * | 1/2002 | Hansen et al. | 424/1.49 |

OTHER PUBLICATIONS

Cruse, J.M., and Lewis, R.E. Illustrated Dictionary of Immunology, 1995. CRC Press, Boca Raton, Fl. p. 65.*

Becker, W., Bair, J., Behr, T., Repp, R., Streckenbach, H., Beck, H., Gramatzki, M., Winship, M.J., Goldenberg, D.M., and Wolf, F. Detection of soft-tissue infections and osteomyelitis using a technetium-99m-labeled anti-granulocyte monoclonal antibody fragment. Journal of Nuclear Medicine, 1994. vol. 35, pp. 1436-1443.*

Orlandi, R., Gussow, D.H., Jones, P.T., and Winter, G. Cloning Immunoglobulin Variable Domains for Expression by the Polymerase Chain Reaction. Proceedings of the National Academy of Sciences, 1989. vol. 86, pp. 3833-3837.*

Ward, S.E., Gussow, D., Griffiths, A.D., Jones, P.T., and Winter, G. Binding activities of a repertoire of single immunoglobulin variable domains secreted from *Escherichia coli*. Nature, 1989. vol. 341, pp. 544-546.*

Hansen, H.J., Goldenberg, D.M., Newman, E.S., Grebenau, R., and Sharkey, R.M. Characterization of second-generation monoclonal antibodies against carcinoembryonic antigen. Cancer, 1993. vol. 71, pp. 3478-3485.*

Decristoforo, C. et al., "Failure of Labelling of Anti-Granulocyte Antibody" European Journal of Nuclear Medicine, Berlin, DE, vol. 20, No. 6, Jun. 1993, pp. 565-566, XP008022454 ISSN: 0340-6997.

Sato, K., et al., "Humanization of a Mouse Anti-Human Interleukin-6 Receptor Antibody Comparing Two Methods for Selecting Human Framework Regions" Molecular Immunology, Elmsford, NY, US, vol. 31, No. 5, Apr. 1994, pp. 371-381, XP001069947 ISSN: 0161-5890.

* cited by examiner

*Primary Examiner*—David J. Blanchard
*Assistant Examiner*—Anne M. Gussow
(74) *Attorney, Agent, or Firm*—Richard A. Nakashima

(57) ABSTRACT

The present invention provides humanized, chimeric and human MN3 antibodies, fusion proteins, and fragments thereof. The antibodies, fusion proteins, and fragments thereof, as well as combinations with other suitable antibodies, are useful for the treatment and diagnosis of granulocyte related disorders and diseases, such as leukemia.

24 Claims, 10 Drawing Sheets

```
AGCATTGTGATGACCCAGACTCCACTCTCCCTGCCTGTCAGTCTTGGAGATCAAGCCTCCATCTCTTGCAGATCTAGTCAGAGCATTGTA
---------+---------+---------+---------+---------+---------+---------+---------+---------+  90
TCGTAACACTACTGGGTCTGAGGTGAGAGGGACGGACAGTCAGAACCTCTAGTTCGGAGGTAGAGAACGTCTAGATCAGTCTCGTAACAT
 1                     10                       20                  27A B  C
 S  I  V  M  T  Q  T  P  L  S  L  P  V  S  L  G  D  Q  A  S  I  S  C  R  S  S  Q  S  I  V   30

CATAGTAATGGAAACACCTATTTAGAATGGTACCTGCAGAAACCAGGCCAGTCTCCAAACCTCCTCATCTACAAAGTTTCCAACCGATTT
---------+---------+---------+---------+---------+---------+---------+---------+---------+  180
GTATCATTACCTTTGTGGATAAATCTTACCATGGACGTCTTTGGTCCGGTCAGAGGTTTGGAGGAGTAGATGTTTCAAAGGTTGGCTAAA
 D  E     30                         40                       50
 H  S  N  G  N  T  Y  L  E  W  Y  L  Q  K  P  G  Q  S  P  N  L  L  I  Y  K  V  S  N  R  F
CDR1                                                                        CDR2

TCTGGGGTCCCAGACAGGTTCAGTGGCAGTGGATCAGGGACAGATTTCACACTCAAGATCAGCAGAGTGGAGGCTGAGGATCTGGGAGTT
---------+---------+---------+---------+---------+---------+---------+---------+---------+  270
AGACCCCAGGGTCTGTCCAAGTCACCGTCACCTAGTCCCTGTCTAAAGTGTGAGTTCTAGTCGTCTCACCTCCGACTCCTAGACCCTCAA
          60                       70                       80
 S  G  V  P  D  R  F  S  G  S  G  S  G  T  D  F  T  L  K  I  S  R  V  E  A  E  D  L  G  V

TATTACTGCTTTCAAGGTTCACATGTTCCTCCGACGTTCGGTGGAGGCACCAAGCTGGAAATCAAACGGgctgatgctgcaccaactgta
---------+---------+---------+---------+---------+---------+---------+---------+---------+  339
ATAATGACGAAAGTTCCAAGTGTACAAGGAGGCTGCAAGCCACCTCCGTGGTTCGACCTTTAGTTTGCCcgactacgacgtggttgacat
          90                       100                      108
 Y  Y  C  F  Q  G  S  H  V  P  P  T  F  G  G  G  T  K  L  E  I  K  R
                CDR3

tccatcttcccaccatccagtgaggatccggc
---------+---------+---------+--                                                            339
aggtagaagggtggtaggtcactcctaggccg
```

Figure 1A

```
CAGGTCCAACTGCAGGAGTCTGGACCTGAGCTGAAGAAGCCTGGAGAGACAGTCAAGATATCCTGCAAGGCTTCTGGGTATACCTTCAGA
---------+---------+---------+---------+---------+---------+---------+---------+---------+  90
GTCCAGGTTGACGTCCTCAGACCTGGACTCGACTTCTTCGGACCTCTCTGTCAGTTCTATAGGACGTTCCGAAGACCCATATGGAAGTCT
 1                 10                  20                  30
 Q  V  Q  L  Q  E  S  G  P  E  L  K  K  P  G  E  T  V  K  I  S  C  K  A  S  G  Y  T  F  R

AACTATGGAATGAACTGGGTGAAACAGGCTCCAGGAAAGGGTTTAAAGTGGATGGGCTGGATAAACACCTACACTGGAGAGCCAACATAT
---------+---------+---------+---------+---------+---------+---------+---------+---------+  180
TTGATACCTTACTTGACCCACTTTGTCCGAGGTCCTTTCCCAAATTTCACCTACCCGACCTATTTGTGGATGTGACCTCTCGGTTGTATA
                                40                  50    52A
 N  Y  G  M  N  W  V  K  Q  A  P  G  K  G  L  K  W  M  G  W  I  N  T  Y  T  G  E  P  T  Y
    CDR1                                                                         CDR 2

GCTGATGACTTCAAGGGACGGTTTGCCTTCTCTTTGGAAACCTCTGCCAGCACTGCCTATTTGCAGATCAACAACGTCAAAAATGAGGAC
---------+---------+---------+---------+---------+---------+---------+---------+---------+  270
CGACTACTGAAGTTCCCTGCCAAACGGAAGAGAAACCTTTGGAGACGGTCGTGACGGATAAACGTCTAGTTGTTGCAGTTTTTACTCCTG
60                   70                  80    82A B  C
 A  D  D  F  K  G  R  F  A  F  S  L  E  T  S  A  S  T  A  Y  L  Q  I  N  N  V  K  N  E  D

ACGGCTACATATTTCTGTGCAAGAAAGGGATGGATGGATTTCAACGGTAGTAGCCTCGACTACTGGGGCCAAGGGACCACGGTCACCGTC
---------+---------+---------+---------+---------+---------+---------+---------+---------+  360
TGCCGATGTATAAAGACACGTTCTTTCCCTACCTACCTAAAGTTGCCATCATCGGAGCTGATGACCCCGGTTCCCTGGTGCCAGTGGCAG
         90                  100 A  B  C  D  E                    110
 T  A  T  Y  F  C  A  R  K  G  W  M  D  F  N  G  S  S  L  D  Y  W  G  Q  G  T  T  V  T  V
                                     CDR3

TCCTCA
------                                                                                     366
AGGAGT
   113
 S  S
```

Figure 1B

```
GACATCCAGCTGACCCAGACTCCACTCTCCCTGCCTGTCAGTCTTGGAGATCAAGCCTCCATCTCTTGCAGATCTAGTCAGAGCATTGTA
---------+---------+---------+---------+---------+---------+---------+---------+---------+  90
CTGTAGGTCGACTGGGTCTGAGGTGAGAGGGACGGACAGTCAGAACCTCTAGTTCGGAGGTAGAGAACGTCTAGATCAGTCTCGTAACAT

 D  I  Q  L  T  Q  T  P  L  S  L  P  V  S  L  G  D  Q  A  S  I  S  C  R  S  S  Q  S  I  V   30


CATAGTAATGGAAACACCTATTTAGAATGGTACCTGCAGAAACCAGGCCAGTCTCCAAACCTCCTCATCTACAAAGTTTCCAACCGATTT
---------+---------+---------+---------+---------+---------+---------+---------+---------+ 180
GTATCATTACCTTTGTGGATAAATCTTACCATGGACGTCTTTGGTCCGGTCAGAGGTTTGGAGGAGTAGATGTTTCAAAGGTTGGCTAAA

 H  S  N  G  N  T  Y  L  E  W  Y  L  Q  K  P  G  Q  S  P  N  L  L  I  Y  K  V  S  N  R  F   55
CDR1                                                                           CDR2
TCTGGGGTCCCAGACAGGTTCAGTGGCAGTGGATCAGGGACAGATTTCACACTCAAGATCAGCAGAGTGGAGGCTGAGGATCTGGGAGTT
---------+---------+---------+---------+---------+---------+---------+---------+---------+ 270
AGACCCCAGGGTCTGTCCAAGTCACCGTCACCTAGTCCCTGTCTAAAGTGTGAGTTCTAGTCGTCTCACCTCCGACTCCTAGACCCTCAA

 S  G  V  P  D  R  F  S  G  S  G  S  G  T  D  F  T  L  K  I  S  R  V  E  A  E  D  L  G  V   85


TATTACTGCTTTCAAGGTTCACATGTTCCTCCGACGTTCGGTGGAGGCACCAAGCTGGAGATCAAACGT
---------+---------+---------+---------+---------+---------+---------                      339
ATAATGACGAAAGTTCCAAGTGTACAAGGAGGCTGCAAGCCACCTCCGTGGTTCGACCTCTAGTTTGCA

 Y  Y  C  F  Q  G  S  H  V  P  P  T  F  G  G  G  T  K  L  E  I  K  R                      108
                     CDR3
```

Figure 2A shows the DNA and amino acid sequences of cMN3Vk domain. The CDR regions are in bold, underlined, and indicated. Nucleotide residues are numbered sequentially. Kabat's Ig molecule numbering is used for amino acid residues (same as in Fig. 1A).

```
CAGGTCCAACTGCAGGAGTCTGGACCTGAGCTGAAGAAGCCTGGAGAGACAGTCAAGATATCCTGCAAGGCTTCTGGGTATACCTTCAGA
---------+---------+---------+---------+---------+---------+---------+---------+---------+  90
GTCCAGGTTGACGTCCTCAGACCTGGACTCGACTTCTTCGGACCTCTCTGTCAGTTCTATAGGACGTTCCGAAGACCCATATGGAAGTCT

 Q  V  Q  L  Q  E  S  G  P  E  L  K  K  P  G  E  T  V  K  I  S  C  K  A  S  G  Y  T  F  R   30

AACTATGGAATGAACTGGGTGAAACAGGCTCCAGGAAAGGGTTTAAAGTGGATGGGCTGGATAAACACCTACACTGGAGAGCCAACATAT
---------+---------+---------+---------+---------+---------+---------+---------+---------+ 180
TTGATACCTTACTTGACCCACTTTGTCCGAGGTCCTTTCCCAAATTTCACCTACCCGACCTATTTGTGGATGTGACCTCTCGGTTGTATA

 N  Y  G  M  N  W  V  K  Q  A  P  G  K  G  L  K  W  M  G  W  I  N  T  Y  T  G  E  P  T  Y   59
 ---CDR1------                                           --------------CDR 2--------------

GCTGATGACTTCAAGGGACGGTTTGCCTTCTCTTTGGAAACCTCTGCCAGCACTGCCTATTTGCAGATCAACAACGTCAAAAATGAGGAC
---------+---------+---------+---------+---------+---------+---------+---------+---------+ 270
CGACTACTGAAGTTCCCTGCCAAACGGAAGAGAAACCTTTGGAGACGGTCGTGACGGATAAACGTCTAGTTGTTGCAGTTTTTACTCCTG

 A  D  D  F  K  G  R  F  A  F  S  L  E  T  S  A  S  T  A  Y  L  Q  I  N  N  V  K  N  E  D   86
 ----------------

ACGGCTACATATTTCTGTGCAAGAAAGGGATGGATGGATTTCAACGGTAGTAGCCTCGACTACTGGGGCCAAGGGACCACGGTCACCGTC
---------+---------+---------+---------+---------+---------+---------+---------+-------    360
TGCCGATGTATAAAGACACGTTCTTTCCCTACCTACCTAAAGTTGCCATCATCGGAGCTGATGACCCCGGTTCCCTGGTGCCAGTGGCAG

 T  A  T  Y  F  C  A  R  K  G  W  M  D  F  N  G  S  S  L  D  Y  W  G  Q  G  T  T  V  T  V  111
                         -------------------CDR3-------------------

TCCTCA
------                                                                                      366
AGGAGT

 S  S                                                                                       113
```

Figure 2B shows the DNA and amino acid sequences of cMN3VH domain. The CDR regions are in bold, underlined, and indicated. Nucleotide residues are numbered sequentially. Kabat's Ig molecule numbering is used for amino acid residues (same as in Fig. 1B).

```
         1        10        20     27ABCDE  30
REIVk    DIQMTQSPSSLSASVGDRVTITCQASQ-----DIIKYLNW
MN3Vk    SIVM••T•L••PV•L••QAS•S••S••SIVHSNGNT••E•
hMN3Vk   DIQL•••••••••••••••S•S••S••SIVHSNGNT••E•

             40        50        60        70
REIVk    YQQTPGKAPKLLIYEASNLQAGVPSRFSGSGSGTDYTFTI
MN3Vk    •L•K••QS•N••••KV••RFS•••D••••••••••F•LK•
hMN3Vk   •••K••••••••••KVSNRFS•••D••••••••••F••••

             80        90        100     108
REIVk    SSLQPEDIATYYCQQYQSLPYTFGQGTKVQITR
MN3Vk    •RVEA•••GV•••F•GSHV•P•••G•••LEIKR
hMN3Vk   •••••••••••••F•GSHV•P•••G••••EIKR
```

Figure 4A.

```
         1        10        20        30       40
EU_VH    PVQLVQSGAEVKKPGSSVKVSCKASGGTFSRSAIIWVRQA
MN3VH    QVQLQE••P•L••••ET••I••••••Y••RNYGMN••K••
hMN3VH   QVQLQ•••••••••••••••••••••Y••RNYGMN•••••

                  50 52 A      60        70
EU_VH    PGQGLEWMGGIVPMFGPPNYAQKFQGRVTITADESTNTAY
MN3VH    ••K••K•••W•NTYT•E•T••DD•K••FAFSLET•AS•••
hMN3VH   •••••••••W•NTYT•E•T••DD•K••FAF••••••••••

         80 82 A B C      90        100 A B C D E       110
EU_VH    MELSSLRSEDTAFYFCAGGYGIYS-----PEEYNGGLVTV
MN3VH    LQINNVKN••••T••••RKGWMDFNGSSLDY
hMN3VH   •••••••••••••••••RKGWMDFNGSSLDY

         103     110 113
KOL_VH   WGQGTPVTVSS
MN3VH    •••••T•TVSS
hMN3VH   •••••••TVSS
```

Figure4B.

```
                   XbaI
                   tctagacacaggacctcaccATGGGATGGAGCTGTATCATCCTCTTCTTGGTAGCAACAGCTACaggta
                                              M  G  W  S  C  I  I  L  F  L  V  A  T  A  T

agggctcacagtagcaggcttgaggtctggacatatatatgggtgacaatgacatccactttgcctttctctccacAGGTGTCCACTCC
                                                                               G  V  H  S

      PvuII
GACATCCAGCTGACCCAGAGCCCAAGCAGCCTGAGCGCCAGCGTGGGTGACAGAGTGTCCATCTCTTGTAGATCCAGTCAGAGCATTGTA   90
 D  I  Q  L  T  Q  S  P  S  S  L  S  A  S  V  G  D  R  V  S  I  S  C  R  S  S  Q  S  I  V   27C

CATAGTAATGGAAACACCTATTTAGAATGGTACCAGCAGAAGCCAGGTAAGGCTCCAAAGCTGCTGATCTACAAAGTTTCCAACCGATTT  180
 H  S  N  G  N  T  Y  L  E  W  Y  Q  Q  K  P  G  K  A  P  K  L  L  I  Y  K  V  S  N  R  F   55
 CDR1                                                                            CDR2

TCCGGAGTGCCAGACAGATTCAGCGGTAGCGGTAGCGGTACCGACTTCACCTTCACCATCAGCAGCCTCCAGCCAGAGGACATCGCCACC  270
 S  G  V  P  D  R  F  S  G  S  G  S  G  T  D  F  T  F  T  I  S  S  L  Q  P  E  D  I  A  T   85

                                                        BglII/BclI
TACTACTGCTTTCAAGGTTCACATGTTCCTCCGACGTTCGGCGGCGGGACCAAGGTGGAGATCAAACgtgagtagaatttaaactttgct  337
 Y  Y  C  F  Q  G  S  H  V  P  P  T  F  G  G  G  T  K  V  E  I  K                            107
                    CDR3

        BamHI
tcctcagttggatcc
```

Figure 5A.

```
                 XhoI
                 ctcgagcacacaggacctcaccATGGGATGGAGCTGTATCATCCTCTTCTTGGTAGCAACAGCTACaggta
                                              M G W S C I I L F L V A T A T

agggggctcacagtagcaggcttgaggtctggacatatatatgggtgacaatgacatccactttgcctttctctccacAGGTGTCCACTCC
                                                                                G V H S

         PstI
CAGGTCCAACTGCAGCAGTCTGGAGCTGAGGTCAAGAAGCCTGGATCTAGCGTCAAGGTCTCCTGCAAGGCTTCTGGGTATACCTTCAGA   90
 Q  V  Q  L  Q  Q  S  G  A  E  V  K  K  P  G  S  S  V  K  V  S  C  K  A  S  G  Y  T  F  R   30

AACTATGGAATGAACTGGGTGAGACAGGCTCCAGGACAGGGTTTAGAGTGGATGGGCTGGATAAACACCTACACCGGTGAGCCAACATAT  180
 N  Y  G  M  N  W  V  R  Q  A  P  G  Q  G  L  E  W  M  G  W  I  N  T  Y  T  G  E  P  T  Y   59
    CDR1                                                                          CDR2

GCTGATGACTTCAAGGGACGGTTTGCCTTCACAGCCGACGAATCTACCAACACTGCCTATATGGAGCTGTCTAGCTTGAGATCTGAGGAC  270
 A  D  D  F  K  G  R  F  A  F  T  A  D  E  S  T  N  T  A  Y  M  E  L  S  S  L  R  S  E  D   75

                                                                                BstEII
ACGGCTTTCTATTTCTGTGCAAGAAAGGGATGGATGGATTTCAACGGTAGTAGCCTCGACTACTGGGGCCAAGGGACCCCGGTCACCGTC  360
 T  A  F  Y  F  C  A  R  K  G  W  M  D  F  N  G  S  S  L  D  Y  W  G  Q  G  T  P  V  T  V  111
                                    CDR3

TCCTCAGgtgagtccttacaacctctctcttctattcagcttaaatagattttactgcatttgttgggggggaaatgtgtgtatctgaat  367
 S  S                                                                                       113

ttcaggtcatgaaggactagggacaccttgggagtcagaaagggtcattgggagcccgggctgatgcagacagacatcctcagctcccag

                   BamHI
acttcatggccagagatttataggatcc
```

Figure 5B.

SEQUENCE LISTING

```
<160> NUMBER OF SEQ ID NOS: 51

<210> SEQ ID NO 1
<211> LENGTH: 16
<212> TYPE: PRT
<213> ORGANISM: Artificial Sequence
<220> FEATURE:
<223> OTHER INFORMATION: Description of Artificial Sequence: Chimeric
      aminoacid sequence

<400> SEQUENCE: 1

Arg Ser Ser Gln Ser Ile Val His Ser Asn Gly Asn Thr Tyr Leu Glu
  1               5                  10                  15


<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Chimeric
      aminoacid sequence

<400> SEQUENCE: 2

Lys Val Ser Asn Arg Phe Ser
  1               5


<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Chimeric
      aminoacid sequence

<400> SEQUENCE: 3

Phe Gln Gly Ser His Val Pro Pro Thr
  1               5


<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Chimeric
      aminoacid sequence

<400> SEQUENCE: 4

Asn Tyr Gly Met Asn
  1               5


<210> SEQ ID NO 5
<211> LENGTH: 17
<212> TYPE: PRT
<213> ORGANISM: Artificial Sequence
```

-continued

```
<220> FEATURE:
<223> OTHER INFORMATION: Description of Artificial Sequence: Chimeric
      aminoacid sequence

<400> SEQUENCE: 5

Trp Ile Asn Thr Tyr Thr Gly Glu Pro Thr Tyr Ala Asp Asp Phe Lys
  1               5                  10                  15

Gly


<210> SEQ ID NO 6
<211> LENGTH: 13
<212> TYPE: PRT
<213> ORGANISM: Artificial Sequence
<220> FEATURE:
<223> OTHER INFORMATION: Description of Artificial Sequence: Chimeric
      aminoacid sequence

<400> SEQUENCE: 6

Lys Gly Trp Met Asp Phe Asn Gly Ser Ser Leu Asp Tyr
  1               5                  10


<210> SEQ ID NO 7
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Lys(HSG)
<220> FEATURE:
<221> NAME/KEY: MOD_RES
<222> LOCATION: (4)
<223> OTHER INFORMATION: Lys(HSG)
<220> FEATURE:
<223> OTHER INFORMATION: c-term amidated

<400> SEQUENCE: 7

Phe Lys Tyr Lys
  1


<210> SEQ ID NO 8
<211> LENGTH: 392
<212> TYPE: DNA
<213> ORGANISM: Mus musculus
<220> FEATURE:
<221> NAME/KEY: CDS
<222> LOCATION: (1)..(339)

<400> SEQUENCE: 8

agc att gtg atg acc cag act cca ctc tcc ctg cct gtc agt ctt gga   48
Ser Ile Val Met Thr Gln Thr Pro Leu Ser Leu Pro Val Ser Leu Gly
  1               5                  10                  15

gat caa gcc tcc atc tct tgc aga tct agt cag agc att gta cat agt   96
Asp Gln Ala Ser Ile Ser Cys Arg Ser Ser Gln Ser Ile Val His Ser
             20                  25                  30

aat gga aac acc tat tta gaa tgg tac ctg cag aaa cca ggc cag tct   144
Asn Gly Asn Thr Tyr Leu Glu Trp Tyr Leu Gln Lys Pro Gly Gln Ser
         35                  40                  45

cca aac ctc ctc atc tac aaa gtt tcc aac cga ttt tct ggg gtc cca   192
Pro Asn Leu Leu Ile Tyr Lys Val Ser Asn Arg Phe Ser Gly Val Pro
     50                  55                  60

gac agg ttc agt ggc agt gga tca ggg aca gat ttc aca ctc aag atc   240
Asp Arg Phe Ser Gly Ser Gly Ser Gly Thr Asp Phe Thr Leu Lys Ile
 65                  70                  75                  80
```

```
agc aga gtg gag gct gag gat ctg gga gtt tat tac tgc ttt caa ggt   288
Ser Arg Val Glu Ala Glu Asp Leu Gly Val Tyr Tyr Cys Phe Gln Gly
                 85                  90                  95

tca cat gtt cct ccg acg ttc ggt gga ggc acc aag ctg gaa atc aaa   336
Ser His Val Pro Pro Thr Phe Gly Gly Gly Thr Lys Leu Glu Ile Lys
            100                 105                 110

cgg gctgatgctg caccaactgt atccatcttc ccaccatcca gtgaggatcc ggc    392
Arg


<210> SEQ ID NO 9
<211> LENGTH: 113
<212> TYPE: PRT
<213> ORGANISM: Mus musculus

<400> SEQUENCE: 9

Ser Ile Val Met Thr Gln Thr Pro Leu Ser Leu Pro Val Ser Leu Gly
  1               5                  10                  15

Asp Gln Ala Ser Ile Ser Cys Arg Ser Ser Gln Ser Ile Val His Ser
             20                  25                  30

Asn Gly Asn Thr Tyr Leu Glu Trp Tyr Leu Gln Lys Pro Gly Gln Ser
         35                  40                  45

Pro Asn Leu Leu Ile Tyr Lys Val Ser Asn Arg Phe Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Tyr Cys Phe Gln Gly
                 85                  90                  95

Ser His Val Pro Pro Thr Phe Gly Gly Gly Thr Lys Leu Glu Ile Lys
            100                 105                 110

Arg


<210> SEQ ID NO 10
<211> LENGTH: 366
<212> TYPE: DNA
<213> ORGANISM: Mus musculus
<220> FEATURE:
<221> NAME/KEY: CDS
<222> LOCATION: (1)..(366)

<400> SEQUENCE: 10

cag gtc caa ctg cag gag tct gga cct gag ctg aag aag cct gga gag   48
Gln Val Gln Leu Gln Glu Ser Gly Pro Glu Leu Lys Lys Pro Gly Glu
  1               5                  10                  15

aca gtc aag ata tcc tgc aag gct tct ggg tat acc ttc aga aac tat   96
Thr Val Lys Ile Ser Cys Lys Ala Ser Gly Tyr Thr Phe Arg Asn Tyr
             20                  25                  30

gga atg aac tgg gtg aaa cag gct cca gga aag ggt tta aag tgg atg   144
Gly Met Asn Trp Val Lys Gln Ala Pro Gly Lys Gly Leu Lys Trp Met
         35                  40                  45

ggc tgg ata aac acc tac act gga gag cca aca tat gct gat gac ttc   192
Gly Trp Ile Asn Thr Tyr Thr Gly Glu Pro Thr Tyr Ala Asp Asp Phe
     50                  55                  60

aag gga cgg ttt gcc ttc tct ttg gaa acc tct gcc agc act gcc tat   240
Lys Gly Arg Phe Ala Phe Ser Leu Glu Thr Ser Ala Ser Thr Ala Tyr
 65                  70                  75                  80

ttg cag atc aac aac gtc aaa aat gag gac acg gct aca tat ttc tgt   288
Leu Gln Ile Asn Asn Val Lys Asn Glu Asp Thr Ala Thr Tyr Phe Cys
                 85                  90                  95

gca aga aag gga tgg atg gat ttc aac ggt agt agc ctc gac tac tgg   336
```

-continued

```
Ala Arg Lys Gly Trp Met Asp Phe Asn Gly Ser Ser Leu Asp Tyr Trp
            100                 105                 110

ggc caa ggg acc acg gtc acc gtc tcc tca                           366
Gly Gln Gly Thr Thr Val Thr Val Ser Ser
        115                 120


<210> SEQ ID NO 11
<211> LENGTH: 122
<212> TYPE: PRT
<213> ORGANISM: Mus musculus

<400> SEQUENCE: 11

Gln Val Gln Leu Gln Glu Ser Gly Pro Glu Leu Lys Lys Pro Gly Glu
  1               5                  10                  15

Thr Val Lys Ile Ser Cys Lys Ala Ser Gly Tyr Thr Phe Arg Asn Tyr
             20                  25                  30

Gly Met Asn Trp Val Lys Gln Ala Pro Gly Lys Gly Leu Lys Trp Met
         35                  40                  45

Gly Trp Ile Asn Thr Tyr Thr Gly Glu Pro Thr Tyr Ala Asp Asp Phe
     50                  55                  60

Lys Gly Arg Phe Ala Phe Ser Leu Glu Thr Ser Ala Ser Thr Ala Tyr
 65                  70                  75                  80

Leu Gln Ile Asn Asn Val Lys Asn Glu Asp Thr Ala Thr Tyr Phe Cys
                 85                  90                  95

Ala Arg Lys Gly Trp Met Asp Phe Asn Gly Ser Ser Leu Asp Tyr Trp
            100                 105                 110

Gly Gln Gly Thr Thr Val Thr Val Ser Ser
        115                 120


<210> SEQ ID NO 12
<211> LENGTH: 339
<212> TYPE: DNA
<213> ORGANISM: Artificial Sequence
<220> FEATURE:
<223> OTHER INFORMATION: Description of Artificial Sequence: Chimeric
      cMN3Vk nucleotide sequence
<220> FEATURE:
<221> NAME/KEY: CDS
<222> LOCATION: (1)..(339)

<400> SEQUENCE: 12

gac atc cag ctg acc cag act cca ctc tcc ctg cct gtc agt ctt gga   48
Asp Ile Gln Leu Thr Gln Thr Pro Leu Ser Leu Pro Val Ser Leu Gly
  1               5                  10                  15

gat caa gcc tcc atc tct tgc aga tct agt cag agc att gta cat agt   96
Asp Gln Ala Ser Ile Ser Cys Arg Ser Ser Gln Ser Ile Val His Ser
             20                  25                  30

aat gga aac acc tat tta gaa tgg tac ctg cag aaa cca ggc cag tct   144
Asn Gly Asn Thr Tyr Leu Glu Trp Tyr Leu Gln Lys Pro Gly Gln Ser
         35                  40                  45

cca aac ctc ctc atc tac aaa gtt tcc aac cga ttt tct ggg gtc cca   192
Pro Asn Leu Leu Ile Tyr Lys Val Ser Asn Arg Phe Ser Gly Val Pro
     50                  55                  60

gac agg ttc agt ggc agt gga tca ggg aca gat ttc aca ctc aag atc   240
Asp Arg Phe Ser Gly Ser Gly Ser Gly Thr Asp Phe Thr Leu Lys Ile
 65                  70                  75                  80

agc aga gtg gag gct gag gat ctg gga gtt tat tac tgc ttt caa ggt   288
Ser Arg Val Glu Ala Glu Asp Leu Gly Val Tyr Tyr Cys Phe Gln Gly
                 85                  90                  95

tca cat gtt cct ccg acg ttc ggt gga ggc acc aag ctg gag atc aaa   336
Ser His Val Pro Pro Thr Phe Gly Gly Gly Thr Lys Leu Glu Ile Lys
```

-continued

```
            100                 105                 110

cgt                                                                339
Arg


<210> SEQ ID NO 13
<211> LENGTH: 113
<212> TYPE: PRT
<213> ORGANISM: Artificial Sequence
<220> FEATURE:
<223> OTHER INFORMATION: Description of Artificial Sequence: Chimeric
      cMN3Vk amino acid sequence

<400> SEQUENCE: 13

Asp Ile Gln Leu Thr Gln Thr Pro Leu Ser Leu Pro Val Ser Leu Gly
  1               5                  10                  15

Asp Gln Ala Ser Ile Ser Cys Arg Ser Ser Gln Ser Ile Val His Ser
             20                  25                  30

Asn Gly Asn Thr Tyr Leu Glu Trp Tyr Leu Gln Lys Pro Gly Gln Ser
         35                  40                  45

Pro Asn Leu Leu Ile Tyr Lys Val Ser Asn Arg Phe Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Tyr Cys Phe Gln Gly
                 85                  90                  95

Ser His Val Pro Pro Thr Phe Gly Gly Gly Thr Lys Leu Glu Ile Lys
            100                 105                 110

Arg


<210> SEQ ID NO 14
<211> LENGTH: 366
<212> TYPE: DNA
<213> ORGANISM: Artificial Sequence
<220> FEATURE:
<223> OTHER INFORMATION: Description of Artificial Sequence: Chimeric
      cMN3VH nucleotide sequence
<220> FEATURE:
<221> NAME/KEY: CDS
<222> LOCATION: (1)..(366)

<400> SEQUENCE: 14

cag gtc caa ctg cag gag tct gga cct gag ctg aag aag cct gga gag   48
Gln Val Gln Leu Gln Glu Ser Gly Pro Glu Leu Lys Lys Pro Gly Glu
  1               5                  10                  15

aca gtc aag ata tcc tgc aag gct tct ggg tat acc ttc aga aac tat   96
Thr Val Lys Ile Ser Cys Lys Ala Ser Gly Tyr Thr Phe Arg Asn Tyr
             20                  25                  30

gga atg aac tgg gtg aaa cag gct cca gga aag ggt tta aag tgg atg   144
Gly Met Asn Trp Val Lys Gln Ala Pro Gly Lys Gly Leu Lys Trp Met
         35                  40                  45

ggc tgg ata aac acc tac act gga gag cca aca tat gct gat gac ttc   192
Gly Trp Ile Asn Thr Tyr Thr Gly Glu Pro Thr Tyr Ala Asp Asp Phe
     50                  55                  60

aag gga cgg ttt gcc ttc tct ttg gaa acc tct gcc agc act gcc tat   240
Lys Gly Arg Phe Ala Phe Ser Leu Glu Thr Ser Ala Ser Thr Ala Tyr
 65                  70                  75                  80

ttg cag atc aac aac gtc aaa aat gag gac acg gct aca tat ttc tgt   288
Leu Gln Ile Asn Asn Val Lys Asn Glu Asp Thr Ala Thr Tyr Phe Cys
                 85                  90                  95

gca aga aag gga tgg atg gat ttc aac ggt agt agc ctc gac tac tgg   336
Ala Arg Lys Gly Trp Met Asp Phe Asn Gly Ser Ser Leu Asp Tyr Trp
```

-continued

```
            100                 105                 110

ggc caa ggg acc acg gtc acc gtc tcc tca                             366
Gly Gln Gly Thr Thr Val Thr Val Ser Ser
        115                 120


<210> SEQ ID NO 15
<211> LENGTH: 122
<212> TYPE: PRT
<213> ORGANISM: Artificial Sequence
<220> FEATURE:
<223> OTHER INFORMATION: Description of Artificial Sequence: Chimeric
      cMN3VH amino acid sequence

<400> SEQUENCE: 15

Gln Val Gln Leu Gln Glu Ser Gly Pro Glu Leu Lys Lys Pro Gly Glu
  1               5                  10                  15

Thr Val Lys Ile Ser Cys Lys Ala Ser Gly Tyr Thr Phe Arg Asn Tyr
             20                  25                  30

Gly Met Asn Trp Val Lys Gln Ala Pro Gly Lys Gly Leu Lys Trp Met
         35                  40                  45

Gly Trp Ile Asn Thr Tyr Thr Gly Glu Pro Thr Tyr Ala Asp Asp Phe
     50                  55                  60

Lys Gly Arg Phe Ala Phe Ser Leu Glu Thr Ser Ala Ser Thr Ala Tyr
 65                  70                  75                  80

Leu Gln Ile Asn Asn Val Lys Asn Glu Asp Thr Ala Thr Tyr Phe Cys
                 85                  90                  95

Ala Arg Lys Gly Trp Met Asp Phe Asn Gly Ser Ser Leu Asp Tyr Trp
            100                 105                 110

Gly Gln Gly Thr Thr Val Thr Val Ser Ser
        115                 120


<210> SEQ ID NO 16
<211> LENGTH: 108
<212> TYPE: PRT
<213> ORGANISM: Homo sapiens

<400> SEQUENCE: 16

Asp Ile Gln Met Thr Gln Ser Pro Ser Ser Leu Ser Ala Ser Val Gly
  1               5                  10                  15

Asp Arg Val Thr Ile Thr Cys Gln Ala Ser Gln Asp Ile Ile Lys Tyr
             20                  25                  30

Leu Asn Trp Tyr Gln Gln Thr Pro Gly Lys Ala Pro Lys Leu Leu Ile
         35                  40                  45

Tyr Glu Ala Ser Asn Leu Gln Ala Gly Val Pro Ser Arg Phe Ser Gly
     50                  55                  60

Ser Gly Ser Gly Thr Asp Tyr Thr Phe Thr Ile Ser Ser Leu Gln Pro
 65                  70                  75                  80

Glu Asp Ile Ala Thr Tyr Tyr Cys Gln Gln Tyr Gln Ser Leu Pro Tyr
                 85                  90                  95

Thr Phe Gly Gln Gly Thr Lys Val Gln Ile Thr Arg
            100                 105


<210> SEQ ID NO 17
<211> LENGTH: 113
<212> TYPE: PRT
<213> ORGANISM: Mus musculus

<400> SEQUENCE: 17

Ser Ile Val Met Thr Gln Thr Pro Leu Ser Leu Pro Val Ser Leu Gly
```

-continued

```
 1               5                   10                  15

Asp Gln Ala Ser Ile Ser Cys Gln Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Asn Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Ile Gly Val Tyr Tyr Cys Phe Gln Gly
                85                  90                  95

Ser His Val Pro Pro Thr Phe Gly Gly Gly Thr Lys Leu Glu Ile Lys
            100                 105                 110

Arg


<210> SEQ ID NO 18
<211> LENGTH: 113
<212> TYPE: PRT
<213> ORGANISM: Artificial Sequence
<220> FEATURE:
<223> OTHER INFORMATION: Description of Artificial Sequence: Humanized
      amino acid sequence

<400> SEQUENCE: 18

Asp Ile Gln Leu Thr Gln Ser Pro Ser Ser Leu Ser Ala Ser Val Gly
 1               5                   10                  15

Asp Arg Val Ser Ile Ser Cys Gln Ser Ser Gln Ser Ile Val His Ser
            20                  25                  30

Asn Gly Asn Thr Tyr Leu Glu Trp Tyr Gln Gln Lys Pro Gly Lys Ala
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Phe Thr Ile
65                  70                  75                  80

Ser Ser Leu Gln Pro Glu Asp Ile Ala Thr Tyr Tyr Cys Phe Gln Gly
                85                  90                  95

Ser His Val Pro Pro Thr Phe Gly Gly Gly Thr Lys Val Glu Ile Lys
            100                 105                 110

Arg


<210> SEQ ID NO 19
<211> LENGTH: 126
<212> TYPE: PRT
<213> ORGANISM: Homo sapiens

<400> SEQUENCE: 19

Pro Val Gln Leu Val Gln Ser Gly Ala Glu Val Lys Lys Pro Gly Ser
 1               5                   10                  15

Ser Val Lys Val Ser Cys Lys Ala Ser Gly Gly Thr Phe Ser Arg Ser
            20                  25                  30

Ala Ile Ile Trp Val Arg Gln Ala Pro Gly Gln Gly Leu Glu Trp Met
        35                  40                  45

Gly Gly Ile Val Pro Met Phe Gly Pro Pro Asn Tyr Ala Gln Lys Phe
    50                  55                  60

Gln Gly Arg Val Thr Ile Thr Ala Asp Glu Ser Thr Asn Thr Ala Tyr
65                  70                  75                  80
```

-continued

```
Met Glu Leu Ser Ser Leu Arg Ser Glu Asp Thr Ala Phe Tyr Phe Cys
                85                  90                  95

Ala Gly Gly Tyr Gly Ile Tyr Ser Pro Glu Glu Tyr Asn Gly Gly Leu
            100                 105                 110

Val Thr Val Trp Gly Gln Gly Thr Pro Val Thr Val Ser Ser
        115                 120                 125


<210> SEQ ID NO 20
<211> LENGTH: 122
<212> TYPE: PRT
<213> ORGANISM: Mus musculus

<400> SEQUENCE: 20

Gln Val Gln Leu Gln Glu Ser Gly Pro Glu Leu Lys Lys Pro Gly Glu
  1               5                  10                  15

Thr Val Lys Ile Ser Cys Lys Ala Ser Gly Tyr Thr Phe Arg Asn Tyr
            20                  25                  30

Gly Met Asn Trp Val Lys Gln Ala Pro Gly Lys Gly Leu Lys Trp Met
        35                  40                  45

Gly Trp Ile Asn Thr Tyr Thr Gly Glu Pro Thr Tyr Ala Asp Asp Phe
     50                  55                  60

Lys Gly Arg Phe Ala Phe Ser Leu Glu Thr Ser Ala Ser Thr Ala Tyr
 65                  70                  75                  80

Leu Gln Ile Asn Asn Val Lys Asn Glu Asp Thr Ala Thr Tyr Phe Cys
                85                  90                  95

Ala Arg Lys Gly Trp Met Asp Phe Asn Gly Ser Ser Leu Asp Tyr Trp
            100                 105                 110

Gly Gln Gly Thr Thr Val Thr Val Ser Ser
        115                 120


<210> SEQ ID NO 21
<211> LENGTH: 122
<212> TYPE: PRT
<213> ORGANISM: Artificial Sequence
<220> FEATURE:
<223> OTHER INFORMATION: Description of Artificial Sequence: Humanized
      amino acid sequence

<400> SEQUENCE: 21

Gln Val Gln Leu Gln Gln Ser Gly Ala Glu Val Lys Lys Pro Gly Ser
  1               5                  10                  15

Ser Val Lys Val Ser Cys Lys Ala Ser Gly Tyr Thr Phe Arg Asn Tyr
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Pro Thr Tyr Ala Asp Asp Phe
     50                  55                  60

Lys Gly Arg Phe Ala Phe Thr Ala Asp Glu Ser Thr Asn Thr Ala Tyr
 65                  70                  75                  80

Met Glu Leu Ser Ser Leu Arg Ser Glu Asp Thr Ala Phe Tyr Phe Cys
                85                  90                  95

Ala Arg Lys Gly Trp Met Asp Phe Asn Gly Ser Ser Leu Asp Tyr Trp
            100                 105                 110

Gly Gln Gly Thr Pro Val Thr Val Ser Ser
        115                 120


<210> SEQ ID NO 22
<211> LENGTH: 11
```

```
<212> TYPE: PRT
<213> ORGANISM: Homo sapiens

<400> SEQUENCE: 22

Trp Gly Gln Gly Thr Pro Val Thr Val Ser Ser
  1               5                  10


<210> SEQ ID NO 23
<211> LENGTH: 534
<212> TYPE: DNA
<213> ORGANISM: Artificial Sequence
<220> FEATURE:
<223> OTHER INFORMATION: Description of Artificial Sequence: Synthetic
      nucleotide sequence encoding light chain amino
      acid sequence
<220> FEATURE:
<221> NAME/KEY: CDS
<222> LOCATION: (21)..(64)
<220> FEATURE:
<221> NAME/KEY: CDS
<222> LOCATION: (147)..(495)

<400> SEQUENCE: 23

tctagacaca ggacctcacc atg gga tgg agc tgt atc atc ctc ttc ttg         50
                      Met Gly Trp Ser Cys Ile Ile Leu Phe Leu
                        1               5                  10

gta gca aca gct ac  aggtaagggg ctcacagtag caggcttgag gtctggacat      104
Val Ala Thr Ala Thr
                 15

atatatgggt gacaatgaca tccactttgc ctttctctcc ac a ggt gtc cac tcc     159
                                                 Gly Val His Ser

gac atc cag ctg acc cag agc cca agc agc ctg agc gcc agc gtg ggt      207
Asp Ile Gln Leu Thr Gln Ser Pro Ser Ser Leu Ser Ala Ser Val Gly
 20                  25                  30                  35

gac aga gtg tcc atc tct tgt aga tcc agt cag agc att gta cat agt      255
Asp Arg Val Ser Ile Ser Cys Arg Ser Ser Gln Ser Ile Val His Ser
                 40                  45                  50

aat gga aac acc tat tta gaa tgg tac cag cag aag cca ggt aag gct      303
Asn Gly Asn Thr Tyr Leu Glu Trp Tyr Gln Gln Lys Pro Gly Lys Ala
             55                  60                  65

cca aag ctg ctg atc tac aaa gtt tcc aac cga ttt tcc gga gtg cca      351
Pro Lys Leu Leu Ile Tyr Lys Val Ser Asn Arg Phe Ser Gly Val Pro
         70                  75                  80

gac aga ttc agc ggt agc ggt agc ggt acc gac ttc acc ttc acc atc      399
Asp Arg Phe Ser Gly Ser Gly Ser Gly Thr Asp Phe Thr Phe Thr Ile
     85                  90                  95

agc agc ctc cag cca gag gac atc gcc acc tac tac tgc ttt caa ggt      447
Ser Ser Leu Gln Pro Glu Asp Ile Ala Thr Tyr Tyr Cys Phe Gln Gly
100                 105                 110                 115

tca cat gtt cct ccg acg ttc ggc ggc ggg acc aag gtg gag atc aaa      495
Ser His Val Pro Pro Thr Phe Gly Gly Gly Thr Lys Val Glu Ile Lys
                120                 125                 130

cgtgagtaga atttaaactt tgcttcctca gttggatcc                            534


<210> SEQ ID NO 24
<211> LENGTH: 131
<212> TYPE: PRT
<213> ORGANISM: Artificial Sequence
<220> FEATURE:
<223> OTHER INFORMATION: Description of Artificial Sequence: Synthetic
      light chain amino acid sequence

<400> SEQUENCE: 24

Met Gly Trp Ser Cys Ile Ile Leu Phe Leu Val Ala Thr Ala Thr Gly
```

-continued

```
 1               5                  10                  15

Val His Ser Asp Ile Gln Leu Thr Gln Ser Pro Ser Ser Leu Ser Ala
             20                  25                  30

Ser Val Gly Asp Arg Val Ser Ile Ser Cys Arg Ser Ser Gln Ser Ile
         35                  40                  45

Val His Ser Asn Gly Asn Thr Tyr Leu Glu Trp Tyr Gln Gln Lys Pro
     50                  55                  60

Gly Lys Ala Pro Lys Leu Leu Ile Tyr Lys Val Ser Asn Arg Phe Ser
 65                  70                  75                  80

Gly Val Pro Asp Arg Phe Ser Gly Ser Gly Ser Gly Thr Asp Phe Thr
                 85                  90                  95

Phe Thr Ile Ser Ser Leu Gln Pro Glu Asp Ile Ala Thr Tyr Tyr Cys
            100                 105                 110

Phe Gln Gly Ser His Val Pro Pro Thr Phe Gly Gly Gly Thr Lys Val
        115                 120                 125

Glu Ile Lys
    130


<210> SEQ ID NO 25
<211> LENGTH: 729
<212> TYPE: DNA
<213> ORGANISM: Artificial Sequence
<220> FEATURE:
<223> OTHER INFORMATION: Description of Artificial Sequence: Synthetic
      nucleotide sequence encoding heavy chain amino
      acid sequence
<220> FEATURE:
<221> NAME/KEY: CDS
<222> LOCATION: (23)..(66)
<220> FEATURE:
<221> NAME/KEY: CDS
<222> LOCATION: (149)..(528)

<400> SEQUENCE: 25

ctcgagcaca caggacctca cc atg gga tgg agc tgt atc atc ctc ttc ttg      52
                         Met Gly Trp Ser Cys Ile Ile Leu Phe Leu
                           1               5                  10

gta gca aca gct ac  aggtaagggg ctcacagtag caggcttgag gtctggacat      106
Val Ala Thr Ala Thr
                 15

atatatgggt gacaatgaca tccactttgc ctttctctcc ac a ggt gtc cac tcc     161
                                                Gly Val His Ser

cag gtc caa ctg cag cag tct gga gct gag gtc aag aag cct gga tct      209
Gln Val Gln Leu Gln Gln Ser Gly Ala Glu Val Lys Lys Pro Gly Ser
 20                  25                  30                  35

agc gtc aag gtc tcc tgc aag gct tct ggg tat acc ttc aga aac tat      257
Ser Val Lys Val Ser Cys Lys Ala Ser Gly Tyr Thr Phe Arg Asn Tyr
                 40                  45                  50

gga atg aac tgg gtg aga cag gct cca gga cag ggt tta gag tgg atg      305
Gly Met Asn Trp Val Arg Gln Ala Pro Gly Gln Gly Leu Glu Trp Met
             55                  60                  65

ggc tgg ata aac acc tac acc ggt gag cca aca tat gct gat gac ttc      353
Gly Trp Ile Asn Thr Tyr Thr Gly Glu Pro Thr Tyr Ala Asp Asp Phe
         70                  75                  80

aag gga cgg ttt gcc ttc aca gcc gac gaa tct acc aac act gcc tat      401
Lys Gly Arg Phe Ala Phe Thr Ala Asp Glu Ser Thr Asn Thr Ala Tyr
     85                  90                  95

atg gag ctg tct agc ttg aga tct gag gac acg gct ttc tat ttc tgt      449
Met Glu Leu Ser Ser Leu Arg Ser Glu Asp Thr Ala Phe Tyr Phe Cys
100                 105                 110                 115
```

-continued

```
gca aga aag gga tgg atg gat ttc aac ggt agt agc ctc gac tac tgg      497
Ala Arg Lys Gly Trp Met Asp Phe Asn Gly Ser Ser Leu Asp Tyr Trp
                120                 125                 130

ggc caa ggg acc ccg gtc acc gtc tcc tca ggtgagtcct tacaacctct        547
Gly Gln Gly Thr Pro Val Thr Val Ser Ser
            135                 140

ctcttctatt cagcttaaat agattttact gcatttgttg ggggggaaat gtgtgtatct    607

gaatttcagg tcatgaagga ctagggacac cttgggagtc agaaagggtc attgggagcc    667

cgggctgatg cagacagaca tcctcagctc ccagacttca tggccagaga tttataggat    727

cc                                                                   729


<210> SEQ ID NO 26
<211> LENGTH: 141
<212> TYPE: PRT
<213> ORGANISM: Artificial Sequence
<220> FEATURE:
<223> OTHER INFORMATION: Description of Artificial Sequence: Synthetic
      heavy chain amino acid sequence

<400> SEQUENCE: 26

Met Gly Trp Ser Cys Ile Ile Leu Phe Leu Val Ala Thr Ala Thr Gly
  1               5                  10                  15

Val His Ser Gln Val Gln Leu Gln Gln Ser Gly Ala Glu Val Lys Lys
             20                  25                  30

Pro Gly Ser Ser Val Lys Val Ser Cys Lys Ala Ser Gly Tyr Thr Phe
         35                  40                  45

Arg Asn Tyr Gly Met Asn Trp Val Arg Gln Ala Pro Gly Gln Gly Leu
     50                  55                  60

Glu Trp Met Gly Trp Ile Asn Thr Tyr Thr Gly Glu Pro Thr Tyr Ala
 65                  70                  75                  80

Asp Asp Phe Lys Gly Arg Phe Ala Phe Thr Ala Asp Glu Ser Thr Asn
                 85                  90                  95

Thr Ala Tyr Met Glu Leu Ser Ser Leu Arg Ser Glu Asp Thr Ala Phe
            100                 105                 110

Tyr Phe Cys Ala Arg Lys Gly Trp Met Asp Phe Asn Gly Ser Ser Leu
        115                 120                 125

Asp Tyr Trp Gly Gln Gly Thr Pro Val Thr Val Ser Ser
    130                 135                 140


<210> SEQ ID NO 27
<211> LENGTH: 4
<212> TYPE: PRT
<213> ORGANISM: Artificial Sequence
<220> FEATURE:
<223> OTHER INFORMATION: Description of Artificial Sequence: Synthetic
      linker

<400> SEQUENCE: 27

Gly Gly Gly Ser
  1


<210> SEQ ID NO 28
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
```

-continued acagtcactg agctgg 16

<210> SEQ ID NO 29
<211> LENGTH: 36
<212> TYPE: DNA
<213> ORGANISM: Artificial Sequence
<220> FEATURE:
<223> OTHER INFORMATION: Description of Artificial Sequence: Synthetic primer

<400> SEQUENCE: 29
gccggatcct gactggatgg tgggaagatg gataca 36

<210> SEQ ID NO 30
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 30
gacattcagc tgacccagtc tcca 24

<210> SEQ ID NO 31
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 31
ctcactggat ggtgggaaga tggatacagt tgg 33

<210> SEQ ID NO 32
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 32
aggtsmarct gcagsagtcw gg 22

<210> SEQ ID NO 33
<211> LENGTH: 30
<212> TYPE: DNA
<213> ORGANISM: Artificial Sequence
<220> FEATURE:
<223> OTHER INFORMATION: Description of Artificial Sequence: Synthetic probe

<400> SEQUENCE: 33
agactgcagg agagctggga aggtgtgcac 30

<210> SEQ ID NO 34
<211> LENGTH: 30
<212> TYPE: DNA
<213> ORGANISM: Artificial Sequence
<220> FEATURE:
<223> OTHER INFORMATION: Description of Artificial Sequence: Synthetic probe

<400> SEQUENCE: 34
gaagcacacg actgaggcac ctccagatgt 30

```
<210> SEQ ID NO 35
<211> LENGTH: 15
<212> TYPE: PRT
<213> ORGANISM: Artificial Sequence
<220> FEATURE:
<223> OTHER INFORMATION: Description of Artificial Sequence: Synthetic
      linker

<400> SEQUENCE: 35

Gly Gly Gly Gly Ser Gly Gly Gly Gly Ser Gly Gly Gly Gly Ser
  1               5                  10                  15


<210> SEQ ID NO 36
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Phe Lys Tyr Lys
  1


<210> SEQ ID NO 37
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Lys(DTPA)
<220> FEATURE:
<221> NAME/KEY: MOD_RES
<222> LOCATION: (3)
<223> OTHER INFORMATION: Lys(DTPA)
<220> FEATURE:
<221> NAME/KEY: MOD_RES
<222> LOCATION: (4)
<223> OTHER INFORMATION: Lys(Tscg-Cys); Cys not part of peptide backbone
<220> FEATURE:
<223> OTHER INFORMATION: c-term amidated

<400> SEQUENCE: 37

Lys Tyr Lys Lys
  1


<210> SEQ ID NO 38
<211> LENGTH: 149
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38

ggctcaccgg tgtaggtgtt tatccagccc atccactcta aaccctgtcc tggagcctgt      60

ctcacccagt tcattccata gtttctgaag gtatacccag aagccttgca ggagaccttg     120

acgctagatc caggcttctt gacctcagc                                       149


<210> SEQ ID NO 39
<211> LENGTH: 149
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 39

tcgaggctac taccgttgaa atccatccat ccctttcttg cacagaaata gaaagccgtg     60

tcctcagatc tcaagctaga cagctccata taggcagtgt tggtagattc gtcggctgtg    120

aaggcaaacc gtcccttgaa gtcatcagc                                      149


<210> SEQ ID NO 40
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40

ccaactgcag cagtctggag ctgaggtcaa gaagcct                              37


<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41

ggctcaccgg tgtaggtgtt                                                 20


<210> SEQ ID NO 42
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42

acctacaccg gtgagccaac atatgctgat gacttcaagg gacg                      44


<210> SEQ ID NO 43
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43

ggtgaccggg gtcccttggc cccagtagtc gaggctacta ccgttga                   47


<210> SEQ ID NO 44
<211> LENGTH: 140
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44

gaaactttgt agatcagcag ctttggagcc ttacctggct tctgctggta ccattctaaa     60

taggtgtttc cattactatg tacaatgctc tgactggatc tacaagagat ggacactctg    120
```

tcacccacgc tggcgctcag 140

<210> SEQ ID NO 45
<211> LENGTH: 131
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 45
ggtcccgccg ccgaacgtcg gaggaacatg tgaaccttga aagcagtagt aggtggcgat 60
gtcctctggc tggaggctgc tgatggtgaa ggtgaagtcg gtaccgctac cgctaccgct 120
gaatctgtct g 131

<210> SEQ ID NO 46
<211> LENGTH: 41
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 46
cagctgaccc agagcccaag cagcctgagc gccagcgtgg g 41

<210> SEQ ID NO 47
<211> LENGTH: 43
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 47
ctggcactcc ggaaaatcgg ttggaaactt tgtagatcag cag 43

<210> SEQ ID NO 48
<211> LENGTH: 37
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 48
caaccgattt tccggagtgc cagacagatt cagcggt 37

<210> SEQ ID NO 49
<211> LENGTH: 33
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 49
gatctccacc ttggtcccgc cgccgaacgt cgg 33

<210> SEQ ID NO 50
<211> LENGTH: 13
<212> TYPE: DNA
<213> ORGANISM: Artificial Sequence
<220> FEATURE:
<223> OTHER INFORMATION: Description of Artificial Sequence: Synthetic linker -continued

```
<400> SEQUENCE: 50

agcttgcggc cgc                                                       13


<210> SEQ ID NO 51
<211> LENGTH: 13
<212> TYPE: DNA
<213> ORGANISM: Artificial Sequence
<220> FEATURE:
<223> OTHER INFORMATION: Description of Artificial Sequence: Synthetic
      linker

<400> SEQUENCE: 51

gatcgcggcc gca                                                       13
```

CHIMERIC, HUMAN AND HUMANIZED ANTI-GRANULOCYTE ANTIBODIES AND METHODS OF USE

CLAIM FOR PRIORITY

The present application is a non-provisional application of U.S. Provisional Patent Application Ser. No. 60/414,341, the entire contents of which are hereby incorporated by reference.

BACKGROUND OF THE INVENTION

1. Field of the Invention

The present invention relates to humanized, chimeric and human anti-granulocyte antibodies, particularly monoclonal antibodies (MAbs), therapeutic and diagnostic conjugates of humanized, chimeric and human anti-granulocyte antibodies and methods of diagnosing or treating a malignancy, inflammation, atherosclerosis, infarction or other diseases manifesting an increased presence of activated granulocytes, using humanized, chimeric and fully human anti-granulocyte antibodies. Preferred anti-granulocyte antibodies are those binding the NCA90 and NCA95 antigens, such as the MN3 monoclonal antibody against NCA90, the Mabs MN-2, MN-15, NP-1, NP-2, BW 250/183 against NCA95, Mab 47, and antibodies directed to antigens present on a single granulocyte precursor, such as anti-CD-15 and anti-CD-33, or a combination thereof. The present invention also relates to antibody fusion proteins or fragments thereof comprising at least two anti-granulocyte MAbs or fragments thereof or at least one anti-granulocyte MAb or fragment thereof and at least one second MAb or fragment thereof, other than the anti-granulocyte MAb or fragment thereof. The humanized, chimeric and human anti-granulocyte MAbs, fragments thereof, antibody fusion proteins thereof or fragments thereof may be administered alone, as a therapeutic conjugate or in combination with a therapeutic immunoconjugate, with other naked antibodies, or with therapeutic agents or as a diagnostic conjugate. The present invention further relates to DNA sequences encoding humanized, chimeric and human MN3 antibodies against NCA 90, and antibody fusion proteins, vectors and host cells containing the DNA sequences, and methods of making the humanized, chimeric and human MN3 antibodies.

The invention relates to immunological reagents for therapeutic use, for example, in radioimmunotherapy (RAIT) and chemoimmunotherapy, and detection and/or diagnostic uses, for example, in radioimmunodetection (RAID), ultrasonography, and magnetic resonance imaging (MRI). In particular, the invention relates to naked antibodies (unconjugated) and directly-conjugated antibodies, as well as bi-specific antibodies (bsAbs) and bi-specific antibody fragments (bsFabs) which have at least one arm which is reactive against a targeted tissue and at least one other arm which is reactive against a linker moiety. Further, the invention relates to monoclonal antibodies that have been raised against specific immunogens, being human, humanized and chimeric monoclonal antibodies, as well as human, humanized and chimeric bi-specific antibodies and antibody fragments having at least one arm which is reactive against a targeted tissue or cell type and at least one other arm which is reactive against a linker moiety, DNAs that encode such antibodies and antibody fragments, and vectors for expressing the DNAs.

2. Background

Monoclonal antibodies (MAbs) have wide diagnostic and therapeutic potentials in clinical practices against cancer and other diseases. Early clinical trials revealed encouraging results using radiolabeled MAbs for the diagnosis/detection (radioimmunodetection: RAID) and treatment (radioimmunotherapy: RAIT) of malignancies in cancer patients (Goldenberg et al., (1993) (*Intl. J. Oncol.* 3:5-11; Goldenberg et al., (1995) *Immunol. Today* 16:261-264; Goldenberg (1993) *Am. J. Med.* 94:297-312; Goldenberg (1991) *Adv. Exp. Med. Biol.,* 303:107-117). Monoclonal antibodies play a central role in cancer immunotherapy, either in naked forms, or as conjugates to cytotoxic agents, such as radioisotopes, drugs, toxins, or prodrug-converting enzymes (Goldenberg et al., (1993) *Immunol. Today,* 14:5-7). These approaches are under active evaluation, with different levels of developmental and clinical successes. Naked MAbs potentially may achieve clinical responses by inducing a cytotoxic effect upon binding to cell surface proteins that are over-expressed on cancer cells. Studies have shown that these therapeutic effects were accomplished by controlling tumor growth via programmed cell death (apoptosis), or by the induction of anti-tumor immune responses (Cragg et al., (1999) *Curr. Opin. Immunol.,* 11:541-547).

The majority of clinically interesting antibodies were raised in mice. The problem of immunogenicity of murine MAbs in humans has been the major obstacle preventing their clinical application, especially in cancer therapy where large doses and repeated administrations are required to achieve maximum efficacy. It has been demonstrated that significant human-anti-mouse antibody (HAMA) responses were detected in approximately 50% of patients after a single injection of murine MAb; greater than 90% of patients developed HAMA following two or three repeated injections (Sears et al., (1984) *J. Biol. Response Med.* 3:138-150; Reynolds et al., (1989) *Int. J. Rad. Appl. Instrum. B,* 16:121-125; Shawler et al. (1985) *J. Immunol.,* 135:1530-1535; Jaffers et al., (1986) *Transplantation,* 41:572-578). In addition, the therapeutic effects of these murine MAbs in humans, if any, are further mitigated with their short serum half-lives and inabilities to recruit human effector cells, such as complement-fixing cytotoxic T cells. With the advent of molecular engineering, we can now genetically modify the structure of an antibody without affecting its antigen specificity to minimize or eliminate the HAMA responses and simultaneously enhance its immune effector functions. The processes are called chimerization and humanization. These modified MAbs have been shown to possess attributes essential for enhanced clinical utility, i.e., decreased immunogenicities, longer serum half-lives in human, and the ability to recruit effector functions.

Granulocytes, including neutrophils, basophils and eosinophils, are white blood cells that help mediate the humoral immune response. Granulocytes play an important role in defense of the host organism by migrating to sites of infection or injury and initiating phagocytosis and production of inflammatory mediators. One consequence of this activity is acute inflammation that can cause damage to the surrounding tissue. Abnormal granulocytes production, proliferation and/or dedifferentiation can also result in myeloid leukemia.

Inflammation has also been implicated as a major contributing factor in cystic fibrosis. See Konstan, M. W. et al., Infection and Inflammation in the Lung in Cystic Fibrosis, in Cystic Fibrosis, Davis, P. B. (ed.), Marcel Dekker, Inc., NY (1993). The inflammatory response to this infection is excessive and persistent. It sets the stage for a vicious cycle of airway obstruction, infection, and inflammation that ultimately leads to lung destruction. See Davis, P. B. et al. Am. J. Respir. Crit. Care Med. 154:1229-1256 (1996) and Konstan, M. W. et al., Pediatr. Pulmonol. 24:137-142 (1997). The inflammatory component of CF is characterized by persistent infiltration of neutrophils, which includes times of clinical stability. See Konstan, M. W. et al., Am. J. Respir. Crit. Care Med. 150:448-454 (1994). This occurs very early in the course of the disease for many patients, frequently during the first year of life, and may exist even in the absence of apparent infection. See Konstan, M. W. et al., Pediatr. Pulmonol. 24:137-142 (1997). Further, in acute myocardial infarction, particularly resulting from compromised blood flow (ischemia because of vessel compromise), insipidation of granulocytes into the diseased myocardium results and plays a prominent role in the tissue damage and infarction resulting from ischemia of the myocardium. In this situation, it has now been discovered that an antibody targeting such activated granulocytes not only can assist in the diagnosis of extent of ischemic disease, but can in fact interrupt the progression of infarction and tissue necrosis by binding to the pathology-inducing, activated granulocytes.

Accordingly, there remains a need for imaging granulocyte populations and their localization to determine sites of inflammation. There also remains a need for effective therapies of granulocyte disorders like myeloid leukemias, as well as preventing progression of myocardial infarction following myocardial ischemia.

SUMMARY OF THE INVENTION

The present invention provides a monoclonal antibody (MAb) or fragment thereof that binds granulocyte (neutrophil) antigen. Preferably, the present invention provides humanized, chimeric and human anti-granulocyte-targeting antibodies, such as MN3 antibodies, which are useful for the treatment and diagnosis of a malignancy and of diseases resulting from the accumulation in tissue of activated granulocytes, such as in ischemic injury.

The present invention also provides a humanized MN3 (hMN3) monoclonal antibody (MAb) or fragment thereof comprising one or more complementarity-determining regions (CDRs) of a murine MN3 MAb and one or more framework (FR) regions of the light and heavy chain variable regions of a human antibody and the light and heavy chain constant regions of a human antibody. The CDRs of the light chain variable region of the humanized can be selected from a MN3 MAb CDR1 comprising amino acids RSSQSIVHSNGNTYLE (SEQ ID NO: 1); a CDR2 comprising an amino acid sequence of KVSNRFS (SEQ ID NO: 2); and a CDR3 comprising an amino acid sequence of FQGSHVPPT (SEQ ID NO: 3). The CDRs of the heavy chain variable region of the MN3 MAb can be selected from a CDR1 comprising amino acids NYGMN (SEQ ID NO: 4); a CDR2 comprising amino acids WINTYTGEPTYADDFKG (SEQ ID NO: 5); and a CDR3 comprising amino acids KGWMDFNGSSLDY (SEQ ID NO: 6).

The invention further provides a humanized antibody molecule comprising a variable domain wherein the complementarity determining regions (CDRs) of said variable domain are from the mouse monoclonal MN3 antibody and the remainder of the immunoglobulin is from one or more human immunoglobulins.

Also provided by the present invention is a humanized antibody heavy chain comprising a variable domain wherein the CDRs of said variable domain are from the mouse monoclonal antibody MN3 heavy chain and the remainder of the immunoglobulin is from the heavy chain of one or more human immunoglobulins.

Also provided by the present invention is a CDR-grafted humanized heavy chain comprising the complementarity determining regions (CDRs) of a murine MN3 MAb and the framework region of the heavy chain variable region of a human antibody and the heavy chain constant region of a human antibody, wherein the CDRs of the heavy chain variable region of the humanized MN3 MAb comprises CDR1 comprising an amino acid sequence of NYGMN (SEQ ID NO: 4); CDR2 comprising an amino acid sequence of WINTYTGEPTYADDFKG (SEQ ID NO: 5) and CDR3 comprising an amino acid sequence of KGWMDFNGSSLDY (SEQ ID NO: 6).

A CDR-grafted humanized light chain comprising the complementarity determining regions (CDRs) of a murine MN3 MAb and the framework region of the light chain variable region of a human antibody and the light chain constant region of a human antibody, wherein the CDRs of the light chain variable region of the humanized MN3 MAb comprises CDR1 comprising an amino acid sequence of RSSQSIVHSNGNTYLE (SEQ ID NO: 1); CDR2 comprising an amino acid sequence of KVSNRFS (SEQ ID NO: 2)and CDR3 comprising an amino acid sequence of FQGSHVPPT (SEQ ID NO: 3).

If the humanized antibody molecule is a CDR-grafted humanized antibody molecule, appropriate variable region framework sequences may be used having regard to class/type of the donor antibody from which the antigen binding regions are derived. Preferably the type of human framework used is of the same/similar class/type as the donor antibody. Advantageously the framework is chosen to maximise/optimize homology with the donor antibody sequence particularly at positions specially close or adjacent to the CDRs. Examples of human frameworks which may be used to construct CDR-grafted antibodies are LAY, POM, TUR, TEI, KOL, NEWM, REI and EU; for instance KOL and NEWM for the heavy chain and REI for the light chain or EU for both the heavy chain and light chain.

In another embodiment, the humanized MN3 antibody or fragment thereof comprises at least one amino acid substituted from the corresponding position of the FR of the murine MN3 antibody or fragment thereof. Preferably, the murine amino acid from the murine MN3 MAb or fragment thereof is at least one amino acid selected from the group consisting of amino acid residue 27, 30, 67, 68, 69 or 94 of the murine heavy chain variable region as numbered in FIG. 4B. Also preferred, the murine amino acid from the murine MN3 MAb or fragment thereof is at least one amino acid selected from the group consisting of amino acid residue 20, 22, 39, 60, 70 or 100 of the murine light chain variable region shown in FIG. 4A.

In a preferred embodiment, the MN3 fragments of the present invention are selected from the group consisting of Fv, $F(ab')_2$, Fab' and Fab, as well as scFv and related single-chain, antigen-binding, constructs.

The invention also provides a humanized MN3 MAb or fragment thereof comprising the hMN3Vk of FIG. 4B and/or the hMN3VH1 of FIG. 4A.

Further provided is a chimeric MN3 (cMN3) monoclonal antibody, or fragment thereof comprising the complementarity-determining regions (CDRs) of a murine MN3 MAb and the framework (FR) regions of the light and heavy chain variable regions of said murine anti-CD 20 MAb and the light and heavy chain constant regions of a human antibody, wherein the CDRs of the light chain variable region of the chimeric MN3 MAb comprises CDR1 comprising an amino acid sequence RSSQSIVHSNGNTYLE (SEQ ID NO: 1); CDR2 comprising an amino acid sequence of KVSNRFS; and CDR3 comprise an amino acid sequence of FQGSHVPPT (SEQ ID NO: 2); and the CDRs of the heavy chain variable region of the MN3 MAb comprise CDR1 comprising amino acids NYGMN (SEQ ID NO: 4); CDR2 comprising amino acids WINTYTGEPTYADDFKG (SEQ ID NO: 5) and CDR3 comprising amino acids KGWMDFNGSSLDY (SEQ ID NO: 6).

The invention further provides a chimeric MN3 (cMN3) monoclonal antibody (MAb) or fragment thereof comprising the light and heavy chain variable regions of murine MN3 MAb and the light and heavy chain constant regions of a human antibody, wherein said cMN3 comprises the light chain variable region as set forth in FIG. 4B designated as cMN3Vk and the heavy chain variable region set forth in FIG. 4A designated as cMN3VH.

The invention also provides a human MN3 (MN3) monoclonal antibody (MAb) or fragment thereof comprising the light and heavy chain variable and constant regions of a human antibody, wherein the CDRs of the light chain variable region of the human MN3 MAb comprises CDR1 comprising an amino acid sequence RSSQSIVHSNGNTYLE (SEQ ID NO: 1); CDR2 comprising an amino acid sequence of KVSNRFS (SEQ ID NO: 2); and CDR3 comprise an amino acid sequence of FQGSHVPPT (SEQ ID NO: 3); and the CDRs of the heavy chain variable region of the MN3 MAb comprise CDR1 comprising amino acids NYGMN (SEQ ID NO: 4); CDR2 comprising amino acids WINTYTGEPTYADDFKG (SEQ ID NO: 5) and CDR3 comprising amino acids KGWMDFNGSSLDY (SEQ ID NO: 6).

The invention further provides a method for the expression of an MN3 MAb or fragment thereof or antibody fusion protein or fragment thereof.

The invention also provides a multivalent, multispecific antibody or fragment thereof comprising one or more antigen binding sites having affinity toward an antigen recognized by MN3 and one or more binding sites having affinity towards hapten molecules.

Also contemplated herein is a diagnostic/detection or therapeutic immunoconjugate comprising an antibody component that comprises any of the MN3 MAbs or fragments thereof of the present invention, or an antibody fusion protein or fragment thereof that comprises any of the MN3 antibodies or fragments thereof of the present invention, wherein the antibody component is bound to at least one diagnostic/detection agent or at least one therapeutic agent. Similarly, any anti-granulocyte antibody performing similar targeting functions, such as an NCA95, a CD33, a CD15, or other such antibodies can be used as described for the anti-NCA90 MAb, MN3. Preferably, the diagnostic/detection or therapeutic agent of the immunoconjugate according to the present invention is bound to said MAb or fragment thereof by means of a carbohydrate moiety.

In some embodiments, the present compositions and methods are useful for diagnosing or detecting granulocyte disorders, such as myeloid leukemias and inflammation, including that caused by myocardial ischemia, cystic fibrosis, appendicitis, inflammatory bowel disease and pelvic inflammatory disease. The present methods can also be used to diagnose or detect space-occupying lesions of the bone marrow, where a negative uptake or image of the bone marrow using the present antibodies and fragments indicates the presence of the lesion. Detection of bone marrow lesions can be useful in determining if a metastatic cancer, such as a prostate, lung or breast cancer, has infiltrated the bone marrow. The diagnosis or detection methods can be particularly useful for patients known or suspected of having such disorders, inflammation or malignancy.

In one embodiment, the diagnostic/detection immunoconjugate comprises at least one photoactive diagnostic/detection agent, such as a chromagen or dye at least one radionuclide with an energy between 20 and 10,000 keV, such as a gamma-, beta- or a positron-emitting isotope, a contrast agent, such as a radiopaque compound, a paramagnetic ion, including chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and erbium (III), or an ultrasound-enhancing agent, including a liposome that is conjugated to a humanized anti-granulocyte antibody or fragment thereof. The liposome can be gas-filled. The radiopaque compound may be selected from the group consisting of iodine compounds, barium compounds, gallium compounds and thallium compounds. In another embodiment, the diagnostic/detection described herein is used in intraoperative, endoscopic, or intravascular detection/diagnosis.

Also contemplated herein is a therapeutic immunoconjugate comprising a therapeutic agent that is selected from the group consisting of a radionuclide, boron, gadolinium or uranium atoms, an immunomodulator, such as a cytokine, a stem cell growth factor, a lymphotoxin, such as tumor necrosis factor (TNF), a hematopoietic factor such as an interleukin (IL), a colony stimulating factor (CSF) such as granulocyte-colony stimulating factor (G-CSF) or granulocyte macrophage-colony stimulating factor (GM-CSF)), an interferon (IFN) such as interferons-$\alpha$, -$\beta$ or -$\gamma$, and a stem cell growth factor such as that designated "S1 factor," a hematopoietic factor, erythropoietin, thrombopoietin, an antibody, a hormone, a hormone antagonist, an enzyme, an enzyme inhibitor, a photoactive therapeutic agent, a cytotoxic drug, such as antimitotic, alkylating, antimetabolite, angiogenesis-inhibiting, apoptotic, alkaloid, COX-2-inhibiting and antibiotic agents, a cytotoxic toxin, such as plant, microbial, and animal toxins, and a synthetic variations thereof, an angiogenesis inhibitor, a different antibody and a combination thereof. In a preferred embodiment, the cytokine is selected from the group consisting of IL-1, IL-2, IL-3, IL-6, IL-10, IL-12, IL-18, IL-21, interferon-$\gamma$, TNF-$\alpha$ and a combination thereof, the radionuclide is selected from the group consisting of an Auger emitter, a beta-emitter and an alpha-emitter, such as P-32, P-33, Sc-47, Fe-59, Cu-64, Cu-67, Se-75, As-77, Sr-89, Y-90, Mo-99, Rh-105, Pd-109, Ag-111, I-125, I-131, Pr-142, Pr-143, Pm-149, Sm-153, Tb-161, Ho-166, Er-169, Lu-177, Re-186, Re-188, Re-189, Ir-194, Au-198, Au-199, Pb-211, Pb-212, and Bi-213, Co-58, Ga-67, Br-80m, Tc-99m, Rh-103m, Pt-109, In-111, Sb-119, I-125, Ho-161, Os-189m, Ir-192, Dy-152, At-211, Bi-212, Ra-223, Rn-219, Po-215, Bi-211, Ac-225, Fr-221, At-217, Bi-213, Fm-255, B-10, Gd-157, U-235, and combinations thereof. Preferably, the radionuclide has an energy between 20 and 10,000 keV.

In another embodiment, the therapeutic agent conjugated to the anti-granulocyte antibody or fragment thereof is a photoactive therapeutic agent, such as a chromogen or dye.

Considered in the present invention also is a multivalent, multispecific antibody or fragment thereof comprising one or more antigen-binding sites having affinity toward an antigen recognized by the anti-granulocyte antibody and one or more hapten binding sites having affinity towards hapten. Preferably, the anti-granulocyte antibody antibody or fragment thereof is humanized. Also preferred, the antibody or fragment thereof is fully human or chimerized. In one embodiment, the multivalent, multispecific antibody or fragment thereof comprises a diagnostic/detection or therapeutic agent.

Also considered in the present invention is an antibody fusion protein or fragment thereof comprising at least two anti-granulocyte MAbs or fragments thereof, wherein the MAbs or fragments thereof are selected from any of the NCA90, NCA95, CD33, or CD15 monoclonal antibodies or fragments thereof of the present invention. In a similar vein, an antibody fusion protein or fragment thereof comprising at least one first anti-granulocyte MAb or fragment thereof of any one the anti-granulocyte antibodies or fragments of the present invention, and at least one second MAb or fragment thereof, other than any one of the first anti-granulocyte MAbs or fragments thereof of the present invention, is also contemplated. In a preferred embodiment, the second MAb is another, but different granulocyte-associated antibody. In another preferred embodiment, the antibody fusion protein or fragment thereof further comprises a diagnostic/detection or therapeutic agent conjugated to the fusion protein or fragment thereof.

Considered herein is a method of treating a malignancy or other disease involving accumulation of activated or neoplastic granulocytes in a subject, comprising the step of administering to said subject a therapeutically effective amount of a naked and/or conjugated anti-granulocyte antibody, fusion protein, or fragment thereof of the present invention, formulated in a pharmaceutically acceptable vehicle, either alone or in combination with other therapeutic and/or diagnostic agents. Preferably, a method of treating a malignancy in a subject, comprising the step of administering to said subject a therapeutically effective amount of an immunoconjugate or fragment thereof the present invention, formulated in a pharmaceutically acceptable vehicle.

Similarly, a method of diagnosing/detecting a malignancy or other granulocyte-related disease in a subject, comprising the step of administering to said subject a diagnostically effective amount of a naked or conjugated anti-granulocyte antibody, fusion protein, or fragment thereof of the present invention, optionally formulated in a pharmaceutically acceptable vehicle. These methods can further involve the step of detecting whether the anti-granulocyte antibody binds to the target antigen.

Yet another embodiment of the present invention provides a method for the ablation of bone marrow comprising administering to a subject one or more of the antibodies or fragments described herein coupled to a bone marrow ablation agent.

Another embodiment is a method of treating or diagnosing/detecting a malignancy in a subject, comprising (i) administering to a subject in need thereof the anti-granulocyte antibody or fragments thereof of the present invention; (ii) waiting a sufficient amount of time for a desired amount of the non-binding protein to clear the subject's bloodstream; and (iii) administering to said subject a carrier molecule comprising a diagnostic agent, a therapeutic agent, or a combination thereof, that binds to a binding site of said antibody.

The present compositions also include nucleic acids encoding the disclosed antibodies to NCA90 (MN3), such as those shown in the figures, vectors containing these nucleic acids and cells containing the nucleic acids. The present invention also provides methods for producing the MN3 Mabs disclosed herein using the nucleic acids, vectors and transfected cells.

Another embodiment of the present invention is a DNA sequence and a vector comprising a DNA sequence, and a host cell comprising a DNA sequence, that comprises a nucleic acid encoding an MN3 MAb or fragment thereof selected from the group consisting (a) an MN3 MAb or fragment thereof of the present invention; (b) an antibody fusion protein or fragment thereof comprising at least two of said MAbs or fragments thereof; (c) an antibody fusion protein or fragment thereof comprising at least one first MN3 MAb or fragment thereof comprising said MAb or fragment thereof of any one of the antibodies of the present invention and at least one second MAb or fragment thereof, other than the MN3 MAb or fragment thereof described in the present invention; and (d) an antibody fusion protein or fragment thereof comprising at least one first MAb or fragment thereof comprising said MAb or fragment thereof of any one of the antibodies of the present invention and at least one second MAb or fragment thereof, other than the MN3 MAb or fragment thereof of any one of the antibodies of the present invention, wherein said second MAb is selected from the group consisting of anti-NCA-90, anti-NCA-95, MN-2, MN-3, MN-15, NP-1, NP-2, BW 250/183, and MAb 47 and antibodies directed to antigens present on a single granulocyte precursor, such as anti-CD-15 and anti-CD-33, or a combination thereof.

A method of delivering a diagnostic/detection or therapeutic agent, or a combination thereof, to a target comprising (i) providing a composition comprising an immunoconjugate that comprises the antibody, fusion protein, or fragment thereof of any one of the antibodies, fusion proteins, or fragments thereof of the present invention and (ii) administering to a subject in need thereof said composition, is also described. Preferably, the diagnostic/detection agent comprises at least one photoactive diagnostic agent, such as a chromogen or dye, a contrast agent, such as a paramagnetic ion, an ultrasound-enhancing agent or a radiopaque compound used in X-rays or computed tomography, such as an iodine compound, barium compound, gallium compound or thallium compound. In one embodiment, the ultrasound-enhancing agent is a liposome that comprises a humanized anti-granulocyte antibody or fragment thereof, and optionally, the liposome is gas-filled. In another embodiment, the diagnostic/detection agent preferably is a radionuclide with an energy between 20 and 2,000 keV, such as a gamma-, beta- or a positron-emitting isotope. Still preferred, the radionuclide is selected from the group consisting of F-18, Mn-51, Mn-52m, Fe-52, Co-55, Cu-62, Cu-64, Ga-68, As-72, Br-75, Br-76, Rb-82m, Sr-83, Y-86, Zr-89, Tc-94m, In-110, I-120, I-124, Cr-51, Co-57, Co-58, Fe-59, Cu-67, Ga-67, Se-75, Ru-97, Tc-99m, In-111, In-114m, I-123, I-125, I-131, Yb-169, Hg-197, and Tl-201. Also preferred, the radiopaque compound is selected from the group consisting of barium, diatrizoate, ethiodized oil, gallium citrate, iocarmic acid, iocetamic acid, iodamide, iodipamide, iodoxamic acid, iogulamide, iohexol, iopamidol, iopanoic acid, ioprocemic acid, iosefamic acid, ioseric acid, iosulamide meglumine, iosemetic acid, iotasul, iotetric acid, iothalamic acid, iotroxic acid, ioxaglic acid, ioxotrizoic acid, ipodate, meglumine, metrizamide, metrizoate, propyliodone, and thallous chloride.

Similarly, in the method of delivering a diagnostic/detection or therapeutic agent, or a combination thereof, to a target, the therapeutic agent is preferably selected from the group consisting of a radionuclide, an immunomodulator, a hormone, a hormone antagonist, an enzyme, an enzyme inhibitor, a photoactive therapeutic agent, a cytotoxic agent, such as a drug or toxin (including a plant, microbial and animal toxin, and a synthetic variation thereof), and a combination thereof. Preferably, the drug is selected from the group consisting of antimitotic, alkylating, antimetabolite, antiangiogenic, apoptotic, anthracyclines, alkaloid, COX-2-inhibitor and antibiotic agents, and combinations thereof, nitrogen mustards, ethylenimine derivatives, alkyl sulfonates, nitrosoureas, triazenes, folic acid analogs, anthracyclines, taxanes, pyrimidine analogs, purine analogs, antibiotics, enzymes, enzyme inhibitors, epipodophyllotoxins, platinum coordination complexes, vinca alkaloids, substituted ureas, methyl hydrazine derivatives, adrenocortical suppressants, hormones, hormone antagonists, endostatin, taxols, camptothecins, doxorubicins and their analogs, and a combination thereof. Also preferred, the toxin is selected from the group consisting of ricin, abrin, alpha toxin, saporin, ribonuclease (RNase), DNase I, Staphylococcal enterotoxin-A, pokeweed antiviral protein, gelonin, diphtherin toxin, *Pseudomonas* exotoxin, and *Pseudomonas* endotoxin. Suitable enzymes include malate dehydrogenase, staphylococcal nuclease, delta-V-steroid isomerase, yeast alcohol dehydrogenase, α-glycerophosphate dehydrogenase, triose phosphate isomerase, horseradish peroxidase, alkaline phosphatase, asparaginase, glucose oxidase, β-galactosidase, ribonuclease, urease, catalase, glucose-6-phosphate dehydrogenase, glucoamylase and acetylcholinesterase.

Also considered herein is a method of delivering a diagnostic/detection agent, a therapeutic agent, or a combination thereof to a target, comprising: (i) administering to a subject a multivalent, multispecific antibody or fragment thereof of the present invention; (ii) waiting a sufficient amount of time for an amount of the non-binding protein to clear the subject's blood stream; and (iii) administering to said subject a carrier molecule comprising a diagnostic/detection agent, a therapeutic agent, or a combination thereof, that binds to a binding site of said antibody. Preferably, the multivalent, multispecific antibody or fragment thereof comprises one or more antigen-binding sites having affinity toward an antigen recognized by MN3 and one or more hapten binding sites having an affinity towards hapten molecules. Preferably, the carrier molecule binds to more than one binding site of the antibody. Also preferred, the diagnostic/detection agent or said therapeutic agent is selected from the group comprising isotopes, dyes, chromogens, contrast agents, drugs, toxins, cytokines, enzymes, enzyme inhibitors, hormones, hormone antagonists, growth factors, radionuclides, and metals.

Contemplated herein is a method of treating a malignancy or another granulocyte-associated disease in a subject comprising administering to said subject a therapeutically effective amount of (i) an antibody or fragment thereof or (ii) an antibody fusion protein or fragment thereof, wherein the antibody or fragment thereof comprises at least two MAbs or fragments thereof, at least one of which is any of the anti-granulocyte MAbs or fragments thereof of the present invention, and the fusion protein or fragment thereof comprises at least one an binding site for an antigen recognized by the anti-granulocyte MAb, formulated in a pharmaceutically suitable excipient. In a preferred embodiment, at least one of the Mabs or fragments thereof is a naked Mab or fragment thereof. In another embodiment, the fusion protein comprises a second binding site that is reactive with a tumor marker substance or a granulocyte target antigen other than an antigen recognized by the first antibody. Also contemplated is that the anti-granulocyte antibody or fragment thereof, or anti-granulocyte MAb fusion protein or fragment thereof, is administered before, concurrently, or after at least one therapeutic or diagnostic/detection agent.

Another embodiment is a method of treating a malignancy or a granulocyte-related disease in a subject comprising administering to said subject a therapeutically effective amount of an antibody or fragment thereof comprising at least two MAbs or fragments thereof, wherein the MAbs are selected from any one of the anti-granulocyte antibodies described herein, and formulated in a pharmaceutically suitable excipient. In a preferred embodiment, at least one of the Mabs or fragments thereof is a naked Mab or fragment thereof. Also contemplated is that the anti-granulocyte antibody or fragment thereof, or the anti-granulocyte fusion protein or fragment thereof, is administered before, concurrently, or after at least one therapeutic and/or diagnostic/detection agent.

In the method of treatment described herein, the MN3 antibody is selected from a chimeric MN3 antibody, human MN3 antibody, and humanized MN3 antibody. Preferably, the chimeric, human and humanized MN3 antibody constant and hinge regions comprise constant and hinge regions of a human IgG1. Also in the methods described herein, the MN3 antibody or fragment thereof or fusion protein or fragment thereof is administered before, in conjunction with, or after a second conjugated antibody reactive with a second tumor marker or an activated granulocyte antigen target expressed by said malignancy or granulocyte-associated disease, respectively, is administered to said subject.

The present invention also describes a method of diagnosing or detecting a malignancy or an ischemic lesion in a subject comprising administering to said subject a diagnostically effective amount of a diagnostic/detecting conjugate comprising a MN3 MAb or fragment thereof or a fusion protein or fragment thereof of as described in the present invention, wherein the MN3 MAb or fragment thereof, or fusion protein or fragment thereof, is bound to at least one diagnostic/detection agent, formulated in a pharmaceutically suitable excipient.

Another embodiment of the present invention is a method of treating a malignant myeloid cell population or an ischemic injury in a subject comprising (i) administering to said subject a therapeutically effective amount of a composition comprising a naked or conjugated anti-granulocyte MAb or fragment thereof or a naked or conjugated antibody fusion protein or fragment thereof, as described in the present invention, and (ii) optionally formulating said anti-granulocyte MAb or fragment thereof or antibody fusion protein or fragment thereof in a pharmaceutically suitable excipient. Preferably, the anti-granulocyte antibody, fusion protein, or fragment thereof is an MN3 antibody, fusion protein, or fragment thereof. Optionally, the composition may further comprise a second naked or conjugated antibody or fragment thereof, or naked or conjugated antibody fusion protein or fragment thereof, that may or be an MN3 antibody, fusion protein or fragment thereof, or may bind a second marker expressed by the malignancy or ischemic lesion. Also considered is that the anti-granulocyte antibody, antibody fusion protein, or fragment thereof, is administered before, in conjunction with, or after a second antibody, fusion protein, or fragment thereof is administered to said subject. The anti-granulocyte antibody may also be administered before, concurrently or after a therapeutic or diagnostic/detection agent.

The present invention also describes a method of diagnosing or detecting a malignancy in a subject comprising (i) performing an in vitro diagnosis assay on a specimen from the subject with a composition comprising an anti-granulocyte MAb or fragment thereof or an antibody fusion protein or fragment thereof described herein. Preferably the malignancy is a granulocyte, e.g. a neutrophil, expressing an antigen recognized, for example, by MN3, such as a myeloid leukemia. Also preferred, the in vitro diagnosis assay is selected from the group consisting of immunoassays, RT-PCR and immunohistochemistry. If the diagnostic assay is RT-PCR or immunoassays, the specimen is preferably body fluid or a tissue or cell population. If the diagnostic assay is immunohistochemistry or immunocytochemistry, the specimen is preferably a cell aliquot or a tissue.

In any of the methods of the present invention, the subject is preferably a mammal, such as a human or domestic pet.

Another embodiment of the present invention is a method of treating or identifying diseased tissues in a subject, comprising: (A) administering to said subject a bi-specific antibody or antibody fragment having at least one arm that specifically binds a diseased tissue-associated marker and at least one other arm that specifically binds a targetable conjugate, wherein said diseased tissue-associated marker is an antigen recognized by the anti-granulocyte MAb; (B) optionally, administering to said subject a clearing composition, and allowing said composition to clear non-localized antibodies or antibody fragments from circulation; (C) administering to said subject a first targetable conjugate which comprises a carrier portion which comprises or bears at least one epitope recognizable by said at least one other arm of said bi-specific antibody or antibody fragment, and one or more conjugated therapeutic or diagnostic agents; and (D) when said therapeutic agent is an enzyme, further administering to said subject (i) a prodrug, when said enzyme is capable of converting said prodrug to a drug at the target site; or (ii) a drug which is capable of being detoxified in said subject to form an intermediate of lower toxicity, when said enzyme is capable of reconverting said detoxified intermediate to a toxic form, and, therefore, of increasing the toxicity of said drug at the target site, or (iii) a prodrug which is activated in said subject through natural processes and is subject to detoxification by conversion to an intermediate of lower toxicity, when said enzyme is capable of reconverting said detoxified intermediate to a toxic form, and, therefore, of increasing the toxicity of said drug at the target site, or (iv) a second targetable conjugate which comprises a carrier portion which comprises or bears at least one epitope recognizable by said at least one other arm of said bi-specific antibody or antibody fragment, and a prodrug, when said enzyme is capable of converting said prodrug to a drug at the target site. Preferably, at least one arm that specifically binds a targeted tissue is a human, chimeric or humanized anti-granulocyte antibody or a fragment of a human, chimeric or humanized anti-granulocyte antibody. Also preferred, the targetable conjugate comprises at least two HSG (histamine-succinyl-glycine) haptens. Preferably, the targeted tissue is a tumor or ischemic lesion with an accumulation of granulocytes, and more preferably, the tumor or ischemia produces or is associated with an antigen recognized by the anti-granulocyte antibody. Also preferred, the anti-granulocyte antibody or fragment thereof comprises the Fv of the MAb. A preferred embodiment is the use of the MN3 MAb in such applications as a chimeric, humanized, or human antibody, as described herein.

This method may further comprise, when said first targetable conjugate comprises a prodrug, administering a second targetable conjugate which comprises a carrier portion which comprises or bears at least one epitope recognizable by said at least one other arm of said bi-specific antibody or antibody fragment, and an enzyme capable of converting said prodrug to a drug or of reconverting a detoxified intermediate of said drug to a toxic form. Preferably, the prodrug is selected from the group consisting of epirubicin glucuronide, CPT-11, etoposide glucuronide, daunomicin glucuronide and doxorubicin glucuronide. Also preferred, the targetable conjugate comprises one or more radioactive isotopes useful for killing diseased tissue. The targetable conjugate may comprise one or more agents for photodynamic therapy, such as a photosensitizer. In a preferred embodiment, the photosensitizer is selected from the group consisting of benzoporphyrin monoacid ring A (BPD-MA), tin etiopurpurin (SnET2), sulfonated aluminum phthalocyanine (AlSPc) and lutetium texaphyrin (Lutex).

Considered herein is a method for detecting or treating tumors or ischemic lesions expressing an antigen recognized by an anti-granulocyte MAb in a mammal, comprising: (A) administering an effective amount of a bispecific antibody or antibody fragment comprising at least one arm that specifically binds a targeted tissue and at least one other arm that specifically binds a targetable conjugate, wherein said one arm that specifically binds a targeted tissue is an anti-granulocyte antibody or fragment thereof; and (B) administering a targetable conjugate. The targetable conjugate can be selected from the group consisting of (i) DOTA-Phe-Lys(HSG)-D-Tyr-Lys(HSG)-$NH_2$; (ii) DOTA-Phe-Lys(HSG)-Tyr-Lys(HSG)-$NH_2$(SEQ ID NO: 7); (iii) Ac-Lys(HSG)D-Tyr-Lys(HSG)-Lys(Tscg-Cys)-$NH_2$; (iv) DOTA-D-Asp-D-Lys(HSG)-D-Asp-D-Lys(HSG)-$NH_2$; (v) DOTA-D-Glu-D-Lys(HSG)-D-Glu-D-Lys(HSG)-$NH_2$; (vi) DOTA-D-Tyr-D-Lys(HSG)-D-Glu-D-Lys(HSG)-$NH_2$; (vii) DOTA-D-Ala-D-Lys(HSG)-D-Glu-D-Lys(HSG)-$NH_2$; (viii) DOTA-D-Phe-D-Lys(HSG)-D-Tyr-D-Lys(HSG)-$NH_2$; (ix) Ac-D-Phe-D-Lys(DOTA)-D-Tyr-D-Lys(DOTA)-$NH_2$; (x) Ac-D-Phe-D-Lys(DTPA)-D-Tyr-D-Lys(DTPA)-$NH_2$; (xi) Ac-D-Phe-D-Lys(Bz-DTPA)-D-Tyr-D-Lys(Bz-DTPA)-$NH_2$; (xii) Ac-D-Lys(HSG)-D-Tyr-D-Lys(HSG)-D-Lys(Tscg-Cys)-$NH_2$; (xiii) DOTA-D-Phe-D-Lys(HSG)-D-Tyr-D-Lys(HSG)-D-Lys(Tscg-Cys)-$NH_2$; (xiv) (Tscg-Cys)-D-Phe-D-Lys(HSG)-D-Tyr-D-Lys(HSG)-D-Lys(DOTA)-$NH_2$; (xv) Tscg-D-Cys-D-Glu-D-Lys(HSG)-D-Glu-D-Lys(HSG)-$NH_2$; (xvi) (Tscg-Cys)-D-Glu-D-Lys(HSG)-D-Glu-D-Lys(HSG)-$NH_2$; (xvii) Ac-D-Cys-D-Lys(DOTA)-D-Tyr-D-Ala-D-Lys(DOTA)-D-Cys-$NH_2$; (xviii) Ac-D-Cys-D-Lys(DTPA)-D-Tyr-D-Lys(DTPA)-$NH_2$; (xix) Ac-D-Lys(DTPA)-D-Tyr-D-Lys(DTPA)-D-Lys(TscG-Cys)-$NH_2$; (xx) Ac-D-Lys(DOTA)-D-Tyr-D-Lys(DOTA)-D-Lys(TscG-Cys)-$NH_2$;

(xxi)

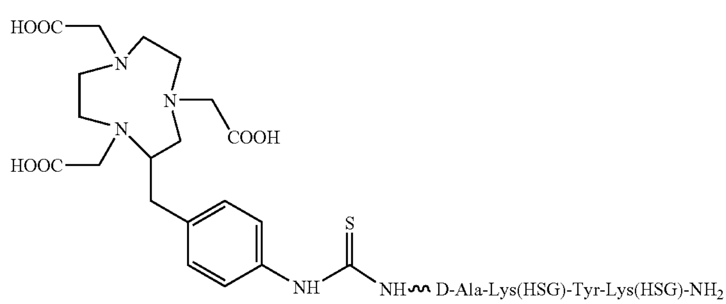

-continued (xxii)

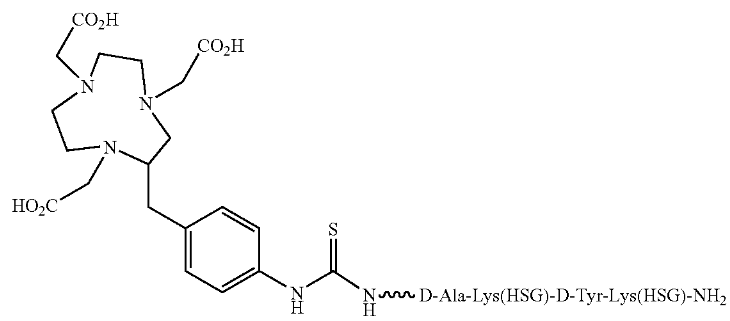

(xxiii)

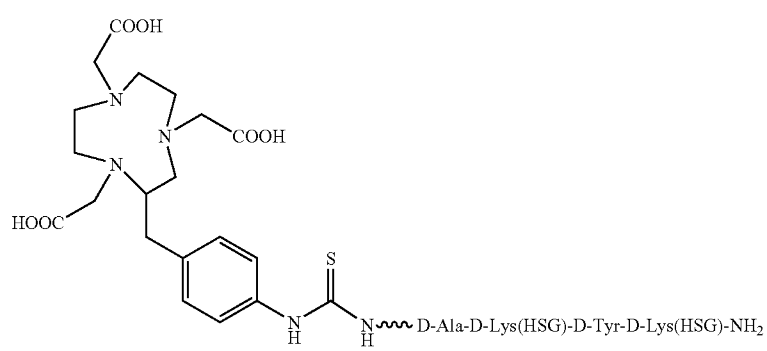

Additional targetable conjugates that can be used with the present methods include those disclosed in U.S. Patent Application No. 60/478,403.

Preferably, the method further comprises administering to the subject a clearing composition, and allowing said composition to increase clearance of non-localized antibodies or antibody fragments from circulation.

Also contemplated herein is a kit useful for treating or identifying diseased tissues involving accumulation of normal or malignant granulocytes in a subject comprising: (A) a bi-specific antibody or antibody fragment having at least one arm that specifically binds a targeted tissue and at least one other arm that specifically binds a targetable conjugate, wherein said one arm that specifically binds a targeted tissue is an anti-granulocyte antibody or fragment thereof; (B) a first targetable conjugate which comprises a carrier portion which comprises or bears at least one epitope recognizable by said at least one other arm of said bi-specific antibody or antibody fragment, and one or more conjugated therapeutic or diagnostic agents; and (C) optionally, a clearing composition useful for clearing non-localized antibodies and antibody fragments; and (D) optionally, when said therapeutic agent conjugated to said first targetable conjugate is an enzyme, (i) a prodrug, when said enzyme is capable of converting said prodrug to a drug at the target site; or (ii) a drug which is capable of being detoxified in said subject to form an intermediate of lower toxicity, when said enzyme is capable of reconverting said detoxified intermediate to a toxic form, and, therefore, of increasing the toxicity of said drug at the target site, or (iii) a prodrug which is activated in said subject through natural processes and is subject to detoxification by conversion to an intermediate of lower toxicity, when said enzyme is capable of reconverting said detoxified intermediate to a toxic form, and, therefore, of increasing the toxicity of said drug at the target site, or (iv) a second targetable conjugate which comprises a carrier portion which comprises or bears at least one epitope recognizable by said at least one other arm of said bi-specific antibody or antibody fragment, and a prodrug, when said enzyme is capable of converting said prodrug to a drug at the target site. Preferably, the targetable conjugate is selected from the group consisting of:

(i) DOTA-Phe-Lys(HSG)-D-Tyr-Lys(HSG)-$NH_2$; (ii) DOTA-Phe-Lys(HSG)-Tyr-Lys(HSG)-$NH_2$; (SEQ ID NO: 7) (iii) Ac-Lys(HSG)D-Tyr-Lys(HSG)-Lys(Tscg-Cys)-$NH_2$; (iv) DOTA-D-Asp-D-Lys(HSG)-D-Asp-D-Lys(HSG)-$NH_2$; (v) DOTA-D-Glu-D-Lys(HSG)-D-Glu-D-Lys(HSG)-$NH_2$; (vi) DOTA-D-Tyr-D-Lys(HSG)-D-Glu-D-Lys(HSG)-$NH_2$; (vii) DOTA-D-Ala-D-Lys(HSG)-D-Glu-D-Lys(HSG)-$NH_2$; (viii) DOTA-D-Phe-D-Lys(HSG)-D-Tyr-D-Lys(HSG)-$NH_2$; (ix) Ac-D-Phe-D-Lys(DOTA)-D-Tyr-D-Lys(DOTA)-$NH_2$; (x) Ac-D-Phe-D-Lys(DTPA)-D-Tyr-D-Lys(DTPA)-$NH_2$; (xi) Ac-D-Phe-D-Lys(Bz-DTPA)-D-Tyr-D-Lys(Bz-DTPA)-$NH_2$; (xii) Ac-D-Lys(HSG)-D-Tyr-D-Lys(HSG)-D-Lys(Tscg-Cys)-$NH_2$; (xiii) DOTA-D-Phe-D-Lys(HSG)-D-Tyr-D-Lys(HSG)-D-Lys(Tscg-Cys)-$NH_2$; (xiv) (Tscg-Cys)-D-Phe-D-Lys(HSG)-D-Tyr-D-Lys(HSG) -D-Lys(DOTA)-$NH_2$; (xv) Tscg-D-Cys-D-Glu-D-Lys(HSG)-D-Glu-D-Lys(HSG)-$NH_2$; (xvi) (Tscg-Cys)-D-Glu-D-Lys(HSG)-D-Glu-D-Lys(HSG)-$NH_2$; (xvii) Ac-D-Cys-D-Lys(DOTA)-D -Tyr-D-Ala-D-Lys(DOTA)-D-Cys-$NH_2$; (xviii) Ac-D-Cys-D-Lys(DTPA)-D-Tyr-D-Lys(DTPA) -$NH_2$; (xix) Ac-D-Lys(DTPA)-D-Tyr-D-Lys(DTPA)-D-Lys(TscG-Cys)-$NH_2$; (xx) Ac-D -Lys(DOTA)-D-Tyr-D-Lys(DOTA)-D-Lys(TscG-Cys)-$NH_2$;

(xxi)

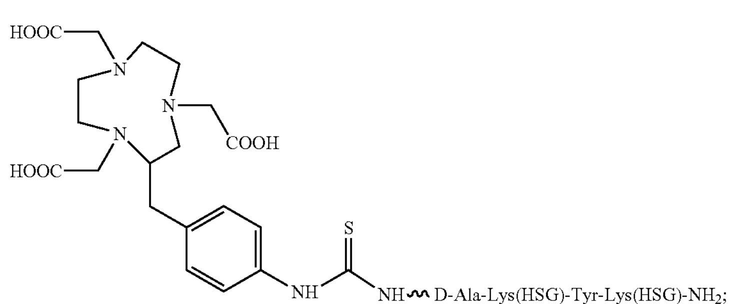

(xxii)

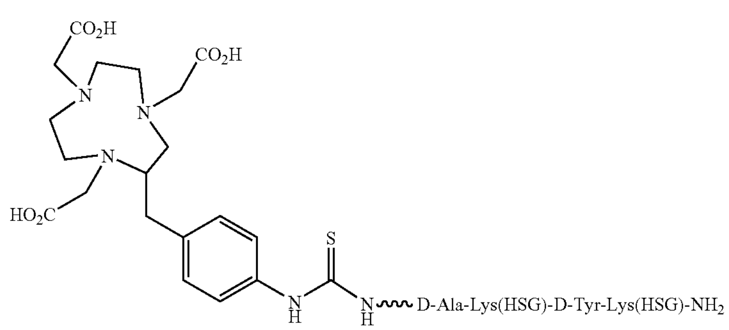

(xxiii)

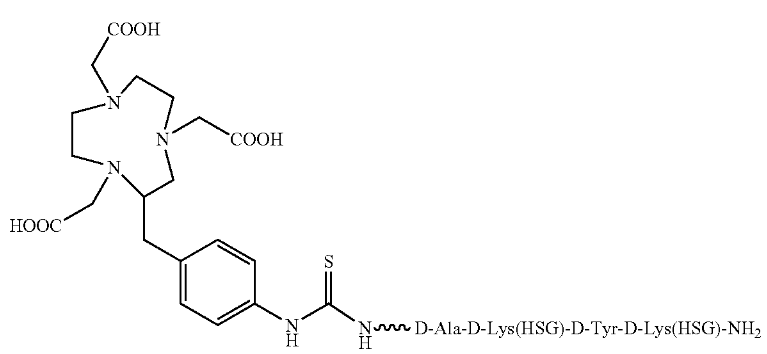

Also described in the present invention is a method of screening for a targetable conjugate comprising: (A) contacting said targetable construct with a bi-specific antibody or antibody fragment having at least one arm that specifically binds a marker associated with a targeted tissue, wherein said marker is an antigen recognized by MN3, and at least one other arm that specifically binds said targetable conjugate to give a mixture; and (B) optionally incubating the mixture; and (C) analyzing the mixture.

Another embodiment is a method for imaging malignant or ischemic tissue or cells in a mammal expressing an antigen recognized by an anti-granulocyte MAb, comprising: (A) administering an effective amount of a bispecific antibody or antibody fragment comprising at least one arm that specifically binds a marker associated with a targeted tissue and at least one other arm that specifically binds a targetable conjugate, wherein said marker is an antigen recognized by the anti-granulocyte MAb; and (B) administering a targetable conjugate selected from the group consisting of (i) DOTA-Phe-Lys(HSG)-D-Tyr-Lys(HSG)-$NH_2$; (ii) DOTA-Phe-Lys(HSG)-Tyr-Lys(HSG) -$NH_2$; (SEQ ID NO: 7) (iii) Ac-Lys(HSG)D-Tyr-Lys(HSG)-Lys(Tscg-Cys)-$NH_2$; (iv) DOTA-D -Asp-D-Lys(HSG)-D-Asp-D-Lys(HSG)-$NH_2$; (v) DOTA-D-Glu-D-Lys(HSG)-D-Glu-D -Lys(HSG)-$NH_2$; (vi) DOTA-D-Tyr-D-Lys(HSG)-D-Glu-D-Lys(HSG)-$NH_2$; (vii) DOTA-D-Ala-D -Lys(HSG)-D-Glu-D-Lys(HSG)-$NH_2$; (viii) DOTA-D-Phe-D-Lys(HSG)-D-Tyr-D-Lys(HSG)-$NH_2$; (ix) Ac-D-Phe-D-Lys(DOTA)-D-Tyr-D-Lys(DOTA)-$NH_2$; (x) Ac-D-Phe-D-Lys(DTPA)-D-Tyr-D -Lys(DTPA)-$NH_2$; (xi) Ac-D-Phe-D-Lys(Bz-DTPA)-D-Tyr-D-Lys(Bz-DTPA)-$NH_2$; (xii) Ac-D -Lys(HSG)-D-Tyr-D-Lys(HSG)-D-Lys (Tscg-Cys)-$NH_2$; (xiii) DOTA-D-Phe-D-Lys(HSG)-D-Tyr -D-Lys(HSG)-D-Lys(Tscg-Cys)-$NH_2$; (xiv) (Tscg-Cys)-D-Phe-D-Lys(HSG)-D-Tyr-D-Lys(HSG) -D-Lys(DOTA)-$NH_2$; (xv) Tscg-D-Cys-D-Glu-D-Lys(HSG)-D-Glu-D-Lys(HSG)-$NH_2$; (xvi) (Tscg-Cys)-D-Glu-D-Lys(HSG)-D-Glu-D-Lys (HSG)-$NH_2$; (xvii) Ac-D-Cys-D-Lys(DOTA)-D -Tyr-D-Ala-D-Lys(DOTA)-D-Cys-$NH_2$; (xviii) Ac-D-Cys-D-Lys (DTPA)-D-Tyr-D-Lys(DTPA) -$NH_2$; (xix) Ac-D-Lys (DTPA)-D-Tyr-D-Lys(DTPA)-D-Lys(TscG-Cys)-$NH_2$; (xx) Ac-D -Lys(DOTA)-D-Tyr-D-Lys(DOTA)-D-Lys(TscG-Cys)-$NH_2$;

(xxi)

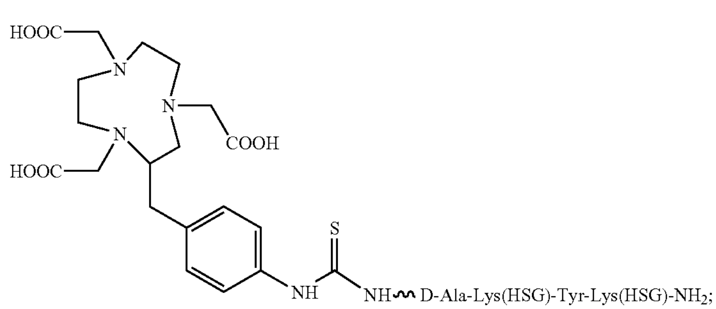

(xxii)

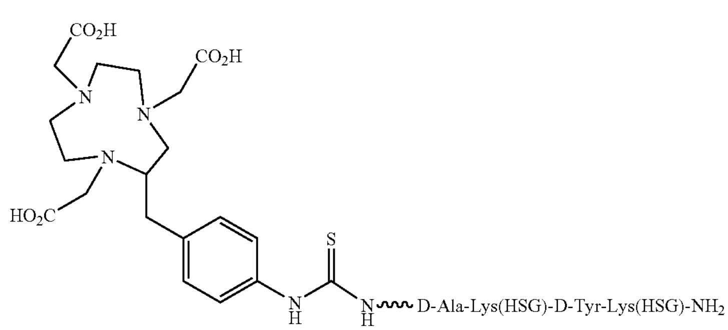

(xxiii)

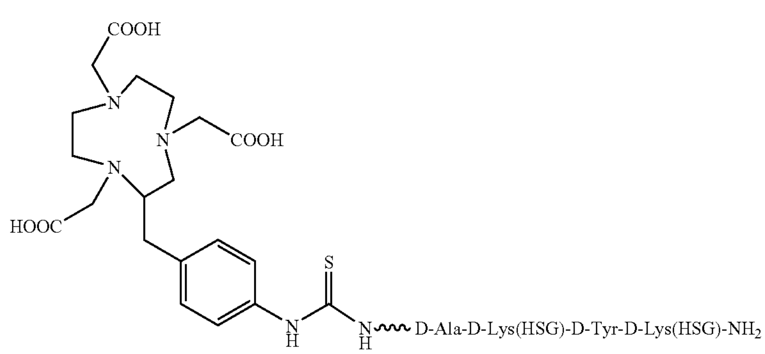

The invention also contemplates a method of intraoperatively identifying/disclosing diseased tissues expressing an antigen recognized by an anti-granulocyte MAb, in a subject, comprising: (A) administering an effective amount of a bispecific antibody or antibody fragment comprising at least one arm that specifically binds an antigen recognized by the anti-granulocyte MAb and at least one other arm that specifically binds a targetable conjugate, wherein said one arm that specifically binds a targeted tissue is an anti-granulocyte MAb antibody or fragment thereof; and (B) administering a targetable conjugate selected from the group consisting of (i) DOTA-Phe-Lys(HSG)-D-Tyr-Lys(HSG)-$NH_2$; (ii) DOTA-Phe-Lys(HSG)-Tyr-Lys(HSG) -$NH_2$; (SEQ ID NO: 7) (iii) Ac-Lys(HSG)D-Tyr-Lys(HSG)-Lys(Tscg-Cys)-$NH_2$; (iv) DOTA-D -Asp-D-Lys(HSG)-D-Asp-D-Lys(HSG)-$NH_2$; (v) DOTA-D-Glu-D-Lys(HSG)-D-Glu-D -Lys(HSG)-$NH_2$; (vi) DOTA-D-Tyr-D-Lys(HSG)-D-Glu-D-Lys(HSG)-$NH_2$; (vii) DOTA-D-Ala-D -Lys(HSG)-D-Glu-D-Lys(HSG)-$NH_2$; (viii) DOTA-D-Phe-D-Lys(HSG)-D-Tyr-D-Lys(HSG)-$NH_2$; (ix) Ac-D-Phe-D-Lys(DOTA)-D-Tyr-D-Lys(DOTA)-$NH_2$; (x) Ac-D-Phe-D-Lys(DTPA)-D-Tyr-D -Lys(DTPA)-$NH_2$; (xi) Ac-D-Phe-D-Lys(Bz-DTPA)-D-Tyr-D-Lys(Bz-DTPA)-$NH_2$; (xii) Ac-D -Lys(HSG)-D-Tyr-D-Lys(HSG)-D-Lys (Tscg-Cys)-$NH_2$; (xiii) DOTA-D-Phe-D-Lys(HSG)-D-Tyr -D-Lys(HSG)-D-Lys(Tscg-Cys)-$NH_2$; (xiv) (Tscg-Cys)-D-Phe-D-Lys(HSG)-D-Tyr-D-Lys(HSG) -D-Lys(DOTA)-$NH_2$; (xv) Tscg-D-Cys-D-Glu-D-Lys(HSG)-D-Glu-D-Lys(HSG)-$NH_2$; (xvi) (Tscg-Cys)-D-Glu-D-Lys(HSG)-D-Glu-D-Lys (HSG)-$NH_2$; (xvii) Ac-D-Cys-D-Lys(DOTA)-D -Tyr-D-Ala-D-Lys(DOTA)-D-Cys-$NH_2$; (xviii) Ac-D-Cys-D-Lys (DTPA)-D-Tyr-D-Lys(DTPA) -$NH_2$; (xix) Ac-D-Lys (DTPA)-D-Tyr-D-Lys(DTPA)-D-Lys(TscG-Cys)-$NH_2$; (xx) Ac-D -Lys(DOTA)-D-Tyr-D-Lys(DOTA)-D-Lys(TscG-Cys)-$NH_2$;

(xxi)

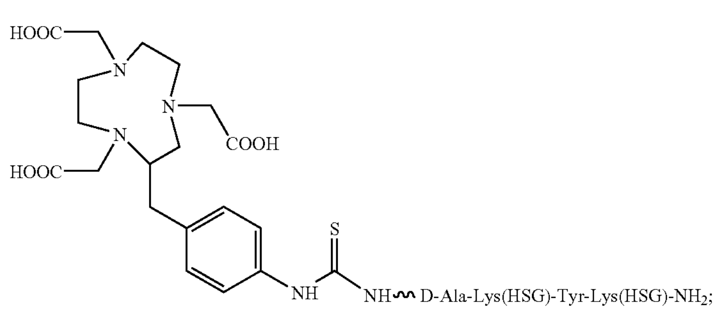

(xxii)

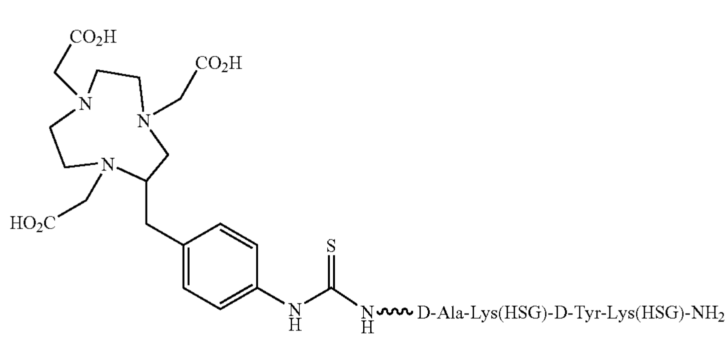

(xxiii)

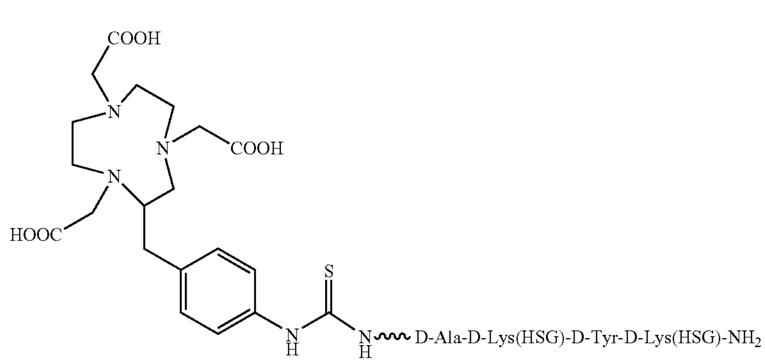

Also described herein is a method for the endoscopic identification of diseased tissues expressing an antigen recognized by an anti-granulocyte MAb, in a subject, comprising: (A) administering an effective amount of a bispecific antibody or antibody fragment comprising at least one arm that specifically binds an antigen recognized by an anti-granulocyte MAb and at least one other arm that specifically binds a targetable conjugate wherein said one arm that specifically binds a targeted tissue is a MN3 antibody or fragment thereof; and (B) administering a targetable conjugate selected from the group consisting of (i) DOTA-Phe-Lys(HSG)-D-Tyr-Lys(HSG)-$NH_2$; (ii) DOTA-Phe-Lys(HSG)-Tyr-Lys(HSG) -$NH_2$; (SEQ ID NO: 7) (iii) Ac-Lys(HSG)D-Tyr-Lys(HSG)-Lys(Tscg-Cys)-$NH_2$; (iv) DOTA-D -Asp-D-Lys(HSG)-D-Asp-D-Lys(HSG)-$NH_2$; (v) DOTA-D-Glu-D-Lys(HSG)-D-Glu-D-Lys(HSG)-$NH_2$; (vi) DOTA-D-Tyr-D-Lys(HSG)-D-Glu-D-Lys(HSG)-$NH_2$; (vii) DOTA-D-Ala-D -Lys(HSG)-D-Glu-D-Lys(HSG)-$NH_2$; (viii) DOTA-D-Phe-D-Lys(HSG)-D-Tyr-D-Lys(HSG)-$NH_2$; (ix) Ac-D-Phe-D-Lys(DOTA)-D-Tyr-D-Lys(DOTA)-$NH_2$; (x) Ac-D-Phe-D-Lys(DTPA)-D-Tyr-D -Lys(DTPA)-$NH_2$; (xi) Ac-D-Phe-D-Lys(Bz-DTPA)-D-Tyr-D-Lys(Bz-DTPA)-$NH_2$; (xii) Ac-D -Lys(HSG)-D-Tyr-D-Lys(HSG)-D-Lys (Tscg-Cys)-$NH_2$; (xiii) DOTA-D-Phe-D-Lys(HSG)-D-Tyr -D-Lys(HSG)-D-Lys(Tscg-Cys)-$NH_2$; (xiv) (Tscg-Cys)-D-Phe-D-Lys(HSG)-D-Tyr-D-Lys(HSG) -D-Lys(DOTA)-$NH_2$; (xv) Tscg-D-Cys-D-Glu-D-Lys(HSG)-D-Glu-D-Lys(HSG)-$NH_2$; (xvi) (Tscg-Cys)-D-Glu-D-Lys(HSG)-D-Glu-D-Lys (HSG)-$NH_2$; (xvii) Ac-D-Cys-D-Lys(DOTA)-D -Tyr-D-Ala-D-Lys(DOTA)-D-Cys-$NH_2$; (xviii) Ac-D-Cys-D-Lys (DTPA)-D-Tyr-D-Lys(DTPA) -$NH_2$; (xix) Ac-D-Lys (DTPA)-D-Tyr-D-Lys(DTPA)-D-Lys(TscG-Cys)-$NH_2$; (xx) Ac-D -Lys(DOTA)-D-Tyr-D-Lys(DOTA)-D-Lys(TscG-Cys)-$NH_2$;

(xxi)

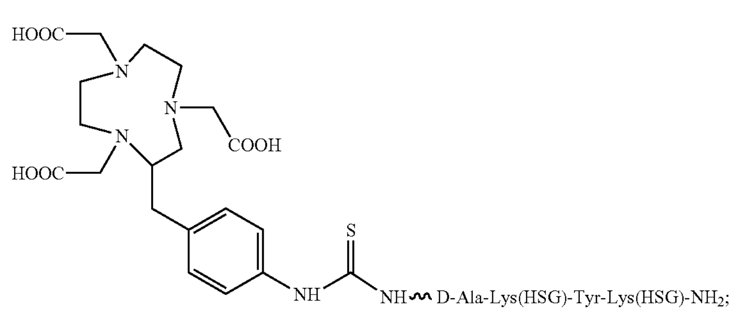

(xxii)

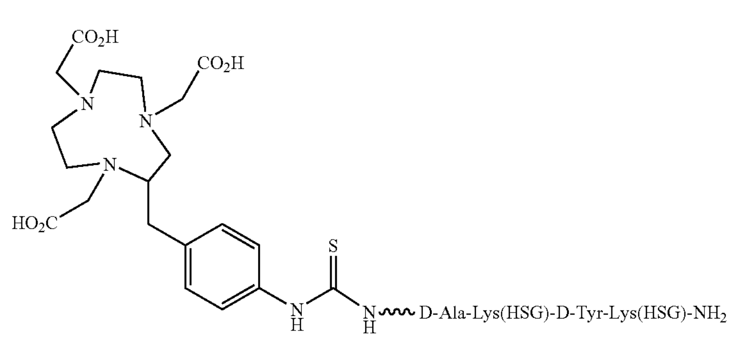

(xxiii)

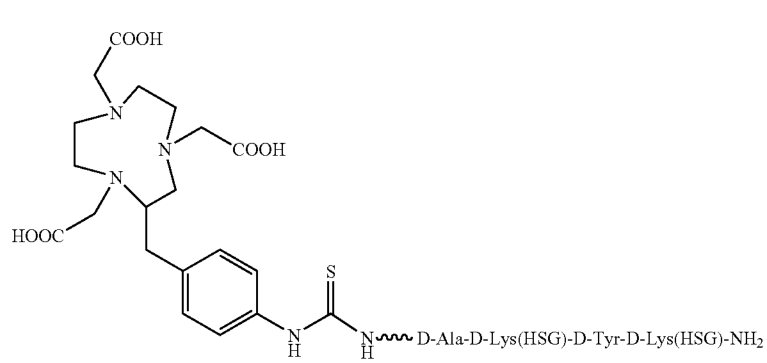

Another embodiment is a method for the intravascular identification of diseased tissues expressing an antigen recognized by an anti-granulocyte MAb, in a subject, comprising: (A) administering an effective amount of a bispecific antibody or antibody fragment comprising at least one arm that specifically binds an antigen recognized by the anti-granulocyte MAb and at least one other arm that specifically binds a targetable conjugate wherein said one arm that specifically binds a targeted tissue is a MN3 antibody or fragment thereof; and (B) administering a targetable conjugate selected from the group consisting of (i) DOTA-Phe-Lys(HSG)-D-Tyr-Lys(HSG)-$NH_2$; (ii) DOTA-Phe-Lys(HSG)-Tyr-Lys(HSG) -$NH_2$; (SEQ ID NO: 7) (iii) Ac-Lys(HSG)D-Tyr-Lys(HSG)-Lys(Tscg-Cys)-$NH_2$; (iv) DOTA-D -Asp-D-Lys(HSG)-D-Asp-D-Lys(HSG)-$NH_2$; (v) DOTA-D-Glu-D-Lys(HSG)-D-Glu-D -Lys(HSG)-$NH_2$; (vi) DOTA-D-Tyr-D-Lys(HSG)-D-Glu-D-Lys(HSG)-$NH_2$; (vii) DOTA-D-Ala-D -Lys(HSG)-D-Glu-D-Lys(HSG)-$NH_2$; (viii) DOTA-D-Phe-D-Lys(HSG)-D-Tyr-D-Lys(HSG)-$NH_2$; (ix) Ac-D-Phe-D-Lys(DOTA)-D-Tyr-D-Lys(DOTA)-$NH_2$; (x) Ac-D-Phe-D-Lys(DTPA)-D-Tyr-D -Lys(DTPA)-$NH_2$; (xi) Ac-D-Phe-D-Lys(Bz-DTPA)-D-Tyr-D-Lys(Bz-DTPA)-$NH_2$; (xii) Ac-D -Lys(HSG)-D-Tyr-D-Lys(HSG)-D-Lys (Tscg-Cys)-$NH_2$; (xiii) DOTA-D-Phe-D-Lys(HSG)-D-Tyr -D-Lys(HSG)-D-Lys(Tscg-Cys)-$NH_2$; (xiv) (Tscg-Cys)-D-Phe-D-Lys(HSG)-D-Tyr-D-Lys(HSG) -D-Lys(DOTA)-$NH_2$; (xv) Tscg-D-Cys-D-Glu-D-Lys(HSG)-D-Glu-D-Lys(HSG)-$NH_2$; (xvi) (Tscg-Cys)-D-Glu-D-Lys(HSG)-D-Glu-D-Lys (HSG)-$NH_2$; (xvii) Ac-D-Cys-D-Lys(DOTA)-D -Tyr-D-Ala-D-Lys(DOTA)-D-Cys-$NH_2$; (xviii) Ac-D-Cys-D-Lys (DTPA)-D-Tyr-D-Lys(DTPA) -$NH_2$; (xix) Ac-D-Lys (DTPA)-D-Tyr-D-Lys(DTPA)-D-Lys(TscG-Cys)-$NH_2$; (xx) Ac-D -Lys(DOTA)-D-Tyr-D-Lys(DOTA)-D-Lys(TscG-Cys)-$NH_2$;

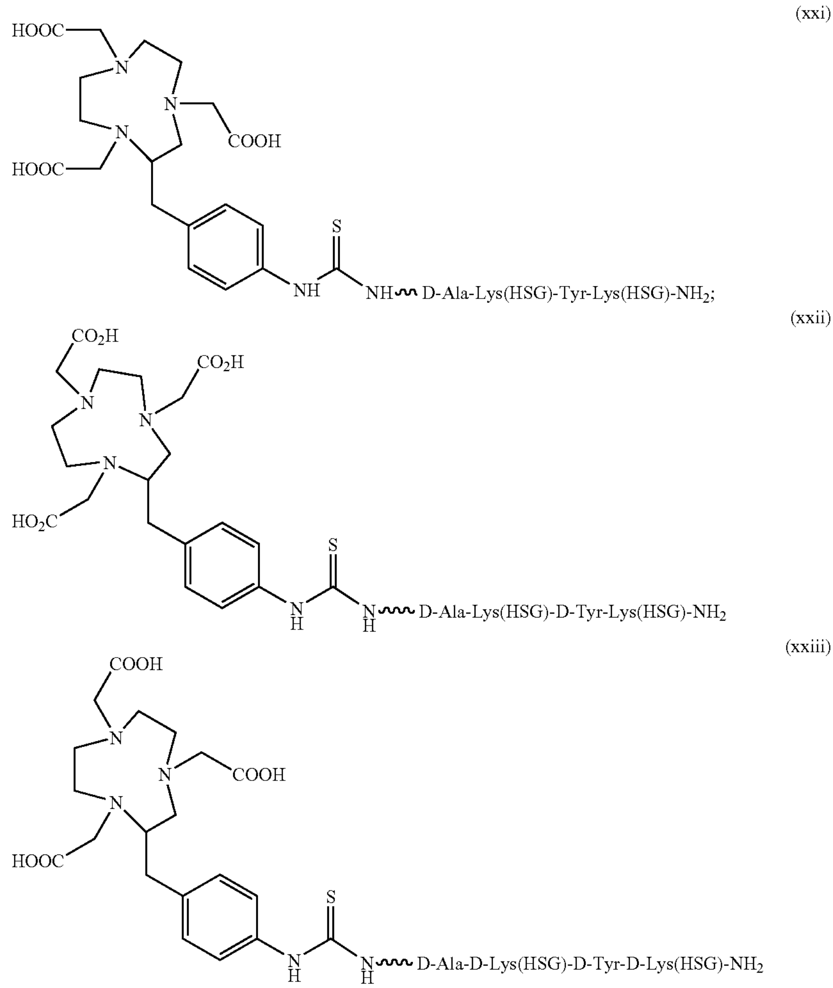

Another embodiment is a method of detecting lesions, preferably during an endoscopic, laparoscopic, intravascular catheter, or surgical procedure, wherein the method comprises: (A) injecting a subject who is to undergo such a procedure with a bispecific antibody $F(ab)_2$ or $F(ab')_2$ fragment, or single-chain Fv fragment, wherein the bispecific antibody or fragment has a first antibody binding site which specifically binds to an antigen recognized by an anti-granulocyte MAb antigen, and has a second antibody binding site which specifically binds to a hapten, and permitting the antibody fragment to accrete at target sites; (B) optionally clearing non-targeted antibody fragments using a galactosylated anti-idiotype clearing agent if the bispecific fragment is not largely cleared from circulation within about 24 hours of injection, and injecting a bivalent labeled hapten, which quickly localizes at the target site and clears through the kidneys; (C) detecting the presence of the hapten by close-range detection of elevated levels of accreted label at the target sites with detection means, within 48 hours of the first injection, and conducting said procedure, wherein said detection is performed without the use of a contrast agent or subtraction agent. In a preferred embodiment, the hapten is labeled with a diagnostic/detection radioisotope, a MRI image-enhancing agent, a fluorescent label or a chemiluminescent label. Fluorescent labels can include rhodamine, fluorescein, renographin, fluorescein isothiocyanate, phycoerytherin, phycocyanin, allophycocyanin, o-phthaldehyde and fluorescamine. Chemiluminescent labels can include luminol, isoluminol, an aromatic acridinium ester, an imidazole, an acridinium salt and an oxalate ester.

Also considered is a method for close-range lesion detection, preferably during an operative, intravascular, laparoscopic, or endoscopic procedure, wherein the method comprises: (A) injecting a subject to such a procedure parenterally with an effective amount of an anti-granulocyte MAb immunoconjugate or fragment thereof, (B) conducting the procedure within 48 hours of the injection; (C) scanning the accessed interior of the subject at close range with a detection means for detecting the presence of said labeled antibody or fragment thereof, and (D) locating the sites of accretion of said labeled antibody or fragment thereof by detecting elevated levels of said labeled antibody or fragment thereof at such sites with the detection means. Preferably, the anti-granulocyte MAb immunoconjugate or fragment thereof comprises a radioisotope that emits at an energy of 20-1,000 keV. Also preferred, the radioisotope is selected from the group consisting of technetium-99m, iodine-125, iodine-131, iodine-123, indium-111, fluorine-18, gallium-68 and gallium-67. In another embodiment, the anti-granulocyte MAb immunoconjugate or fragment thereof comprises a non-isotopic agent, such as a photoactive agent.

BRIEF DESCRIPTION OF THE FIGURES

FIG. 1 shows the cloned $V_H$ and Vκ gene sequences of the murine MN3 by RT-PCR and the deduced amino acid sequences. Underlined arrows at 5'- and 3'-ends indicate the sequence of PCR primers used in cloning. FIG. 1A shows the DNA (SEQ ID NO: 8) and amino acid (SEQ ID NO: 9) sequences of the MN3Vκ. FIG. 1B shows the DNA (SEQ ID NO: 10) and amino acid (SEQ ID NO: 11) sequences of the MN3$V_H$. Amino acid sequences encoded by the corresponding DNA sequences are given as one letter codes below the nucleotide sequence. Numbering of the nucleotide sequence is on the right side. The amino acid residues in the putative CDR regions are shown in bold and underlined. Kabat's Ig molecule numbering is used for amino acid residues as shown by the numbering above the amino acid residues. The residues numbered by a letter following digits indicate the insertion residues defined by Kabat numbering scheme. The insertion residues numbered with a letter only have the same preceding digits as the previous one. For example, residues 27A, 27B, 27C, 27D, and 27E in FIG. 1A are indicated as 82, A, B, and C27A, B, C, D, and E, respectively.

FIG. 2 shows the DNA and amino acid sequences of the chimeric MN3 (cMN3) heavy and light chain variable regions. FIG. 2A shows the DNA (SEQ ID NO: 12) and amino acid (SEQ ID NO: 13) sequences of the cMN3Vκ. FIG. 2B shows the DNA (SEQ ID NO: 14) and amino acid (SEQ ID NO: 15) sequences of the cMN3VH. Amino acid sequences encoded by the corresponding DNA sequences are given as one letter codes. The amino acid residues in the CDR regions are shown in bold and underlined. Numbering of the nucleotide sequence is on the right side. The numbering of amino acids is same as that in FIG. 1.

FIG. 4 shows the alignment of the amino acid sequences of light and heavy chain variable regions of certain human antibodies, MN3 and hMN3. FIG. 4A compares the amino acid sequences of the REI (SEQ ID NO: 16), MN3 (SEQ ID NO: 17) and hMN3 (SEQ ID NO: 18) light chain variable domains. FIG. 4B is the amino acid sequence alignment of EU (FR1-3) (SEQ ID NO: 19) and KOL (FR4) (SEQ ID NO: 22), MN3 (SEQ ID NO: 20) and hMN3 (SEQ ID NO: 21) heavy chain variable domains. Boxed regions represent the CDR regions. Dots indicate the residues in MN3 and hMN3 which are identical to the corresponding residues in REI Vκ. Dashes represent gaps introduced to aid the alignment. Both N- and C-terminal residues (underlined) of hMN3 are fixed by the staging vector used. The corresponding terminal residues of MN3 are not compared with that of the human sequences. Kabat's Ig molecule numbering scheme is used (same as in FIGS. 1A and 1B, respectively).

FIG. 5 discloses the nucleotide sequences of hMN3Vκ (SEQ ID NO: 23) and the adjacent flanking regions of the light chain staging vector, VKpBR2 (SEQ ID NO: 24) (FIG. 5A) and hMN3VH (SEQ ID NO: 25) and the adjacent flanking regions of the heavy chain staging vector, VKpBS2 (SEQ ID NO: 26) (FIG. 5B). The encoded amino acid sequences are shown as one letter codes below the corresponding DNA sequences. The non-translated nucleotide sequences are shown in lowercase. The restriction sites used for subcloning are underlined and indicated. The secretion signal peptide sequence is indicated by a double underline. Numbering of Vk and VH amino acid residues is the same as that in FIG. 2.

DETAILED DESCRIPTION OF THE INVENTION

1. Overview

Figure 3:
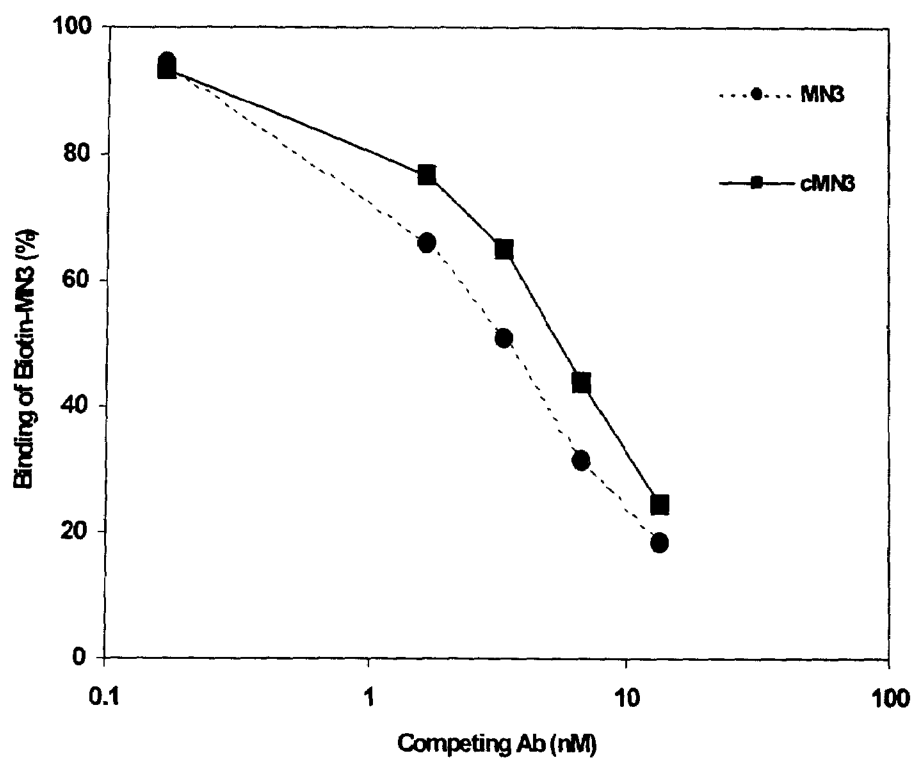
FIG. 3 shows the results of a competitive ELISA assay to compare the binding specificity and affinity of a chimeric MN3 (cMN3) with that of murine MN3 (mMN3). Varying concentrations of cMN3 (squares and solid line) or mMN3 (circles and dashed line) were mixed with a constant amount of biotinylated murine MN3 and incubated in microplate wells coated with CEA. The residual binding of the biotinylated MN3 was measured by HRP-conjugated streptavidin and substrate. The results showed that cMN3 and the murine MN3 were comparable in their binding target antigen.

The present invention provides murine, humanized, chimeric and human anti-granulocyte, e.g., anti-neutrophil (granulocyte) antibodies, fusion proteins, or fragments thereof useful for treatment and/or diagnosis of mammalian subjects, as an immunoconjugate or in combination with, but unconjugated to, other therapeutic and/or diagnostic agents. In a preferred embodiment, the anti-granulocyte antibody is an MN3 antibody. The MN3 antibodies and fragments thereof bind an antigen on granulocytes. In some embodiments, the antibody or fragment thereof is not a chimeric mouse-human antigranulocyte monoclonal antibody, such as is described by Sarwar et al., Radiat. Med. 16(5):391-7 (1998) or an antibody described by Zhao et al., J. Immunol. Methods, 270 (1):27-35 (2002).

A preferred example of such an antibody is MN-3. See Hansen et al., Cancer 71:3478-3485 (1993); Becker et al., Semin. Nucl. Med. 24(2):142-53 (1994).

The MN-3 antibody was isolated from hybridomas derived from BALB/c mice which were immunized with partially purified carcinoembryonic antigen (CEA) derived from GW-39 human colon adenocarcinoma xenografts. See Hansen et al., Cancer 71:3478-3485 (1993). The MN-3 antibody is specific for the NCA-90 antigen, a homotypic adhesion molecule expressed on granulocytes, as well as normal colonic mucosa and colonic adenocarcinoma. See Becker et al., Semin. Nucl. Med. 24(2):142-53 (1994); Watt et al., Blood 78:63-74 (1991).

Suitable amounts of the NCA-90 antigen, also referred to as CD66c, can be obtained using standard techniques well-known in the art. For example, NCA-90 protein can be obtained from transfected cultured cells that overproduce NCA-90. Expression vectors that comprise DNA molecules encoding NCA-90 can be constructed using the published NCA-90 nucleotide sequence. See Oikawa et al., Biochem. Biophys. Res. Commun. 146:464-460 (1987); Wilson et al., J. Exp. Med. 173:137 (1991); Wilson et al., J. Immunol. 150: 5013 (1993).

A variety of anti-granulocyte antibodies directed to antigens associated with various cell-types of the granulocyte/neutrophil can be used in the present invention. In one embodiment, the inventive methods utilize anti-NCA-90 antibodies. In another embodiment, anti-NCA-95 antibodies, anti-CD-33, or anti-CD-15 antibodies are used. See Thakur et al., J. Nucl. Med., 37:1789-95 (1996); Ball et al., J. Immunol., 30:2937-41 (1983); PCT WO 02/12347, incorporated in their entirety herein by reference. In still other embodiments, MN-2 and NP-2, which are class IIA anti-CEA antibodies, and MN-15 and NP-1, which are class I anti-CEA antibodies, are utilized. See Hansen et al., Cancer 71:3478-3485 (1993); Primus et al., Cancer Res. 43:686-692 (1983). Furthermore, BW 250/183 (a murine anti-NCA-95 antibody), and MAb 47 can be utilized. See Bosslet et al., Int. J. Cancer, 36:75-84 (1985); Meller et al., J. Nucl. Med. 39:1248-1253 and Audette et al., Mol. Immunol. 24:1177-1186 (1987). Human and chimeric forms of these antibodies are preferred, and full-human and humanized versions are most preferred. Subhuman primate antibodies and murine monoclonal antibodies may also be utilized. Constructs of multispecific and/or multivalent scFv constructs are also suitable for this invention.

Another suitable antibody is the MN-2 monoclonal antibody. The MN-2 antibody was isolated from hybridomas derived from BALB/c mice which were immunized with partially purified carcinoembryonic antigen (CEA) derived from GW-39 human colon adenocarcinoma xenografts. See Hansen et al., Cancer 71:3478-3485 (1993). As a class IIA anti-CEA antibody, MN-2 can be identified readily using blocking assays well-known in the art. See U.S. Pat. No. 4,818,709, which is hereby incorporated by reference in its entirety.

Another suitable antibody is the MN-15 monoclonal antibody. The MN-15 antibody displays cross-reactivity between NCA-90 and NCA-95. MN-15 was isolated from hybridomas derived from BALB/c mice which were immunized with partially purified carcinoembryonic antigen (CEA) derived from GW-39 human colon adenocarcinoma xenografts. See Hansen et al., Cancer 71:3478-3485 (1993). As a class I anti-CEA antibody, MN-15 can be identified readily using blocking assays well-known in the art.

Still another suitable antibody is the NP-2 monoclonal antibody. The NP-2 has specificity similar to that of MN-2. NP-2 was isolated from hybridomas derived from BALB/c mice which were immunized with partially purified carcinoembryonic antigen (CEA) derived from liver metastases of human colonic adenocarcinoma according to the procedure of Krupey et al. (Immunochem. 9: 617 (1972)), as modified by Newman et al. (Cancer Res. 34:2125 (1974)). See Primus et al., Cancer Res. 43:686-92 (1983); U.S. Pat. No. 4,818,709.

Yet another suitable antibody is the NP-1 monoclonal antibody. The NP-1 has similar specificity to that of MN-15. NP-1 was isolated from hybridomas derived from BALB/c mice which were immunized with partially purified carcinoembryonic antigen (CEA) derived from liver metastases of human colonic adenocarcinoma according to the procedure of Krupey et al. (Immunochem. 9:617 (1972)), as modified by Newman et al. (Cancer Res. 34:2125 (1974)). See Primus et al., Cancer Res., 43:686-92 (1983); U.S. Pat. No. 4,818,709.

The MN3 antibodies, fusion proteins, and fragments thereof of the present invention may also be administered with another conjugated or unconjugated MN3 antibody, fusion protein, or fragment thereof, or a conjugated or unconjugated non-MN3 antibody, fusion protein, or fragment thereof.

The chimeric or humanized MN3 MAbs and fragments thereof of the present invention contain specific murine CDRs or a combination of murine CDRs from more than one murine or chimeric MN3 MAb. Preferably, the chimeric and humanized MN3 antibodies of the present invention contain CDRs from a murine MN3 antibody. The MN3 Mabs and fragments thereof of the present invention are murine, humanized, chimeric or fully human Mabs. The chimeric and humanized antibodies contain the amino acid sequence of the CDRs of a murine MN3 (mMN3) MAb and the light and heavy chain constant regions of a human antibody.

In a preferred embodiment, the humanized MN3 MAb or fragment thereof of the present invention comprises the CDRs of a murine MN3 MAb and the framework (FR) regions of the light and heavy chain variable regions of a human antibody and the light and heavy chain constant regions of a human antibody. Preferably, the CDRs of the light chain variable region of the humanized MN3 MAb comprise a CDR1 that comprises an amino acid sequence of RSSQSIVHSNGNTYLE (SEQ ID NO: 1), CDR2 that comprises an amino acid sequence of KVSNRFS (SEQ ID NO: 2), and/or CDR3 that comprises an amino acid sequence of FQGSHVPPT (SEQ ID NO: 3); and the CDRs of the heavy chain variable region of the MN3 MAb comprise a CDR1 that comprises an amino acid sequence of NYGMN (SEQ ID NO: 4), a CDR2 that comprises an amino acid sequence of WINTYTGEPTYADDFKG (SEQ ID NO: 5), and/or a CDR3 that comprises an amino acid sequence of KGWMDFNGSSLDY (SEQ ID NO: 6).

In another embodiment, the humanized MN3 MAb or fragment thereof may further contain in the FRs of the light and heavy chain variable regions of the hMN3 antibody, at least one amino acid from the corresponding FRs of the murine MAb. In one embodiment, the humanized MN3 MAb or fragment thereof contains at least one amino acid residue 27, 30, 67, 68, 69 or 94 of the murine heavy chain variable region, for example as shown in the figures, and/or of at least one amino acid residue 20, 22, 39, 60, 70 or 100 of the murine light chain variable region, such as those shown in the figures. One or more of the murine amino acid sequences can be maintained in the human FR regions of the light and heavy variable chains if necessary to maintain proper binding or to enhance binding to the antigen recognized by MN3. More preferably the humanized MN3 MAb or fragment thereof of the present invention comprises the hMN3VH of FIG. 4B and the hMN3VK of FIG. 4A.

In a related vein, chimeric MN3 (cMN3) MAb or fragment thereof of the present invention comprises the CDRs of a murine MN3 MAb and the FR regions of the light and heavy chain variable regions of the murine MN3 MAb. In other words, the cMN3 antibody comprises the Fvs of the parental murine (i.e., mMN3) MAb, and the light and heavy chain constant regions of a human antibody, wherein the CDRs of the light chain variable region of the chimeric MN3 MAb comprise a CDR1 that comprises an amino acid sequence of RSSQSIVHSNGNTYLE (SEQ ID NO: 1), CDR2 that comprises an amino acid sequence of KVSNRFS (SEQ ID NO: 2), and/or CDR3 that comprises an amino acid sequence of FQGSHVPPT (SEQ ID NO: 3); and the CDRs of the heavy chain variable region of the MN3 MAb comprise a CDR1 that comprises an amino acid sequence of NYGMN (SEQ ID NO: 4), a CDR2 that comprises an amino acid sequence of WINTYTGEPTYADDFKG (SEQ ID NO: 5), and/or a CDR3 that comprises an amino acid sequence of KGWMDFNGSSLDY (SEQ ID NO: 6).

More preferably the chimeric MN3 MAb or fragment thereof comprises the complementarity-determining regions (CDRs) of a murine MN3 MAb and the framework (FR) regions of the light and heavy chain variable regions of the murine MN3 MAb and the light and heavy chain constant regions of a human antibody, wherein the CDRs and FRs of the heavy and light chain variable region of the chimeric MN3 MAb comprise the sequence shown in FIGS. 2B and 2A, respectively, designated cMN3VH and cMN3VK.

The present invention also contemplates antibody fusion proteins or fragments thereof comprising at least two MN3

MAbs or fragments thereof. Preferably, the MN3 antibodies and fragments thereof are the MN3 antibodies and fragments thereof of the present invention. Also preferred, the antibody fusion proteins of the present invention are composed of one MN3 MAb and one or more of the second MAbs to provide specificity to different antigens, and are described in more detail below. In a preferred embodiment, the MN3 antibody is an MN3 antibody. The antibody fusion protein or fragment thereof of the present invention is also intended to encompass an antibody fusion protein or fragment thereof comprising at least one first MN3 MAb or fragment thereof as described above and at least one second non-MN3 MAb or fragment thereof. Preferably, the non-MN3 antibody or fragment thereof is a granulocyte associated antibody. A variety of anti-granulocyte antibodies can be used in the present invention. Examples include, but are not limited to, anti-NCA-90, anti-NCA-95, MN-2, MN-3, MN-15, NP-1, NP-2, BW 250/183, and MAb 47 and antibodies directed to antigens present on a single granulocyte precursor, such as anti-CD-15 and anti-CD-33.

The humanized, chimeric and human MN3 antibody may possess enhanced affinity binding with the epitope as a result of CDR mutation and manipulation of the CDR and other sequences in the variable region to obtain a superior therapeutic agent for the treatment of leukemia, and in particular myelogenous, or myeloid, leukemias. Modification to the binding specificity, affinity or avidity of an antibody is known and described in WO 98/44001, as affinity maturation, and this application summarizes methods of modification and is incorporated in its entirety by reference.

It may also be desirable to modify the antibodies of the present invention to improve effector function, e.g., so as to enhance antigen-dependent cell-mediated cytotoxicity (ADCC) and/or complement dependent cytotoxicity (CDC) of the antagonist. One or more amino acid substitutions or the introduction of cysteine in the Fc region may be made, thereby improving internalization capability and/or increased complement-mediated cell killing and ADCC. See Caron et al., *J. Ex. Med.* 176:1191-1195 (1991) and Shopes, B. J. *Immunol.* 148:2918-2022 (1992), incorporated herein by reference in their entirety. An antibody fusion protein may be prepared that has dual Fc regions with both enhanced complement lysis and ADCC capabilities.

Another embodiment of the present invention is a DNA sequence comprising a nucleic acid encoding a MAb or fragment thereof selected from the group consisting of:

(a) an MN3 MAb or fragment thereof as described herein, (b) an antibody fusion protein or fragment thereof comprising at least of the MN3 MAbs or fragments thereof of the present invention, (c) an antibody fusion protein or fragment thereof comprising at least one first MAb or fragment thereof comprising an MN3 MAb or fragment thereof as described herein and at least one second MAb or fragment thereof, other than the MN3 MAb or fragment thereof described herein, and (d) an antibody fusion protein or fragment thereof comprising at least one first MAb or fragment thereof comprising the MN3 MAb or fragment thereof and at least one second MAb or fragment thereof, wherein the second MAb is a an anti-granulocyte antibodies can be used in the present invention including, but not limited to, anti-NCA-90, anti-NCA-95, MN-2, MN-3, MN-15, NP-1, NP-2, BW 250/183, and MAb 47, as well as antibodies against CD15 and CD33, and mixtures of all of the forgoing.

In a related vein, expression vectors comprising the DNA sequences are also considered herein. In the case of vectors for use in preparing the humanized, chimeric and human MN3 MAbs or antibody fusion proteins thereof or fragments thereof, these vectors contain the coding sequences for the light and heavy chain constant regions and the hinge region of the human immunoglobulin, as well as the secretion signal peptide. These vectors additionally contain, where required, promoter/enhancer elements to initiate the Ig gene expression in the selected host cell, and a drug-resistant marker for selection of transfected cells. Vectors that are particularly useful in the present invention are DHFR (such as pdHL2) or GS-vector, particularly when used to express a chimeric, humanized or human antibody, such as an IgG, where the vector codes for the heavy and light chain constant regions and hinge region of IgG1. More preferably, the light and heavy chain constant regions and hinge region are from a human EU myeloma immunoglobulin, where optionally at least one of the amino acid residues in the allotype positions is changed to that found in a different IgG1 allotype, and wherein optionally amino acid I253 of the heavy chain of EU (based on the EU numbering system) may be replaced with alanine. See Edelman et al., *Proc. Natl. Acad Sci USA* 63: 78-85 (1969), incorporated herein in its entirety by reference.

Host cells containing the DNA sequences encoding the MN3 MAbs or fragments thereof or antibody fusion proteins or fragments thereof of the present invention or host cells containing the vectors that contain these DNA sequences are encompassed by the present invention. Particularly useful host cells are mammalian cells, and more specifically, myeloma cell lines, such as Sp2/0, YB2/0, NS0, and CHO, such as DG-44, as discussed in more detail below. Also useful for producing monoclonal antibodies and other fusion proteins is the PER.C6® human cell line.

Also encompassed by the present invention is the method of expressing a MN3 MAb or fragment thereof or a MN3 fusion protein or fragment thereof comprising: (a) transfecting a mammalian cell with a DNA sequence of encoding a MN3 MAb or fragment thereof or an antibody fusion protein or fragments thereof, and (b) culturing the cell transfected with the DNA sequence that secretes the MN3 or fragment thereof or MN3 antibody fusion protein or fragment thereof. Known techniques may be used that include a selection marker on the vector so that host cells that express the MAbs and the marker can be easily selected.

The present invention also encompasses liver cell targeting diagnostic/detection or therapeutic immunoconjugates comprising an MN3 MAb or fragment thereof or an MN3 fusion protein or fragment thereof, that bind to cell expressing the antigen recognized by MN3 and is bound to at least one diagnostic/detection and/or at least one therapeutic agent.

In a preferred embodiment, the diagnostic/detection immunoconjugate comprises an MN3 MAb or fragment thereof or an antibody fusion protein or fragment thereof, and at least one diagnostic/detection agent. Examples of diagnostic/detection agents include diverse labels, radionuclides, chelators, dyes, fluorescent compounds, chromagens, and other marker moieties. Radionuclides useful for positron emission tomography include, but are not limited to: F-18, Mn-51, Mn-52m, Fe-52, Co-55, Cu-62, Cu-64, Ga-68, As-72, Br-75, Br-76, Rb-82m, Sr-83, Y-86, Zr-89, Tc-94m, In-110, I-120, and I-124. Total decay energies of useful positron-emitting radionuclides are preferably <2,000 keV, more preferably under 1,000 keV, and most preferably <700 keV. Radionuclides useful as diagnostic agents utilizing gamma-ray detection include, but are not limited to: Cr-51, Co-57, Co-58, Fe-59, Cu-67, Ga-67, Se-75, Ru-97, Tc-99m, In-111, In-114m, I-123, I-125, I-131, Yb-169, Hg-197, and Tl-201. Decay energies of useful gamma-ray emitting radionuclides are preferably 20-2000 keV, more preferably 60-600 keV, and most preferably 100-300 keV. The diagnostic agent of the present invention may also be a contrast agent such as manganese, iron or gadolinium.

Also preferred, the therapeutic immunoconjugate of the present invention comprises an MN3 antibody or fragment thereof, or an MN3 fusion protein or fragment thereof, and at least one therapeutic agent. Examples of therapeutic agents include a radioactive label, an immunomodulator, a hormone, a photoactive therapeutic agent, a cytotoxic agent, which may be a drug or a toxin, and a combination thereof. The drugs useful in the present invention are those drugs that possess the pharmaceutical property selected from the group consisting of antimitotic, alkylating, antimetabolite, antibiotic, alkaloid, antiangiogenic, apoptotic agents and combinations thereof. More specifically, these drugs are selected from the group consisting of nitrogen mustards, ethylenimine derivatives, alkyl sulfonates, nitrosoureas, triazenes, folic acid analogs, COX-2 inhibitors, pyrimidine analogs, purine analogs, antibiotics, enzymes, epipodophyllotoxins, platinum coordination complexes, vinca alkaloids, substituted ureas, methyl hydrazine derivatives, adrenocortical suppressants, antagonists, endostatin, taxols, camptothecins, anthracyclines, taxanes, and their analogs, and a combination thereof. The toxins encompassed by the present invention are bacterial, plant, or animal toxins, such as those selected from the group consisting of ricin, abrin, alpha toxin, saporin, onconase, i.e., ribonuclease (RNase), DNase I, *Staphylococcal* enterotoxin-A, pokeweed antiviral protein, gelonin, diphtherin toxin, *Pseudomonas* exotoxin, and *Pseudomonas* endotoxin.

Suitable immunomodulators for the present invention include cytokine, a stem cell growth factor, a lymphotoxin, a hematopoietic factor, a colony stimulating factor (CSF), an interferon (IFN), erythropoietin, thrombopoietin and a combination thereof. More specifically lymphotoxins, including tumor necrosis factor (TNF), hematopoietic factors, including interleukin (IL-1, IL-2, IL-3, IL-6, IL-10, IL-12, IL-18, IL-21), colony stimulating factor, including granulocyte-colony stimulating factor (G-CSF) or granulocyte macrophage-colony stimulating factor (GM-CSF)), interferon, including interferons-α, -β or -γ, and stem cell growth factor, including designated “S1 factor.”

Particularly useful therapeutic immunoconjugates comprise one or more radioactive labels that have an energy between 60 and 700 keV. Such radioactive labels include, but ar not limited to $^{32}$P, $^{33}$P, $^{47}$Sc, 59Fe, $^{64}$Cu, $^{67}$Cu, $^{75}$Se, $^{77}$As, $^{89}$Sr, $^{90}$Y, $^{99}$Mo, $^{105}$Rh, $^{109}$Pd, $^{111}$Ag, $^{125}$I, $^{131}$I, $^{142}$Pr, $^{143}$Pr, $^{149}$Pm, $^{153}$Sm, $^{161}$Tb, $^{166}$Ho, $^{169}$Er, $^{177}$Lu, $^{186}$Re, $^{188}$Re, $^{189}$Re, $^{194}$Ir, $^{198}$Au, $^{199}$Au, $^{211}$Pb, $^{212}$Pb, $^{213}$Bi, $^{58}$Co, $^{67}$Ga, $^{80m}$Br, $^{99m}$Tc, $^{103m}$Rh, $^{109}$Pt, $^{111}$In, $^{119}$Sb, $^{125}$I, $^{161}$Ho, $^{189m}$Os, $^{192}$Ir, $^{152}$Dy, $^{211}$At, $^{212}$Bi, $^{223}$Ra, $^{219}$Rn, $^{215}$Po, $^{211}$Bi, $^{225}$Ac, $^{221}$Fr, $^{217}$At, $^{213}$Bi and $^{255}$Fm, and combinations thereof. Other useful therapeutic conjugates are photoactive therapeutic agent, such as a chromogen or dye.

The present invention particularly encompasses methods of treating, detecting or imaging sites of inflammation, including inflammation resulting from appendicitis, inflammatory bowel disease, pelvic inflammatory disease, fever of unknown origin and cystic fibrosis, was well as in treating granulocyte related disorders, such as myeloid leukemia, in a subject, such as a mammal, including humans, domestic or companion pets, such as dogs and cats, comprising administering to the subject a therapeutically effective amount of an MN3 MAb or a fragment thereof of the present invention, formulated in a pharmaceutically acceptable vehicle. Therapeutic applications of Mabs are discussed in Magic bullets hit the target. Nature 417:584-586, 2002. Preferably the MN3 antibody or fragment thereof is an MN3 antibody or fragment thereof. This therapy utilizes a “naked antibody” that does not have a therapeutic agent bound to it. The administration of the “naked MN3 antibody” can be supplemented by administering to the subject concurrently or sequentially a therapeutically effective amount of at least one other “naked antibody” that binds to or is reactive with another antigen on the surface of the target cell or that has other functions, such as effector functions in the Fc portion of the MAb, that is therapeutic and which is discussed herein. For example, preferred MAbs that can supplement the naked MN3 antibody are humanized, chimeric, human or murine (in the case of non-human animals) anti-granulocyte antibodies. Examples include, but are not limited to, anti-NCA-90, anti-NCA-95, MN-2, MN-3, MN-15, NP-1, NP-2, BW 250/183, and MAb 47, as well as antibodies against CD15 and CD33.

Both the naked MN3 antibody therapy alone or in combination with other naked MAbs or fragments thereof as discussed above can be further supplemented with the administration, either concurrently or sequentially, of a therapeutically effective amount of at least one therapeutic agent, formulated in a pharmaceutically acceptable vehicle. As discussed herein the therapeutic agent may comprise a cytotoxic agent, a radioactive label, an immunomodulator, a hormone, a photoactive therapeutic agent or a combination thereof, formulated in a pharmaceutically acceptable vehicle.

In another therapeutic method, both the naked MN3 therapy alone or in combination with other naked MAbs, as discussed above, can be further supplemented with the administration, either concurrently or sequentially, of a therapeutically effective amount of at least one therapeutic immunoconjugate, described herein and formulated in a pharmaceutically acceptable vehicle. The therapeutic immunoconjugate comprises at least one humanized, chimeric, human or murine (for non-human subjects) MAb selected from the group consisting of a MAbs reactive with NCA-90, NCA-95, CD15, CD33, and from the MAbs MN2, MN3, MN-15, NP-1, NP-2, BW 250/183, and MAb 47. The therapeutic immunoconjugate may be conjugated to at least one therapeutic agent selected from the group consisting of a cytotoxic agent, a radioactive label, an immunomodulator, a hormone, a photoactive therapeutic agent or a combination thereof, formulated in a pharmaceutically acceptable vehicle.

As described herein the methods provide methods of imaging sites of inflammation, including inflammation resulting from appendicitis, inflammatory bowel disease, pelvic inflammatory disease, fever of unknown origin and cystic fibrosis, was well as in treating granulocyte-related disorders, such as myeloid leukemia, in a subject comprising administering to a subject a therapeutically effective amount of an antibody fusion protein or fragment thereof comprising at least two MN3 MAbs or fragments thereof of the present invention or comprising at least one MN3 MAb or fragment thereof of the present invention and at least one granulocyte associated MAb. Preferably, the anti-granulocyte antibody is elected from the group consisting of MAbs reactive with NCA-90, NCA-95, CD15, CD33, and from the MAbs MN2, MN3, MN-15, NP-1, NP-2, BW 250/183, and MAb 47.

These imaging and therapeutic methods can further be supplemented with the administration to the subject concurrently or sequentially of a therapeutically effective amount of at least one therapeutic agent, formulated in a pharmaceutically acceptable vehicle, wherein the therapeutic agent is preferably a cytotoxic agent, a radioactive label, an immunomodulator, a hormone, a photoactive therapeutic agent or a combination thereof, formulated in a pharmaceutically acceptable vehicle.

Further, the antibody fusion proteins and fragments thereof of the present invention can be administered to a subject concurrently or sequentially with a therapeutically effective amount of a therapeutic conjugate comprising at least one MAb bound to at least one therapeutic agent, wherein said MAb component of the conjugate preferably comprises at least one humanized, chimeric, human or murine (for non-human subjects) MAb selected from the group consisting of a MAbs reactive with NCA-90, NCA-95, CD15, CD33, and from the MAbs MN2, MN3, MN-15, NP-1, NP-2, BW 250/183, and MAb 47.

The antibody fusion protein itself may also be conjugated to at least one therapeutic agent. These therapeutic agents can be a combination of different recited agents or combinations of the same agents, such as two different therapeutic radioactive labels.

Also encompassed by the present invention is a method of diagnosing/detecting inflammation and granulocyte related disorders or cancers in a subject comprising administering to the subject, such as a mammal, including humans and domestic and companion pets, such as dogs, cats, rabbits, guinea pigs, a diagnostic/detection immunoconjugate comprising an MN3 MAb or fragment thereof or an MN3 fusion protein or fragment thereof of the present invention that binds to the cell expressing an antigen recognized by MN3, wherein the MN3 MAb or fragment thereof or antibody fusion protein or fragment thereof is bound to at least one diagnostic/detection agent. Optionally, the diagnostic/detection immunoconjugate is formulated in a pharmaceutically acceptable vehicle. The useful diagnostic agents are described herein.

2. Definitions

In the description that follows, a number of terms are used and the following definitions are provided to facilitate understanding of the present invention.

An antibody, as described herein, refers to a full-length (i.e., naturally occurring or formed by normal immunoglobulin gene fragment recombinatorial processes) immunoglobulin molecule (e.g., an IgG antibody) or an immunologically active (i.e., specifically binding) portion of an immunoglobulin molecule, like an antibody fragment.

An antibody fragment is a portion of an antibody such as $F(ab')_2$, $F(ab)_2$, Fab', Fab, Fv, sFv and the like. Regardless of structure, an antibody fragment binds with the same antigen that is recognized by the intact antibody. For example, an MN3 monoclonal antibody fragment binds with an epitope recognized by MN3. The term "antibody fragment" also includes any synthetic or genetically engineered protein that acts like an antibody by binding to a specific antigen to form a complex. For example, antibody fragments include isolated fragments consisting of the variable regions, such as the "Fv" fragments consisting of the variable regions of the heavy and light chains, recombinant single chain polypeptide molecules in which light and heavy variable regions are connected by a peptide linker ("scFv proteins"), and minimal recognition units consisting of the amino acid residues that mimic the hypervariable region.

The term anti-granulocyte antibody refers to an antibody which recognizes an antigen which is present on one or more cell-types of the neutrophil/granulocyte/myelocyte lineage.

A naked antibody is generally an entire antibody which is not conjugated to a therapeutic agent. This is so because the Fc portion of the antibody molecule provides effector functions, such as complement fixation and ADCC (antibody-dependent cell cytotoxicity), which set mechanisms into action that may result in cell lysis. Naked antibodies include both polyclonal and monoclonal antibodies, as well as certain recombinant antibodies, such as chimeric, humanized or human antibodies. However, it is possible that the Fc portion is not required for therapeutic function, rather an antibody exerts its therapeutic effect through other mechanisms, such as induction of cell cycle resting and apoptosis. In this case, naked antibodies also include the unconjugated antibody fragments defined above.

A chimeric antibody is a recombinant protein that contains the variable domains including the complementarity-determining regions (CDRs) of an antibody derived from one species, preferably a rodent antibody, while the constant domains of the antibody molecule is derived from those of a human antibody. For veterinary applications, the constant domains of the chimeric antibody may be derived from that of other species, such as a cat or dog.

A humanized antibody is a recombinant protein in which the CDRs from an antibody from one species; e.g., a rodent antibody, is transferred from the heavy and light variable chains of the rodent antibody into human heavy and light variable domains. The constant domains of the antibody molecule is derived from those of a human antibody.

A human antibody is an antibody obtained from transgenic mice that have been "engineered" to produce specific human antibodies in response to antigenic challenge. In this technique, elements of the human heavy and light chain locus are introduced into strains of mice derived from embryonic stem cell lines that contain targeted disruptions of the endogenous heavy chain and light chain loci. The transgenic mice can synthesize human antibodies specific for human antigens, and the mice can be used to produce human antibody-secreting hybridomas. Methods for obtaining human antibodies from transgenic mice are described by Green et al., *Nature Genet.* 7:13 (1994), Lonberg et al., *Nature* 368:856 (1994), and Taylor et al., *Int. Immun.* 6:579 (1994). A fully human antibody also can be constructed by genetic or chromosomal transfection methods, as well as phage display technology, all of which are known in the art. See for example, McCafferty et al., *Nature* 348:552-553 (1990) for the production of human antibodies and fragments thereof in vitro, from immunoglobulin variable domain gene repertoires from unimmunized donors. In this technique, antibody variable domain genes are cloned in-frame into either a major or minor coat protein gene of a filamentous bacteriophage, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. In this way, the phage mimics some of the properties of the B cell. Phage display can be performed in a variety of formats, for their review, see e.g. Johnson and Chiswell, *Current Opinion in Structural Biology* 3:5564-571 (1993).

Human antibodies may also be generated by in vitro activated B cells. See U.S. Pat. Nos. 5,567,610 and 5,229,275, which are incorporated in their entirety by reference.

A therapeutic agent is a molecule or atom which is administered separately, concurrently or sequentially with an antibody moiety or conjugated to an antibody moiety, i.e., antibody or antibody fragment, or a subfragment, and is useful in the treatment of a disease. Examples of therapeutic agents include antibodies, antibody fragments, drugs, toxins, nucleases, hormones, immunomodulators, chelators, boron compounds, photoactive agents or dyes and radioisotopes.

A diagnostic agent is a molecule or atom which is administered conjugated to an antibody moiety, i.e., antibody or antibody fragment, or subfragment, and is useful in diagnosing or detecting a disease by locating the cells containing the antigen. Useful diagnostic agents include, but are not limited to, radioisotopes, dyes (such as with the biotin-streptavidin complex), contrast agents, fluorescent compounds or molecules and enhancing agents (e.g., paramagnetic ions) for magnetic resonance imaging (MRI). U.S. Pat. No. 6,331,175 describes MRI technique and the preparation of antibodies conjugated to a MRI enhancing agent and is incorporated in its entirety by reference. Preferably, the diagnostic agents are selected from the group consisting of radioisotopes, enhancing agents for use in magnetic resonance imaging, and fluorescent compounds. In order to load an antibody component with radioactive metals or paramagnetic ions, it may be necessary to react it with a reagent having a long tail to which are attached a multiplicity of chelating groups for binding the ions. Such a tail can be a polymer such as a polylysine, polysaccharide, or other derivatized or derivatizable chain having pendant groups to which can be bound chelating groups such as, e.g., ethylenediaminetetraacetic acid (EDTA), diethylenetriaminepentaacetic acid (DTPA), porphyrins, polyamines, crown ethers, bis-thiosemicarbazones, polyoximes, and like groups known to be useful for this purpose. Chelates are coupled to the antibodies using standard chemistries. The chelate is normally linked to the antibody by a group which enables formation of a bond to the molecule with minimal loss of immunoreactivity and minimal aggregation and/or internal cross-linking other, more unusual, methods and reagents for conjugating chelates to antibodies are disclosed in U.S. Pat. No. 4,824,659 to Hawthorne, entitled "Antibody Conjugates," issued Apr. 25, 1989, the disclosure of which is incorporated herein in its entirety by reference. Particularly useful metal-chelate combinations include 2-benzyl-DTPA and its monomethyl and cyclohexyl analogs, used with diagnostic isotopes in the general energy range of 60 to 4,000 keV, such as $^{125}I$, $^{131}I$, $^{123}I$, $^{124}I$, $^{62}Cu$, $^{64}Cu$, $^{18}F$, $^{111}In$, $^{67}Ga$, $^{68}Ga$, $^{99m}Tc$, $^{94m}Tc$, $^{11}C$, $^{13}N$, $^{15}O$, $^{76}Br$, for radio-imaging. The same chelates, when complexed with non-radioactive metals, such as manganese, iron and gadolinium are useful for MRI, when used along with the antibodies of the invention. Macrocyclic chelates such as NOTA, DOTA, and TETA are of use with a variety of metals and radiometals, most particularly with radionuclides of gallium, yttrium and copper, respectively. Such metal-chelate complexes can be made very stable by tailoring the ring size to the metal of interest. Other ring-type chelates such as macrocyclic polyethers, which are of interest for stably binding nuclides, such as $^{223}Ra$ for RAIT are encompassed by the invention.

An immunoconjugate is a conjugate of an antibody component with a therapeutic or diagnostic agent. The diagnostic agent can comprise a radioactive or non-radioactive label, a contrast agent (such as for magnetic resonance imaging, computed tomography or ultrasound), and the radioactive label can be a gamma-, beta-, alpha-, Auger electron-, or positron-emitting isotope.

An immunomodulator is a therapeutic agent as defined in the present invention that when present, typically stimulates immune cells to proliferate or become activated in an immune response cascade, such as macrophages, B-cells, and/or T cells. An example of an immunomodulator as described herein is a cytokine. As the skilled artisan will understand, certain interleukins and interferons are examples of cytokines that stimulate T cell or other immune cell proliferation.

An expression vector is a DNA molecule comprising a gene that is expressed in a host cell. Typically, gene expression is placed under the control of certain regulatory elements, including constitutive or inducible promoters, tissue-specific regulatory elements and enhancers. Such a gene is said to be "operably linked to" the regulatory elements.

A recombinant host may be any prokaryotic or eukaryotic cell that contains either a cloning vector or expression vector. This term also includes those prokaryotic or eukaryotic cells, as well as an transgenic animal, that have been genetically engineered to contain the cloned gene(s) in the chromosome or genome of the host cell or cells. Suitable mammalian host cells include myeloma cells, such as SP2/0 cells, and NS0 cells, as well as Chinese Hamster Ovary (CHO) cells, hybridoma cell lines and other mammalian host cells useful for expressing antibodies. Also particularly useful to express MAbs and other fusion proteins, is a human cell line, PER.C6®, disclosed in WO 0063403 A2, which produces 2 to 200-fold more recombinant protein as compared to conventional mammalian cell lines, such as CHO, COS, Vero, Hela, BHK and SP2-cell lines. Special transgenic animals with a modified immune system are particularly useful for making fully human antibodies.

As used herein, the term antibody fusion protein is a recombinantly produced antigen-binding molecule in which two or more of the same or different natural antibody, single-chain antibody or antibody fragment segments with the same or different specificities are linked. An MN3 fusion protein comprises a binding site for an antigen recognized by MN3. The MN3 fusion protein and fragment thereof of the present invention comprise at least one arm that binds to the same epitope an antibody or antibody fragment comprising CDR1 of a heavy chain variable region that comprises an amino acid sequence of NYGMN, (SEQ ID NO: 4) a CDR2 that comprises an amino acid sequence of WINTYTGEPTYADDFKG (SEQ ID NO: 5), and/or a CDR3 that comprises an amino acid sequence of KGWMDFNGSSLDY (SEQ ID NO: 6), and/or CDR1 of a light chain variable region that comprises an amino acid sequence of RSSQSIVHSNGNTYLE (SEQ ID NO: 1), CDR2 that comprises an amino acid sequence of KVSNRFS (SEQ ID NO: 2), and/or CDR3 that comprises an amino acid sequence of FQGSHVPPT (SEQ ID NO: 3).

Valency of the fusion protein indicates the total number of binding arms or sites the fusion protein has to antigen(s) or epitope(s); i.e., monovalent, bivalent, trivalent or multivalent. The multivalency of the antibody fusion protein means that it can take advantage of multiple interactions in binding to an antigen, thus increasing the avidity of binding to the antigen, or to different antigens. Specificity indicates how many different types of antigen or epitope an antibody fusion protein is able to bind; i.e., monospecific, bispecific, trispecific, multispecific. Using these definitions, a natural antibody, e.g., an IgG is bivalent because it has two binding arms but is monospecific because it binds to one type of antigen or epitope. A monospecific, multivalent fusion protein has more than one binding site for the same antigen or epitope. For example, a monospecific diabody is a fusion protein with two binding sites reactive with the same antigen. The fusion protein may comprise a multivalent or multispecific combination of different antibody components or multiple copies of the same antibody component. The fusion protein may additionally comprise a therapeutic agent. Examples of therapeutic agents suitable for such fusion proteins include immunomodulators ("antibody-immunomodulator fusion protein") and toxins ("antibody-toxin fusion protein"). One preferred toxin comprises a ribonuclease (RNase), preferably a recombinant RNase.

A multispecific antibody is an antibody that can bind simultaneously to at least two targets that are of different structure, e.g., two different antigens, two different epitopes on the same antigen, or a hapten and an antigen or epitope. One specificity would be for, for example, a B-cell, T-cell, myeloid-, plasma-, or mast-cell antigen or epitope. Another specificity could be to a different antigen on the same cell type, such as CD20, CD19, CD21, CD23, CD46, CD80, HLA-DR, CD74, or CD22 on B-cells. Multispecific, multivalent antibodies are constructs that have more than one binding site, and the binding sites are of different specificity. For example, a bispecific diabody, where one binding site reacts with one antigen and the other with another antigen.

A bispecific antibody is an antibody that can bind simultaneously to two targets which are of different structure. Bispecific antibodies (bsAb) and bispecific antibody fragments (bsFab) have at least one arm that specifically binds to, for example, granulocyte or myeloid antigen or epitope and at least one other arm that specifically binds to a targetable conjugate that bears a therapeutic or diagnostic agent. A variety of bispecific fusion proteins can be produced using molecular engineering. In one form, the bispecific fusion protein is divalent, consisting of, for example, a scFv with a single binding site for one antigen and a Fab fragment with a single binding site for a second antigen. In another form, the bispecific fusion protein is tetravalent, consisting of, for example, an IgG with two binding sites for one antigen and two identical scFv for a second antigen.

Caninized or felinized antibodies are recombinant proteins in which rodent (or another species) complementarity-determining regions of a monoclonal antibody (MAb) have been transferred from heavy and light variable chains of rodent (or another species) immunoglobulin into a dog or cat, respectively, immunoglobulin variable domain.

Domestic animals include large animals such as horses, cattle, sheep, goats, llamas, alpacas, and pigs, as well as companion animals. In a preferred embodiment, the domestic animal is a horse.

Companion animals include animals kept as pets. These are primarily dogs and cats, although small rodents, such as guinea pigs, hamsters, rats, and ferrets, are also included, as are subhuman primates such as monkeys. In a preferred embodiment the companion animal is a dog or a cat.

3. Preparation of Monoclonal Antibodies Including Chimeric, Humanized and Human Antibodies A monoclonal antibody (MAb) is an immunoglobulin that has specific binding activity to a particular antigen and the antibody comprises only one antigen binding site that binds to only one epitope or one antigenic determinant of the antigen. Rodent monoclonal antibodies to specific antigens may be obtained by methods known to those skilled in the art. See, for example, Kohler and Milstein, *Nature* 256: 495 (1975), and Coligan et al. (eds.), CURRENT PROTOCOLS IN IMMUNOLOGY, VOL. 1, pages 2.5.1-2.6.7 (John Wiley & Sons 1991) [hereinafter "Coligan"]. Briefly, monoclonal antibodies can be obtained by injecting mice with a composition comprising an antigen, verifying the presence of antibody production by removing a serum sample, removing the spleen to obtain B-lymphocytes, fusing the B-lymphocytes with myeloma cells to produce hybridomas, cloning the hybridomas, selecting positive clones which produce antibodies to the antigen, culturing the clones that produce antibodies to the antigen, and isolating the antibodies from the hybridoma cultures.

MAbs can be isolated and purified from hybridoma cultures by a variety of well-established techniques. Such isolation techniques include affinity chromatography with Protein-A or Protein-G Sepharose, size-exclusion chromatography, and ion-exchange chromatography. See, for example, Coligan at pages 2.7.1-2.7.12 and pages 2.9.1-2.9.3. Also, see Baines et al., "Purification of Immunoglobulin G (IgG)," in METHODS IN MOLECULAR BIOLOGY, VOL. 10, pages 79-104 (The Humana Press, Inc. 1992).

Abs against peptides are generated by well-known methods for Ab production. For example, injection of an immunogen, such as $(\text{peptide})_n$-KLH, wherein KLH is keyhole limpet hemocyanin, and n=1-30, in complete Freund's adjuvant, followed by two subsequent injections of the same immunogen suspended in incomplete Freund's adjuvant into immunocompetent animals. The animals are given a final i.v. boost of antigen, followed by spleen cell harvesting three days later. Harvested spleen cells are then fused with Sp2/0-Ag14 myeloma cells and culture supernatants of the resulting clones analyzed for anti-peptide reactivity using a direct-binding ELISA. Fine specificity of generated Abs can be analyzed for by using peptide fragments of the original immunogen. These fragments can be prepared readily using an automated peptide synthesizer. For Ab production, enzyme-deficient hybridomas are isolated to enable selection of fused cell lines. This technique also can be used to raise antibodies to one or more of the chelates comprising the linker, e.g., In(III)-DTPA chelates. Monoclonal mouse antibodies to an In(III)-di-DTPA are known (Barbet '395 supra).

After the initial raising of antibodies to the immunogen, the variable genes of the monoclonal antibodies can be cloned from the hybridoma cells, sequenced and subsequently prepared by recombinant techniques. Humanization and chimerization of murine antibodies and antibody fragments are well known to those skilled in the art. For example, humanized monoclonal antibodies are produced by transferring mouse complementary determining regions from heavy and light variable chains of the mouse immunoglobulin into a human variable domain, and then, substituting human residues in the framework regions with the murine counterparts, which play an important role in antigen binding. In a preferred embodiment, one or more human residues in the framework regions of the humanized MN3 antibody or fragments thereof are replaced by their murine counterparts. It is also preferred that a combination of framework sequences from 2 different human antibodies are used for $V_H$. Still preferred, the two human antibodies are EU and KOL. The constant domains of the antibody molecule are derived from those of a human antibody. The use of antibody components derived from humanized monoclonal antibodies obviates potential problems associated with the immunogenicity of murine constant regions.

General techniques for cloning murine immunoglobulin variable domains are described, for example, by the publication of Orlandi et al., *Proc. Nat'l Acad. Sci. USA* 86: 3833 (1989), which is incorporated by reference in its entirety. Techniques for constructing chimeric antibodies are well known to those of skill in the art. As an example, Leung et al., *Hybridoma* 13:469 (1994), describe how they produced an LL2 chimera by combining DNA sequences encoding the $V_\kappa$ and $V_H$ domains of LL2 monoclonal antibody, an anti-CD22 antibody, with respective human κ and $IgG_1$ constant region domains. This publication also provides the nucleotide sequences of the LL2 light and heavy chain variable regions, $V_\kappa$ and $V_H$, respectively. Techniques for producing humanized MAbs are described, for example, by Jones et al., *Nature* 321: 522 (1986), Riechmann et al., *Nature* 332: 323 (1988), Verhoeyen et al., *Science* 239: 1534 (1988), Carter et al., *Proc. Nat'l Acad. Sci. USA* 89: 4285 (1992), Sandhu, *Crit. Rev. Biotech.* 12: 437 (1992), and Singer et al., *J. Immun.* 150: 2844 (1993), each of which is hereby incorporated by reference.

Another method for producing the antibodies of the present invention is by production in the milk of transgenic livestock. See, e.g., Colman, A., *Biochem. Soc. Symp.,* 63: 141-147, 1998; U.S. Pat. No. 5,827,690, both of which are incorporated in their entirety by reference. Two DNA constructs are prepared which contain, respectively, DNA segments encoding paired immunoglobulin heavy and light chains. The DNA segments are cloned into expression vectors which contain a promoter sequence that is preferentially expressed in mammary epithelial cells. Examples include, but are not limited to, promoters from rabbit, cow and sheep casein genes, the cow $\alpha$-lactoglobulin gene, the sheep $\beta$-lactoglobulin gene and the mouse whey acid protein gene. Preferably, the inserted fragment is flanked on its 3' side by cognate genomic sequences from a mammary-specific gene. This provides a polyadenylation site and transcript-stabilizing sequences. The expression cassettes are coinjected into the pronuclei of fertilized, mammalian eggs, which are then implanted into the uterus of a recipient female and allowed to gestate. After birth, the progeny are screened for the presence of both transgenes by Southern analysis. In order for the antibody to be present, both heavy and light chain genes must be expressed concurrently in the same cell. Milk from transgenic females is analyzed for the presence and functionality of the antibody or antibody fragment using standard immunological methods known in the art. The antibody can be purified from the milk using standard methods known in the art.

A chimeric antibody is a recombinant protein that contains the variable domains including the CDRs derived from one species of animal, such as a rodent antibody, while the remainder of the antibody molecule; i.e., the constant domains, is derived from a human antibody. Accordingly, a chimeric monoclonal antibody (MAb) can also be humanized by replacing the sequences of the murine FR in the variable domains of the chimeric MAb with one or more different human FRs. Specifically, mouse CDRs are transferred from heavy and light variable chains of the mouse immunoglobulin into the corresponding variable domains of a human antibody. As simply transferring mouse CDRs into human FRs often results in a reduction or even loss of antibody affinity, additional modification might be required in order to restore the original affinity of the murine antibody. This can be accomplished by the replacement of one or more human residues in the FR regions with their murine counterparts to obtain an antibody that possesses good binding affinity to its epitope. See, for example, Tempest et al., *Biotechnology* 9:266 (1991) and Verhoeyen et al., *Science* 239: 1534 (1988). Further, the affinity of humanized, chimeric and human MAbs to a specific epitope can be increased by mutagenesis of the CDRs, so that a lower dose of antibody may be as effective as a higher dose of a lower affinity MAb prior to mutagenesis. See for example, WO0029584A1.

A fully human antibody of the present invention, i.e., a human MN3 MAb or another human antibody, used for combination therapy with humanized or chimeric MN3 antibodies, can be obtained from a transgenic non-human animal. See, e.g., Mendez et al., *Nature Genetics,* 15: 146-156 (1997) and U.S. Pat. No. 5,633,425, which are incorporated in their entirety by reference. For example, a human antibody can be recovered from a transgenic mouse possessing human immunoglobulin loci. The mouse humoral immune system is humanized by inactivating the endogenous immunoglobulin genes and introducing human immunoglobulin loci. The human immunoglobulin loci are exceedingly complex and comprise a large number of discrete segments which together occupy almost 0.2% of the human genome. To ensure that transgenic mice are capable of producing adequate repertoires of antibodies, large portions of human heavy- and light-chain loci generally are introduced into the mouse genome. This is accomplished in a stepwise process beginning with the formation of yeast artificial chromosomes (YACs) containing either human heavy- or light-chain immunoglobulin loci in germline configuration. Since each insert is approximately 1 Mb in size, YAC construction requires homologous recombination of overlapping fragments of the immunoglobulin loci. The two YACs, one containing the heavy-chain loci and one containing the light-chain loci, are introduced separately into mice via fusion of YAC-containing yeast spheroblasts with mouse embryonic stem cells. Embryonic stem cell clones are then microinjected into mouse blastocysts. Resulting chimeric males are screened for their ability to transmit the YAC through their germline and are bred with mice deficient in murine antibody production. Breeding the two transgenic strains, one containing the human heavy-chain loci and the other containing the human light-chain loci, creates progeny which produce human antibodies in response to immunization.

Unrearranged human immunoglobulin genes also can be introduced into mouse embryonic stem cells via microcell-mediated chromosome transfer (MMCT). See, e.g., Tomizuka et al., *Nature Genetics,* 16: 133 (1997). In this methodology microcells containing human chromosomes are fused with mouse embryonic stem cells. Transferred chromosomes are stably retained, and adult chimeras exhibit proper tissue-specific expression.

As an alternative, an antibody or antibody fragment of the present invention may be derived from human antibody fragments isolated from a combinatorial immunoglobulin library. See, e.g., Barbas et al., *METHODS: A Companion to Methods in Enzymology* 2: 119 (1991), and Winter et al., *Ann. Rev. Immunol.* 12: 433 (1994), which are incorporated by reference. Many of the difficulties associated with generating monoclonal antibodies by B-cell immortalization can be overcome by engineering and expressing antibody fragments in *E. coli*, using phage display. To ensure the recovery of high affinity, monoclonal antibodies a combinatorial immunoglobulin library must contain a large repertoire size. A typical strategy utilizes mRNA obtained from lymphocytes or spleen cells of immunized mice to synthesize cDNA using reverse transcriptase. The heavy- and light-chain genes are amplified separately by PCR and ligated into phage cloning vectors. Two different libraries are produced, one containing the heavy-chain genes and one containing the light-chain genes. Phage DNA is isolated from each library, and the heavy-and light-chain sequences are ligated together and packaged to form a combinatorial library. Each phage contains a random pair of heavy- and light-chain cDNAs and upon infection of *E. coli* directs the expression of the antibody chains in infected cells. To identify an antibody that recognizes the antigen of interest, the phage library is plated, and the antibody molecules present in the plaques are transferred to filters. The filters are incubated with radioactively labeled antigen and then washed to remove excess unbound ligand. A radioactive spot on the autoradiogram identifies a plaque that contains an antibody that binds the antigen. Cloning and expression vectors that are useful for producing a human immunoglobulin phage library can be obtained, for example, from STRATAGENE Cloning Systems (La Jolla, Calif.).

Further, recent methods for producing bispecific MAbs include engineered recombinant MAbs which have additional cysteine residues so that they crosslink more strongly than the more common immunoglobulin isotypes. See, e.g., FitzGerald et al., Protein Eng. 10(10):1221-1225, 1997. Another approach is to engineer recombinant fusion proteins linking two or more different single-chain antibody or antibody fragment segments with the needed dual specificities. See, e.g., Coloma et al., *Nature Biotech.* 15:159-163, 1997. A variety of bispecific fusion proteins can be produced using molecular engineering. In one form, the bispecific fusion protein is monovalent, consisting of, for example, a scFv with a single binding site for one antigen and a Fab fragment with a single binding site for a second antigen. In another form, the bispecific fusion protein is divalent, consisting of, for example, an IgG with two binding sites for one antigen and two scFv with two binding sites for a second antigen.

Bispecific fusion proteins linking two or more different single-chain antibodies or antibody fragments are produced in similar manner. Recombinant methods can be used to produce a variety of fusion proteins. For example a fusion protein comprising a Fab fragment derived from a humanized monoclonal MN3 antibody and a scFv derived from a murine anti-diDTPA can be produced. A flexible linker, such as GGGS (SEQ ID NO: 27) connects the scFv to the constant region of the heavy chain of the MN3 antibody. Alternatively, the scFv can be connected to the constant region of the light chain of another humanized antibody. Appropriate linker sequences necessary for the in-frame connection of the heavy chain Fd to the scFv are introduced into the VL and VK domains through PCR reactions. The DNA fragment encoding the scFv is then ligated into a staging vector containing a DNA sequence encoding the CH1 domain. The resulting scFv-CH1 construct is excised and ligated into a vector containing a DNA sequence encoding the VH region of an MN3 antibody. The resulting vector can be used to transfect an appropriate host cell, such as a mammalian cell for the expression of the bispecific fusion protein.

Preparation of Chimeric, Humanized and Human MN3 Antibodies

Cell lines and culture media used in the present invention include MN3 producing hybridoma cells and Sp2/0-Ag14 myeloma cells (ATCC, Manassas, Va.). These cells may be cultured in Hybridoma serum-free media (HSFM) (life Technologies, Grand Island, N.Y.) supplemented with 10% fetal bovine serum (FBS) (Hyclone Laboratories, Logan, Utah) and antibiotics (complete media). Alternatively, they may be cultured in Dulbecco's modified Eagle's Medium (DMEM) supplemented with 10% FCS (Gibco/BRL, Gaithersburg, Md.) containing 10% of FCS and 75 μg/ml gantamicin (complete HSFM) or, where indicated, in HSFM containing only antibiotics. Selection of the transfectomas may be carried out in complete HSFM containing and appropriate cytocidal drug, such as hygromycin (hyg) and methotrexate (MTX). All cell lines are preferably maintained at 37° C. in 5% $CO_2$.

Obtaining Vκ and VH Gene Segments

Isolation of the Vκ and $V_H$ gene segments can be accomplished by several means that are well-known in the art. Two such means include, but are not limited to, PCR cloning and cDNA library screening.

PCR cloning techniques are well-known in the art. In brief, however, PCR cloning of Vκ and $V_H$ gene fragments may be accomplished as follows. Total RNA may be isolated from a MN3 hybridoma cell line using commercially available kits such as the Fast Track RNA Isolation kit (Invitrogen, San Diego, Calif.). The first strand cDNA may then be reverse transcribed from RNA using a cDNA cycle kit (Invitrogen). In this process, 5 μg of total RNA is annealed to an oligo dT or random hexamer primer, or a murine IgG CH1-specific primer or a murine Cκ-specific primer. Examples of such primers include CH1B (5'-ACA GTC ACT GAG CTG G-3') (SEQ ID NO: 28) and CK3-BH1 (5'-GCC GGA TCC TGA CTG GAT GGT GGG AAG ATG GAT ACA-3') (SEQ ID NO: 29), respectively. The first strand cDNA may be used as templates to amplify the $V_H$ and Vκ sequences by PCR, as described by Orlandi et al. For the VK region, a primer pair such as VK1BACK (5'-GAC ATT CAG CTG ACC CAG TCT CCA-3') (SEQ ID NO: 30) and IgKC3' (5'-CTC ACT GGA TGG TGG GAA GAT GGA TAC AGT TGG-3') (SEQ ID NO: 31) may be used. For the $V_H$ region, a primer pair such as VH1BACK (5'-AGG T(C/G)(A/C) A(A/G)C TGC AG(C/G) AGT C(A/T)G G-3') (SEQ ID NO: 32) and CH1B may be used. After amplification, the Vκ and $V_H$ fragments may then be gel-purified and cloned into a cloning vector such as the TA cloning vector (Invitrogen) for sequence analyses by the dideoxytermination method. Sequences confirmed to be of immunoglobulin origin may then be used to construct chimeric Ab expression vectors using methods described by Leung et al. (Hybridoma, 13:469 (1994)).

As a preferred alternative to isolating the Vκ and $V_H$ gene segments by PCR cloning, cDNA library screening may be utilized. cDNA screening methods also are well known in the art. In brief, however, a cDNA library may be constructed from the mRNA extracted from the murine MN3 hybridoma cells in pSPORT vector (Life Technologies). The first strand cDNA may be synthesized by priming poly A RNA from MN3 hybridoma with an oligo dT primer-NotI adaptor (Life Technologies). After the second strand synthesis and attachment of SalI adaptors, the cDNA pool may be size fractionated through a cDNA size fractionation column. Fractionated cDNA may then be ligated to pSPORT vector and subsequently transformed into *Escherichia coli* DH5α. A library may then be plated, transferred to filters, and amplified.

Screening of the cDNA library may be accomplished by hybridization with labeled probes specific for the heavy and light chains. For example [$^{32}P$]-labeled probes such as MUCH-1 (5'-AGA CTG CAG GAG AGC TGG GAA GGT GTG CAC-3') (SEQ ID NO: 33) for heavy chain and MUCK-1 (5'-GAA GCA CAC GAC TGA GGC ACC TCC AGA TGT-3') (SEQ ID NO: 34) for light chain. Clones that are positive on a first screening may be transferred to duplicate plates and screened a second time with the same probes.

RNA isolation, cDNA synthesis, and amplification can be carried out as follows. Total cell RNA can be prepared from a MN3 hybridoma cell line, using a total of about $10^7$ cells, according to Sambrook et al., (Molecular Cloning: A Laboratory Manual, Second ed., Cold Spring Harbor Press, 1989), which is incorporated by reference. First strand cDNA can be reverse transcribed from total RNA conventionally, such as by using the SuperScript™ preamplification system (Gibco/BRL, Gaithersburg, Md.). Briefly, in a reaction volume of 20 μl, 50 ng of random hexamer primers can be annealed to 5 μg of RNAs in the presence of 2 μl of 10× synthesis buffer [200 mM Tris-HCl (pH 8.4), 500 mM KCl, 25 mM $MgCl_2$, 1 mg/ml BSA], 1 μl of 10 mM dNTP mix, 2 μl of 0.1 M DTT, and 200 units of SuperScript™ reverse transcriptase. The elongation step is initially allowed to proceed at room temperature for 10 min followed by incubation at 42° C. for 50 min. The reaction can be terminated by heating the reaction mixture at 90° C. for 5 min.

Synthesizing and labeling the screening probes can be accomplished by well-known means. Depending on the detection systems utilized, probe labeling will vary. Many kits for this purpose are commercially available. One method for 32-P labeling of oligonucleotides includes the use of with [γ-$^{32}P$]ATP (Amersham Arlington Heights, Ill.) and T4 polynucleotide kinase (New England Biolabs, Beverly, Mass.), followed by column purification.

Preparation of a Chimeric MN3 Antibody

In a preferred embodiment, the MN3 antibody is a chimeric MN3 antibody (cMN3). The Vκ PCR products may be subcloned into a pBR327 based staging vector (VKpBR) as described by Leung et al., Hybridoma, 13:469 (1994). The $V_H$ PCR products may be subcloned into a similar pBluescript-based staging vector (VHpBS). The fragments containing the Vκ and $V_H$ sequences, along with the promoter and signal peptide sequences, can be excised from the staging vectors using HindIII and BamHI restriction endonucleases. The Vκ fragments (about 600 bp) can be subcloned into a mammalian expression vector (for example, pKh) conventionally. pKh is a pSVhyg-based expression vector containing the genomic sequence of the human kappa constant region, an Ig enhancer, a kappa enhancer and the hyg-resistant gene. Similarly, the about 800 bp $V_H$ fragments can be subcloned into pG1g, a pSVgpt-based expression vector carrying the genomic sequence of the human IgG1 constant region, an Ig enhancer and the xanthine-guanine phosphoribosyl transferase (gpt) gene. The two plasmids may be co-transfected into mammalian cells, such as Sp2/0-Ag14 cells, by electroporation and selected for hygromycin resistance. YB2/0 cell can also be used. Shitara et al., *J. Immunol. Methods* 167:271 (1994). Colonies surviving selection are expanded, and supernatant fluids monitored for production of cMN3 MAb by an ELISA method. An antibody expression level of between 0.10 and 2.5 μg/ml can be expected with this system.

Alternately, the Vκ and VH expression cassettes can be assembled in the modified staging vectors, VKpBR2 and VHpBS2, excised as XbaI/BamHI and XhoI/BamHI fragments, respectively, and subcloned into a single expression vector, such as pdHL2, as described by Gilles et al., *J. Immunol. Methods* 125:191 (1989), Losman et al., *Clin. Cancer Res.* 5:3101 (1999) and in Losman et al., *Cancer,* 80:2660 (1997) for the expression in Sp2/0-Ag14 cells. Another vector that is useful in the present invention is the GS-vector, as described in Barnes et al., *Cytotechnology* 32:109-123 (2000), which is preferably expressed in the NS0 cell line and CHO cells. Other appropriate mammalian expression systems are described in Werner et al., Arzneim.-Forsch./Drug Res. 48(II), Nr. 8, 870-880 (1998).

Preparation of a Humanized MN3 Antibody

In another preferred embodiment, the MN3 antibody is a humanized MN3 antibody (hMN3) generated by CDR grafting. Once proper human V frameworks are chosen based on the sequence homology and the sequences for the hMN3Vκ and $V_H$ domains are designed, CDR engrafting can be accomplished by gene synthesis. In most cases, the DNA encoding the Vκ or VH domain will be approximately 350 bp long. One of the construction strategies is to divide a V gene into two halves, each of which can be generated using a long synthetic DNA oligonucleotide (>140 bases) as the template and two short flanking oligonucleotides (<50 bases) as the primers in a PCR reaction. By taking advantage of codon degeneracy, a unique restriction site may easily be introduced, without changing the encoded amino acids, at regions close to the middle of the V gene DNA sequence. The short flanking oligonucleotide PCR primers can be designed with the necessary restriction sites to facilitate subsequent assembly of the full length humanized V genes from the PCR generated fragments. The Vκ DNA segment may be subcloned into a pBR327 based staging vector (VKpBR) as described by Leung et al., Hybridoma, 13:469 (1994). The VH segment may be subcloned into a similar pBluescript-based staging vector (VHpBS).

The HindIII/BamHI fragment containing the Ig promoter, leader sequence and the hMN3$V_H$ sequence can be excised from the staging vector and subcloned to the corresponding sites in a pSVgpt-based vector, pG1g, which contains the genomic sequence of the human IgG constant region, an Ig enhancer and a gpt selection marker, forming the final expression vector, hMN3pG1g. Similar strategies can be employed for the construction of the hMN3VK sequence. The restriction site chosen for the ligation of the PCR products for the long oligonucleotides can be NsiI in this case.

The DNA sequence containing the Ig promoter, leader sequence and the hMN3 Vκ sequence can be excised from the staging vector VKpBR by treatment with BamHI/HindIII, and can be subcloned into the corresponding sites of a pSVhyg-based vector, pKh, which contains the genomic sequence of human kappa chain constant regions, a hygromycin selection marker, an Ig and a kappa enhancer, forming the final expression vector, hMN3pKh.

Transfection, and assay for antibody secreting clones by ELISA, can be carried out as follows. About 10 μg of hMN3pKh (light chain expression vector) and 20 μg of hMN3pG1g (heavy chain expression vector) can be used for the transfection of 5×106 SP2/0 myeloma cells by electroporation (BioRad, Richmond, Calif.) according to Co et al., J. Immunol., 148: 1149 (1992) which is incorporated by reference. Following transfection, cells may be grown in 96-well microtiter plates in complete HSFM medium (GIBCO, Gaithersburg, Md.) at 37° C., 5% $CO_2$. The selection process can be initiated after two days by the addition of hygromycin selection medium (Calbiochem, San Diego, Calif.) at a final concentration of 500 μg/ml of hygromycin. Colonies typically emerge 2-3 weeks post-electroporation. The cultures can then be expanded for further analysis.

Alternately, the Vκ and VH expression cassettes can be assembled in the modified staging vectors, VKpBR2 and VHpBS2, excised as XbaI/BamHI and XhoI/BamHI fragments, respectively, and subcloned into a single expression vector, such as pdHL2, as described by Gilles et al., *J. Immunol. Methods* 125:191 (1989), Losman et al., *Clin. Cancer Res.* 5:3101 (1999) and in Losman et al., *Cancer,* 80:2660 (1997) for the expression in Sp2/0-Ag14 cells. Another vector that is useful in the present invention is the GS vector, as described in Barnes et al., *Cytotechnology* 32:109-123 (2000), which is preferably expressed in the NS0 cell line and CHO cells. Other appropriate mammalian expression systems are described in Werner et al., Arzneim.-Forsch./Drug Res. 48(II), Nr. 8, 870-880 (1998).

Screening the Clones and Isolating Antibodies

Transfectoma clones that are positive for the secretion of chimeric or humanized heavy chain can be identified by ELISA assay. Briefly, supernatant samples (100 μl) from transfectoma cultures are added in triplicate to ELISA microtiter plates precoated with goat anti-human (GAH)-IgG, $F(ab')_2$ fragment-specific antibody (Jackson ImmunoResearch, West Grove, Pa.). Plates are incubated for 1 h at room temperature. Unbound proteins are removed by washing three times with wash buffer (PBS containing 0.05% polysorbate 20). Horseradish peroxidase (HRP) conjugated GAH-IgG, Fc fragment-specific antibodies (Jackson ImmunoResearch, West Grove, Pa.) are added to the wells, (100 μl of antibody stock diluted×$10^4$, supplemented with the unconjugated antibody to a final concentration of 1.0 μg/ml). Following an incubation of 1 h, the plates are washed, typically three times. A reaction solution, [100 μl, containing 167 μg of orthophenylene-diamine (OPD) (Sigma, St. Louis, Mo.), 0.025% hydrogen peroxide in PBS], is added to the wells. Color is allowed to develop in the dark for 30 minutes. The reaction is stopped by the addition of 50 μl of 4 N HCl solution into each well before measuring absorbance at 490 nm in an automated ELISA reader (Bio-Tek instruments, Winooski, Vt.). Bound chimeric antibodies are than determined relative to an irrelevant chimeric antibody standard (obtainable from Scotgen, Ltd., Edinburg, Scotland).

Antibodies can be isolated from cell culture media as follows. Transfectoma cultures are adapted to serum-free medium. For production of chimeric antibody, cells are grown as a 500 ml culture in roller bottles using HSFM. Cultures are centrifuged and the supernatant filtered through a 0.2 micron membrane. The filtered medium is passed through a protein A column (1×3 cm) at a flow rate of 1 ml/min. The resin is then washed with about 10 column volumes of PBS and protein A-bound antibody is eluted from the column with 0.1 M glycine buffer (pH 3.5) containing 10 mM EDTA. Fractions of 1.0 ml are collected in tubes containing 10 μl of 3 M Tris (pH 8.6), and protein concentrations determined from the absorbencies at 280/260 nm. Peak fractions are pooled, dialyzed against PBS, and the antibody concentrated, for example, with the Centricon™ 30 (Amicon, Beverly, Mass.). The antibody concentration is determined by ELISA, as before, and its concentration adjusted to about 1 mg/ml using PBS. Sodium azide, 0.01% (w/v), is conveniently added to the sample as preservative.

The affinity of a chimeric, humanized or human MN3 antibody may be evaluated using a direct binding assay or a competitive binding assay.

Modifying/Optimizing the Recombinant Antibodies

As humanization sometimes results in a reduction or even loss of antibody affinity, additional modification might be required in order to restore the original affinity (See, for example, Tempest et al., Bio/Technology 9: 266 (1991); Verhoeyen et al., Science 239: 1534 (1988)), which are incorporated by reference. Knowing that cMN3 exhibits a binding affinity comparable to that of its murine counterpart, defective designs, if any, in the original version of cMN3 can be identified by mixing and matching the light and heavy chains of cMN3 to those of the humanized version. Preferably, some human residues in the framework regions are replaced by their murine counterparts. Also preferred, a combination of framework sequences from 2 different human antibodies, such as EU and KOL are used for $V_H$. For example, FR1-3 can come from EU and FR 4 from KOL.

Other modifications, such as Asn-linked glycosylation sites, can be introduced into a chimerized, human, or humanized MN3 antibody by conventional oligonucleotide directed site-specific mutagenesis. Detailed protocols for oligonucleotide-directed mutagenesis and related techniques for mutagenesis of cloned DNA are well known. For example, see Sambrook et al. and Ausubel et al. above.

For example, to introduce an Asn in position 18 of hMN3 Vκ (FIG. 4A), one may alter codon 18 from AGA for Arg to AAC for Asn. To accomplish this, a single stranded DNA template containing the antibody light chain sequence is prepared from a suitable strain of *E. coli* (e.g., $dut^-$, $ung^-$) in order to obtain a single strand DNA molecule containing a small number of uracils in place of thymidine. Such a DNA template can be obtained by M13 cloning or by in vitro transcription using a SP6 promoter. See, for example, Ausubel et al., eds., CURRENT PROTOCOLS IN MOLECULAR BIOLOGY, John Wiley & Sons, NY, 1987. An oligonucleotide containing the mutated sequence is synthesized conventionally, annealed to the single-stranded template and the product treated with T4 DNA polymerase and T4 DNA ligase to produce a double-stranded DNA molecule. Transformation of wild type E. ($dut^+$, $ung^+$) cells with the double-stranded DNA provides an efficient recovery of mutated DNA.

Alternatively, an Asn-linked glycosylation site can be introduced into an antibody light chain using an oligonucleotide containing the desired mutation as the primer and DNA clones of the variable regions for the Vk chain, or by using RNA from cells that produce the antibody of interest as a template. Also see, Huse, in ANTIBODY ENGINEERING: A PRACTICAL GUIDE, Boerrebaeck, ed., W. H. Freeman & Co., pp. 103-120, 1992. Site-directed mutagenesis can be performed, for example, using the TRANSFORMER™ kit (Clonetech, Palo Alto, Calif.) according to the manufacturer's instructions.

Alternatively, a glycosylation site can be introduced by synthesizing an antibody chain with mutually priming oligonucleotides, one such containing the desired mutation. See, for example, Uhlmann, Gene 71: 29 (1988); Wosnick et al., Gene 60: 115 (1988); Ausubel et al., above, which are incorporated by reference.

Although the general description above referred to the introduction of an Asn glycosylation site in position 18 of the light chain of an antibody, it will occur to the skilled artisan that it is possible to introduce Asn-linked glycosylation sites elsewhere in the light chain, or even in the heavy chain variable region.

4. Production of Antibody Fragments

Antibody fragments which recognize specific epitopes can be generated by known techniques. The antibody fragments are antigen binding portions of an antibody, such as $F(ab')_2$, Fab', Fab, Fv, sFv and the like. Other antibody fragments include, but are not limited to: the $F(ab)'_2$ fragments which can be produced by pepsin digestion of the antibody molecule and the Fab' fragments, which can be generated by reducing disulfide bridges of the $F(ab)'_2$ fragments. Alternatively, Fab' expression expression libraries can be constructed (Huse et al., 1989*, Science,* 246:1274-1281) to allow rapid and easy identification of monoclonal Fab' fragments with the desired specificity. The present invention encompasses antibodies and antibody fragments.

A single chain Fv molecule (scFv) comprises a VL domain and a VH domain. The VL and VH domains associate to form a target binding site. These two domains are further covalently linked by a peptide linker (L). A scFv molecule is denoted as either VL-L-VH if the VL domain is the N-terminal part of the scFv molecule, or as VH-L-VL if the VH domain is the N-terminal part of the scFv molecule. Methods for making scFv molecules and designing suitable peptide linkers are described in U.S. Pat. No. 4,704,692, U.S. Pat. No. 4,946,778, R. Raag and M. Whitlow, "*Single Chain Fvs*." FASEB Vol 9:73-80 (1995) and R. E. Bird and B. W. Walker, "*Single Chain Antibody Variable Regions*," TIBTECH, Vol 9: 132-137 (1991). These references are incorporated herein by reference.

To obtain high-affinity scFv, an scFv library with a large repertoire can be constructed by isolating V-genes from non-immunized human donors using PCR primers corresponding to all known $V_H$, $V_\kappa$ and $V_\lambda$ gene families. See, e.g., Vaughn et al., *Nat. Biotechnol.,* 14: 309-314 (1996). Following amplification, the $V_\kappa$ and $V_\lambda$ pools are combined to form one pool.

These fragments are ligated into a phagemid vector. The scFv linker, (Gly-Gly-Gly-Gly-Ser)$_3$, (SEQ ID NO: 35) is then ligated into the phagemid upstream of the $V_L$ fragment. The $V_H$ and linker-$V_L$ fragments are amplified and assembled on the $J_H$ region. The resulting $V_H$-linker-$V_L$ fragments are ligated into a phagemid vector. The phagemid library can be panned using filters, as described above, or using immunotubes (Nunc; Maxisorp). Similar results can be achieved by constructing a combinatorial immunoglobulin library from lymphocytes or spleen cells of immunized rabbits and by expressing the scFv constructs in *P. pastoris*. See, e.g., Ridder et al., *Biotechnology,* 13: 255-260 (1995). Additionally, following isolation of an appropriate scFv, antibody fragments with higher binding affinities and slower dissociation rates can be obtained through affinity maturation processes such as CDR3 mutagenesis and chain shuffling. See, e.g., Jackson et al., *Br. J. Cancer,* 78: 181-188 (1998); Osbourn et al., *Immunotechnology,* 2: 181-196 (1996).

An antibody fragment can be prepared by proteolytic hydrolysis of the full length antibody or by expression in *E. coli* or another host of the DNA coding for the fragment. An antibody fragment can be obtained by pepsin or papain digestion of full length antibodies by conventional methods. For example, an antibody fragment can be produced by enzymatic cleavage of antibodies with pepsin to provide a 100 Kd fragment denoted F(ab')$_2$. This fragment can be further cleaved using a thiol reducing agent, and optionally a blocking group for the sulfhydryl groups resulting from cleavage of disulfide linkages, to produce 50 Kd Fab' monovalent fragments. Alternatively, an enzymatic cleavage using papain produces two monovalent Fab fragments and an Fc fragment directly. These methods are described, for example, by Goldenberg, U.S. Pat. Nos. 4,036,945 and 4,331,647 and references contained therein, which patents are incorporated herein in their entireties by reference. Also, see Nisonoff et al., *Arch Biochem. Biophys.* 89: 230 (1960); Porter, *Biochem. J.* 73: 119 (1959), Edelman et al., in METHODS IN ENZYMOLOGY VOL. 1, page 422 (Academic Press 1967), and Coligan at pages 2.8.1-2.8.10 and 2.10.-2.10.4.

Another form of an antibody fragment is a peptide coding for a single complementarity-determining region (CDR). A CDR is a segment of the variable region of an antibody that is complementary in structure to the epitope to which the antibody binds and is more variable than the rest of the variable region. Accordingly, a CDR is sometimes referred to as hypervariable region. A variable region comprises three CDRs. CDR peptides can be obtained by constructing genes encoding the CDR of an antibody of interest. Such genes are prepared, for example, by using the polymerase chain reaction to synthesize the variable region from RNA of antibody-producing cells. See, for example, Larrick et al., *Methods: A Companion to Methods in Enzymology* 2: 106 (1991); Courtenay-Luck, "Genetic Manipulation of Monoclonal Antibodies," in MONOCLONAL ANTIBODIES: PRODUCTION, ENGINEERING AND CLINICAL APPLICATION, Ritter et al. (eds.), pages 166-179 (Cambridge University Press 1995); and Ward et al., "Genetic Manipulation and Expression of Antibodies," in MONOCLONAL ANTIBODIES: PRINCIPLES AND APPLICATIONS, Birch et al., (eds.), pages 137-185 (Wiley-Liss, Inc. 1995).

Other methods of cleaving antibodies, such as separation of heavy chains to form monovalent light-heavy chain fragments, further cleavage of fragments, or other enzymatic, chemical or genetic techniques may also be used, so long as the fragments bind to the antigen that is recognized by the intact antibody.

5. Fusion Proteins

The antibody fusion proteins of the present invention comprise two or more antibodies or fragments thereof and each of the antibodies that compose this fusion protein can contain a therapeutic agent or diagnostic agent. In other words, the antibody fusion protein or fragment thereof can comprise at least one first MN3 MAb or fragment thereof and at least one second MAb or fragment thereof that is not an MN3 MAb. In a preferred embodiment, the MN3 antibody or fragment thereof is an MN3 antibody or fragment thereof. Preferably, the second MAb is a granulocyte associated antibody, such as an antibody against MAbs reactive with NCA-90, NCA-95, CD15, CD33, and from the MAbs MN2, MN3, MN-15, NP-1, NP-2, BW 250/183, and MAb 47, or a combination thereof.

Additionally, one or more of the antibodies or fragments thereof that comprise the antibody fusion protein can have at least one therapeutic or diagnostic/detection agent attached. Further, the diagnostic/detection agents or therapeutic agents need not be the same but can be different therapeutic agents; for example, one can attach a drug and a radioisotope to the same fusion protein. Particulary, an IgG can be radiolabeled with $^{131}$I and attached to a drug. The $^{131}$I can be incorporated into the tyrosine of the IgG and the drug attached to the epsilon amino group of the IgG lysines. Both therapeutic and diagnostic agents also can be attached to reduced SH groups and to the carbohydrate side chains.

Also preferred, the antibody fusion protein of the present invention comprises at least two MN3 monoclonal antibodies or fragments thereof, and these may be to different epitopes of a granulocyte antigen, such as those recognized by MN3, or of different human immunoglobulin backbone sequences (or IgGs). Preferably, the antibodies or fragments there of are MN3 antibodies or fragments thereof.

Multispecific and Multivalent Antibodies

The MN3 antibodies and fragments thereof of the present invention, as well as other antibodies with different specificities for use in combination therapy, can be made as a multispecific antibody, comprising at least one binding site to an antigen recognized by MN3 and at least one binding site to another antigen, or a multivalent antibody comprising multiple binding sites to the same epitope or antigen. In a preferred embodiment, the multispecific antibody or fragment thereof comprises at least one binding site to an MN3 epitope and at least one binding site that is not to an antigen recognized by MN3. Also preferred, the multispecific antibody or fragment thereof comprises at least one binding site to an MN3 epitope and at least one binding site to a different epitope on an antigen recognized by MN3.

The present invention provides a bispecific antibody or antibody fragment having at least one binding region that specifically binds an antigen recognized by MN3 and at least one other binding region that specifically binds another targeted cell marker or a targetable conjugate. The targetable conjugate comprises a carrier portion which comprises or bears at least one epitope recognized by at least one binding region of the bispecific antibody or antibody fragment. Preferably, the bispecific antibody binds to an MN3 epitope.

A variety of recombinant methods can be used to produce bi-specific antibodies and antibody fragments. For example, bi-specific antibodies and antibody fragments can be produced in the milk of transgenic livestock. See, e.g., Colman, A., *Biochem. Soc. Symp.,* 63: 141-147, 1998; U.S. Pat. No. 5,827,690. Two DNA constructs are prepared which contain, respectively, DNA segments encoding paired immunoglobulin heavy and light chains. The fragments are cloned into expression vectors which contain a promoter sequence that is preferentially expressed in mammary epithelial cells. Examples include, but are not limited to, promoters from rabbit, cow and sheep casein genes, the cow α-lactoglobulin gene, the sheep β-lactoglobulin gene and the mouse whey acid protein gene. Preferably, the inserted fragment is flanked on its 3' side by cognate genomic sequences from a mammary-specific gene. This provides a polyadenylation site and transcript-stabilizing sequences. The expression cassettes are coinjected into the pronuclei of fertilized, mammalian eggs, which are then implanted into the uterus of a recipient female and allowed to gestate. After birth, the progeny are screened for the presence of both transgenes by Southern analysis. In order for the antibody to be present, both heavy and light chain genes must be expressed concurrently in the same cell. Milk from transgenic females is analyzed for the presence and functionality of the antibody or antibody fragment using standard immunological methods known in the art. The antibody can be purified from the milk using standard methods known in the art.

Other recent methods for producing bsAbs include engineered recombinant Abs which have additional cysteine residues so that they crosslink more strongly than the more common immunoglobulin isotypes. See, e.g., FitzGerald et al., Protein Eng. 10(10):1221-1225, 1997. Another approach is to engineer recombinant fusion proteins linking two or more different single-chain antibody or antibody fragment segments with the needed dual specificities. See, e.g., Coloma et al., *Nature Biotech.* 15:159-163, 1997. A variety of bi-specific fusion proteins can be produced using molecular engineering. In one form, the bi-specific fusion protein is monovalent, consisting of, for example, a scFv with a single binding site for one antigen and a Fab fragment with a single binding site for a second antigen. In another form, the bi-specific fusion protein is divalent, consisting of, for example, an IgG with two binding sites for one antigen and two scFv with two binding sites for a second antigen.

An MN3 multivalent antibody or fragment thereof is also contemplated in the present invention. Preferably, the MN3 multivalent antibody or fragment thereof is a humanized MN3 multivalent antibody or fragment thereof. This multivalent antibody is constructed by association of a first and a second polypeptide. The first polypeptide comprises a first single chain Fv molecule covalently linked to a first immunoglobulin-like domain which preferably is an immunoglobulin light chain variable region domain. The second polypeptide comprises a second single chain Fv molecule covalently linked to a second immunoglobulin-like domain which preferably is an immunoglobulin heavy chain variable region domain. Each of the first and second single chain Fv molecules forms a target binding site, and the first and second immunoglobulin-like domains associate to form a third target binding site.

A single chain Fv molecule with the VL-L-VH configuration, wherein L is a linker, may associate with another single chain Fv molecule with the VH-L-VL configuration to form a bivalent dimer. In this case, the VL domain of the first scFv and the VH domain of the second scFv molecule associate to form one target binding site, while the VH domain of the first scFv and the VL domain of the second scFv associate to form the other target binding site.

Another embodiment of the present invention is an MN3 bispecific, trivalent antibody comprising two heterologous polypeptide chains associated non-covalently to form three binding sites, two of which have affinity for one target and a third which has affinity for a hapten that can be made and attached to a carrier for a diagnostic and/or therapeutic agent. Preferably, the antibody has two MN3 binding sites and one other binding site. The bispecific, trivalent targeting agents have two different scFvs, one scFv contains two $V_H$ domains from one antibody connected by a short linker to the $V_L$ domain of another antibody and the second scFv contains two $V_L$ domains from the first antibody connected by a short linker to the $V_H$ domain of the other antibody. The methods for generating multivalent, multispecific agents from $V_H$ and $V_L$ domains provide that individual chains synthesized from a DNA plasmid in a host organism are composed entirely of $V_H$ domains (the $V_H$-chain) or entirely of $V_L$ domains (the $V_L$-chain) in such a way that any agent of multivalency and multispecificity can be produced by non-covalent association of one $V_H$-chain with one $V_L$-chain. For example, forming a trivalent, trispecific agent, the $V_H$-chain will consist of the amino acid sequences of three $V_H$ domains, each from an antibody of different specificity, joined by peptide linkers of variable lengths, and the $V_L$-chain will consist of complementary $V_L$ domains, joined by peptide linkers similar to those used for the $V_H$-chain. Since the $V_H$ and $V_L$ domains of antibodies associate in an anti-parallel fashion, the preferred method in this invention has the $V_L$ domains in the $V_L$-chain arranged in the reverse order of the $V_H$ domains in the $V_H$-chain.

Diabodies, Triabodies and Tetrabodies

The MN3 antibodies and fragments thereof of the present invention can also be used to prepare functional bispecific single-chain antibodies (bscAb), also called diabodies, and can be produced in mammalian cells using recombinant methods. See, e.g., Mack et al., *Proc. Natl. Acad. Sci.,* 92: 7021-7025, 1995, incorporated. For example, bscAb are produced by joining two single-chain Fv fragments via a glycine-serine linker using recombinant methods. The V light-chain ($V_L$) and V heavy-chain ($V_H$) domains of two antibodies of interest are isolated using standard PCR methods. The $V_L$ and $V_H$ cDNA's obtained from each hybridoma are then joined to form a single-chain fragment in a two-step fusion PCR. The first PCR step introduces the $(Gly_4\text{-}Ser_1)_3$ linker, (SEQ ID NO: 35) and the second step joins the $V_L$ and $V_H$ amplicons. Each single chain molecule is then cloned into a bacterial expression vector. Following amplification, one of the single-chain molecules is excised and sub-cloned into the other vector, containing the second single-chain molecule of interest. The resulting bscAb fragment is subcloned into an eukaryotic expression vector. Functional protein expression can be obtained by transfecting the vector into chinese hamster ovary cells. Bispecific fusion proteins are prepared in a similar manner. Bispecific single-chain antibodies and bispecific fusion proteins are included within the scope of the present invention.

For example, a humanized, chimeric or human or murine MN3 monoclonal antibody can be used to produce antigen specific diabodies, triabodies, and tetrabodies. The monospecific diabodies, triabodies, and tetrabodies bind selectively to targeted antigens and as the number of binding sites on the molecule increases, the affinity for the target cell increases and a longer residence time is observed at the desired location. For diabodies, the two chains comprising the $V_H$ polypeptide of the humanized MN3 MAb connected to the $V_K$ polypeptide of the humanized MN3 MAb by a five amino acid residue linker are utilized. Each chain forms one half of the humanized MN3 diabody. In the case of triabodies, the three chains comprising $V_H$ polypeptide of the humanized MN3

MAb connected to the $V_K$ polypeptide of the humanized MN3 MAb by no linker are utilized. Each chain forms one third of the hMN3 triabody.

Also contemplated in the present invention is a bi-specific antibody or antibody fragment having at least one arm that is reactive against a targeted tissue or cell, such as granulocytes, and at least one other arm that is reactive against a targetable construct. Preferably, one arm of the bispecific antibody binds an antigen recognized by MN3. The targetable construct is comprised of a carrier portion and at least 2 units of a recognizable hapten. Examples of recognizable haptens include, but are not limited to, histamine succinoyl glycine (HSG) and fluorescein isothiocyanate. The targetable construct may be conjugated to a variety of agents useful for treating or identifying diseased tissue. The targetable construct can be of diverse structure, but is selected not only to avoid eliciting an immune responses, but also for rapid in vivo clearance when used within the bsAb targeting method. Hydrophobic agents are best at eliciting strong immune responses, whereas hydrophilic agents are preferred for rapid in vivo clearance; thus, a balance between hydrophobic and hydrophilic needs to be established. This is accomplished, in part, by relying on the use of hydrophilic chelating agents to offset the inherent hydrophobicity of many organic moieties. Also, subunits of the targetable construct may be chosen which have opposite solution properties, for example, peptides, which contain amino acids, some of which are hydrophobic and some of which are hydrophilic. Aside from peptides, carbohydrates may be used.

Large quantities of bscAb and fusion proteins can be produced using *Escherichia coli* expression systems. See, e.g., Zhenping et al., *Biotechnology,* 14: 192-196, 1996. A functional bscAb can be produced by the coexpression in *E. coli* of two "cross-over" scFv fragments in which the $V_L$ and $V_H$ domains for the two fragments are present on different polypeptide chains. The V light-chain ($V_L$) and V heavy-chain ($V_H$) domains of two antibodies of interest are isolated using standard PCR methods. The cDNA's are then ligated into a bacterial expression vector such that C-terminus of the $V_L$ domain of the first antibody of interest is ligated via a linker to the N-terminus of the $V_H$ domain of the second antibody. Similarly, the C-terminus of the $V_L$ domain of the second antibody of interest is ligated via a linker to the N-terminus of the $V_H$ domain of the first antibody. The resulting dicistronic operon is placed under transcriptional control of a strong promoter, e.g., the *E. coli* alkaline phosphatase promoter which is inducible by phosphate starvation. Alternatively, single-chain fusion constructs have successfully been expressed in *E. coli* using the lac promoter and a medium consisting of 2% glycine and 1% Triton X-100. See, e.g., Yang et al., *Appl. Environ. Microbiol*., 64: 2869-2874, 1998. An *E. coli*, heat-stable, enterotoxin II signal sequence is used to direct the peptides to the periplasmic space. After secretion, the two peptide chains associate to form a non-covalent heterodimer which possesses both antigen binding specificities. The bscAb is purified using standard procedures known in the art, e.g., *Staphylococcal* protein A chromatography.

Functional bscAbs and fusion proteins also can be produced in the milk of transgenic livestock. See, e.g., Colman, A., *Biochem. Soc. Symp.,* 63: 141-147, 1998; U.S. Pat. No. 5,827,690. The bscAb fragment, obtained as described above, is cloned into an expression vector containing a promoter sequence that is preferentially expressed in mammary epithelial cells. Examples include, but are not limited to, promoters from rabbit, cow and sheep casein genes, the cow α-lactoglobulin gene, the sheep β-lactoglobulin gene and the mouse whey acid protein gene. Preferably, the inserted bscAb is flanked on its 3' side by cognate genomic sequences from a mammary-specific gene. This provides a polyadenylation site and transcript-stabilizing sequences. The expression cassette is then injected into the pronuclei of fertilized, mammalian eggs, which are then implanted into the uterus of a recipient female and allowed to gestate. After birth, the progeny are screened for the presence of the introduced DNA by Southern analysis. Milk from transgenic females is analyzed for the presence and functionality of the bscAb using standard immunological methods known in the art. The bscAb can be purified from the milk using standard methods known in the art. Transgenic production of bscAb in milk provides an efficient method for obtaining large quantities of bscAb.

Functional bscAb and fusion proteins also can be produced in transgenic plants. See, e.g., Fiedler et al., *Biotech.,* 13: 1090-1093, 1995; Fiedler et al., *Immunotechnology,* 3: 205-216, 1997. Such production offers several advantages including low cost, large scale output and stable, long term storage. The bscAb fragment, obtained as described above, is cloned into an expression vector containing a promoter sequence and encoding a signal peptide sequence, to direct the protein to the endoplasmic reticulum. A variety of promoters can be utilized, allowing the practitioner to direct the expression product to particular locations within the plant. For example, ubiquitous expression in tobacco plants can be achieved by using the strong cauliflower mosaic virus 35S promoter, while organ specific expression is achieved via the seed specific legumin B4 promoter. The expression cassette is transformed according to standard methods known in the art. Transformation is verified by Southern analysis. Transgenic plants are analyzed for the presence and functionality of the bscAb using standard immunological methods known in the art. The bscAb can be purified from the plant tissues using standard methods known in the art.

Additionally, transgenic plants facilitate long term storage of bscAb and fusion proteins. Functionally active scFv proteins have been extracted from tobacco leaves after a week of storage at room temperature. Similarly, transgenic tobacco seeds stored for 1 year at room temperature show no loss of scFv protein or its antigen binding activity.

Functional bscAb and fusion proteins also can be produced in insect cells. See, e.g., Mahiouz et al., *J. Immunol. Methods,* 212: 149-160 (1998). Insect-based expression systems provide a means of producing large quantities of homogenous and properly folded bscAb. The baculovirus is a widely used expression vector for insect cells and has been successfully applied to recombinant antibody molecules. See, e.g., Miller, L. K., *Ann. Rev. Microbiol.,* 42: 177 (1988); Bei et al., *J. Immunol. Methods,* 186: 245 (1995). Alternatively, an inducible expression system can be utilized by generating a stable insect cell line containing the bscAb construct under the transcriptional control of an inducible promoter. See, e.g., Mahiouz et al., *J. Immunol. Methods,* 212: 149-160 (1998). The bscAb fragment, obtained as described above, is cloned into an expression vector containing the *Drosphila* metallothionein promoter and the human HLA-A2 leader sequence. The construct is then transfected into *D. melanogaster* SC-2 cells. Expression is induced by exposing the cells to elevated amounts of copper, zinc or cadmium. The presence and functionality of the bscAb is determined using standard immunological methods known in the art. Purified bscAb is obtained using standard methods known in the art.

The ultimate use of the bispecific diabodies described herein is for pre-targeting MN3 positive tumors for subsequent specific delivery of diagnostic/detection or therapeutic agents. These diabodies bind selectively to targeted antigens allowing for increased affinity and a longer residence time at the desired location. Moreover, non-antigen bound diabodies are cleared from the body quickly and exposure of normal tissues is minimized. The diagnostic/detection and therapeutic agents can include isotopes, drugs, toxins, cytokines, hormones, growth factors, conjugates, radionuclides, and metals. For example, gadolinium metal is used for magnetic resonance imaging (MRI). Examples of radionuclides are $^{225}$Ac, $^{18}$F, $^{68}$Ga, $^{67}$Ga, $^{90}$Y, $^{86}$Y, $^{111}$In, $^{131}$I, $^{125}$I, $^{123}$I, $^{99m}$Tc, $^{94m}$Tc, $^{186}$Re, $^{188}$Re, $^{177}$Lu, $^{62}$Cu, $^{64}$Cu, $^{67}$Cu, $^{212}$Bi, $^{213}$Bi, $^{32}$P, $^{11}$C, $^{13}$N, $^{15}$O, $^{76}$Br, and $^{211}$At. Other radionuclides are also available as diagnostic and therapeutic agents, especially those in the energy range of 60 to 4,000 keV.

More recently, a tetravalent tandem diabody (termed tandab) with dual specificity has also been reported (Cochlovius et al., Cancer Research (2000) 60: 4336-4341). The bispecific tandab is a dimer of two identical polypeptides, each containing four variable domains of two different antibodies ($V_{H1}$, $V_{L1}$, $V_{H2}$, $V_{L2}$) linked in an orientation to facilitate the formation of two potential binding sites for each of the two different specificities upon self-association.

7. MN3 Immunoconjugates

Any of the MN3 antibodies or fragments thereof, or antibody fusion proteins or fragments thereof of the present invention can be conjugated with one or more therapeutic and/or diagnostic/detection agents. Generally, one therapeutic or diagnostic/detection agent is attached to each antibody or antibody fragment but more than one therapeutic agent or diagnostic agent can be attached to the same antibody, fusion protein, or fragment thereof. Such a therapeutic or diagnostic/detection agent may be a peptide which bears a diagnostic/detection or therapeutic agent. An immunoconjugate retains the immunoreactivity of the antibody component, i.e., the antibody moiety has about the same or slightly reduced ability to bind the cognate antigen after conjugation as before conjugation.

A wide variety of diagnostic/detection and therapeutic agents can be advantageously conjugated to the antibody, fusion protein, or fragment thereof of the present invention. In a preferred embodiment, the diagnostic/detection agents are selected from the group consisting of radioisotopes for nuclear imaging, intraoperative and endoscopic detection, enhancing agents for use in magnetic resonance imaging or in ultrasonography, radiopaque and contrast agents for X-rays and computed tomography, and fluorescent compounds for fluoroscopy, including endoscopic fluoroscopy. Fluorescent and radioactive agents conjugated to antibodies or used in bispecific, pretargeting methods, are particularly useful for endoscopic, intraoperative or intravascular detection of the targeted antigens associated with diseased tissues or clusters of cells, such as malignant tumors, as disclosed in Goldenberg U.S. Pat. Nos. 5,716,595, 6,096,289 and U.S. application Ser. No. 09/348,818, incorporated herein by reference in their entirety, particularly with gamma-, beta-, and positron-emitters. Radionuclides useful for positron emission tomography include, but are not limited to: F-18, Mn-51, Mn-52m, Fe-52, Co-55, Cu-62, Cu-64, Ga-68, As-72, Br-75, Br-76, Rb-82m, Sr-83, Y-86, Zr-89, Tc-94m, In-110, I-120, and I-124.

The therapeutic agents recited here are those agents that also are useful for administration separately with a naked antibody, as described herein. Therapeutic agents include, for example, chemotherapeutic drugs such as vinca alkaloids and other alkaloids, anthracyclines, epidophyllotoxins, taxanes, antimetabolites, alkylating agents, antibiotics, COX-2 inhibitors, antimitotics, antiangiogenic and apoptotoic agents, particularly doxorubicin, methotrexate, taxol, CPT-11, camptothecans, and others from these and other classes of anticancer agents, and the like. Other useful cancer chemotherapeutic drugs for the preparation of immunoconjugates and antibody fusion proteins include nitrogen mustards, alkyl sulfonates, nitrosoureas, triazenes, folic acid analogs, pyrimidine analogs, purine analogs, platinum coordination complexes, hormones, toxins (e.g., RNAse, *Pseudomonas* exotoxin), and the like. Suitable chemotherapeutic agents are described in REMINGTON'S PHARMACEUTICAL SCIENCES, 19th Ed. (Mack Publishing Co. 1995), and in GOODMAN AND GILMAN'S THE PHARMACOLOGICAL BASIS OF THERAPEUTICS, 7th Ed. (MacMillan Publishing Co. 1985), as well as revised editions of these publications. Other suitable chemotherapeutic agents, such as experimental drugs, are known to those of skill in the art.

A toxin, such as *Pseudomonas* exotoxin, may also be complexed to or form the therapeutic agent portion of an immunoconjugate of the MN3 antibody or fragment thereof of the present invention. Additionally, the toxin may be used in combination with a naked chimeric, humanized or human MN3 antibody or fragment thereof, an MN3 fusion protein or fragment thereof, or a MN3 antibody or fragment thereof conjugated to a different therapeutic agent. Other toxins suitably employed in the preparation of such conjugates or other fusion proteins, include ricin, abrin, ribonuclease (RNase), DNase I, *Staphylococcal* enterotoxin-A, pokeweed antiviral protein, gelonin, diphtherin toxin, *Pseudomonas* exotoxin, and *Pseudomonas* endotoxin. See, for example, Pastan et al., *Cell* 47:641 (1986), and Goldenberg, CA—*A Cancer Journal for Clinicians* 44:43 (1994). Additional toxins suitable for use in the present invention are known to those of skill in the art and are disclosed in U.S. Pat. No. 6,077,499, which is incorporated in its entirety by reference. These can be derived, for example, from animal, plant and microbial sources, or chemically or recombinantly engineered. The toxin can be a plant, microbial, or animal toxin, or a synthetic variation thereof.

An immunomodulator, such as a cytokine may also be conjugated to, or form the therapeutic agent portion of the MN3 immunoconjugate, or be administered unconjugated to the chimeric, humanized or human MN3 antibody, fusion protein, or fragment thereof of the present invention. As used herein, the term "immunomodulator" includes cytokines, stem cell growth factors, lymphotoxins, such as tumor necrosis factor (TNF), and hematopoietic factors, such as interleukins (e.g., interleukin-1 (IL-1), IL-2, IL-3, IL-6, IL-10, IL-12, IL-18 and IL-21), colony stimulating factors (e.g., granulocyte-colony stimulating factor (G-CSF) and granulocyte macrophage-colony stimulating factor (GM-CSF)), interferons (e.g., interferons-α, -β and -γ), the stem cell growth factor designated "S1 factor," erythropoietin and thrombopoietin. Examples of suitable immunomodulator moieties include IL-2, IL-6, IL-10, IL-12, IL-18, IL-21, interferon-γ, TNF-α, and the like. Alternatively, subjects can receive a naked MN3 antibody or fragment thereof, or naked fusion protein or fragment thereof, and a separately administered cytokine, which can be administered before, concurrently or after administration of the naked MN3 antibody or fragment, or naked MN3 fusion protein or fragment thereof. The MN3 antibody or fragment there or fusion protein or fragment thereof of may also be conjugated to an immunomodulator. The immunomodulator may also be conjugated to a hybrid antibody consisting of one or more antibodies or antibody fragments binding to different antigens. Such an antigen may also be an immunomodulator. For example, CD40 or other immunomodulators may be administered in combination with a MN3 antibody or fragment thereof either together, before or after the antibody combinations are administered.

Furthermore, an MN3 antibody or fragment thereof, or fusion protein or fragment thereof may comprise a γ-emitting radionuclide or a positron-emitter useful for diagnostic imaging. Examples of diagnostic/detection agents include diverse labels, radionuclides, chelators, dyes, contrast agents, fluorescent compounds, chromagens, and other marker moieties. Radionuclides useful for positron emission tomography include, but are not limited to: $^{18}$F, $^{51}$Mn, $^{52m}$Mn, $^{52}$Fe, $^{55}$Co, $^{62}$Cu, $^{64}$Cu, $^{68}$Ga, $^{72}$As, $^{75}$Br, $^{76}$Br, $^{82m}$Rb, $^{83}$Sr, $^{86}$Y, $^{89}$Zr, $^{94m}$Tc, $^{110}$In, $^{120}$I, and $^{124}$I. Total decay energies of useful positron-emitting radionuclides are preferably <2,000 keV, more preferably under 1,000 keV, and most preferably <700 keV. Radionuclides useful as diagnostic agents utilizing gamma-ray detection include, but are not limited to: Cr-51, Co-57, Co-58, Fe-59, Cu-67, Ga-67, Se-75, Ru-97, Tc-99m, In-111, In-114m, I-123, I-125, I-131, Yb-169, Hg-197, and Tl-201. Decay energies of useful gamma-ray emitting radionuclides are preferably 20-2000 keV, more preferably 60-600 keV, and most preferably 100-300 keV.

Additionally, radionuclides suitable for treating a diseased tissue include, but are not limited to, P-32, P-33, Sc-47, Fe-59, Cu-64, Cu-67, Se-75, As-77, Sr-89, Y-90, Mo-99, Rh-105, Pd-109, Ag-111, I-125, I-131, Pr-142, Pr-143, Pm-149, Sm-153, Tb-161, Ho-166, Er-169, Lu-177, Re-186, Re-188, Re-189, Ir-194, Au-198, Au-199, Pb-211, Pb-212, and Bi-213, Co-58, Ga-67, Br-80m, Tc-99m, Rh-103m, Pt-109, In-111, Sb-119, I-125, Ho-161, Os-189m, Ir-192, Dy-152, At-211, Bi-212, Ra-223, Rn-219, Po-215, Bi-211, Ac-225, Fr-221, At-217, Bi-213, Fm-255 and combinations thereof.

Suitable diagnostic imaging isotopes are usually in the range of 20 to 2,000 keV, while suitable therapeutic radionuclides are usually in the range of 20 to 10,000 keV. See for example, U.S. patent application entitled "Labeling Targeting Agents with Gallium-68"—Inventors G. L. Griffiths and W. J. McBride, (U.S. Provisional Application No. 60/342,104), which discloses positron emitters, such as $^{18}$F, $^{68}$Ga, $^{94m}$Tc. and the like, for imaging purposes and which is incorporated in its entirety by reference. A suitable radionuclide is an Auger emitter, and preferably has an energy of less than 1000 keV. Also preferred is a β emitter and has an energy between 20 and 5000 keV or an alpha emitter and has an energy between 2000 and 10,000 keV.

A therapeutic or diagnostic/detection agent can be attached at the hinge region of a reduced antibody component via disulfide bond formation. As an alternative, such peptides can be attached to the antibody component using a heterobifunctional cross-linker, such as N-succinyl 3-(2-pyridyldithio) proprionate (SPDP). Yu et al., *Int. J. Cancer* 56: 244 (1994). General techniques for such conjugation are well known in the art. See, for example, Wong, CHEMISTRY OF PROTEIN CONJUGATION AND CROSS-LINKING (CRC Press 1991); Upeslacis et al., "Modification of Antibodies by Chemical Methods," in MONOCLONAL ANTIBODIES: PRINCIPLES AND APPLICATIONS, Birch et al. (eds.), pages 187-230 (Wiley-Liss, Inc. 1995); Price, "Production and Characterization of Synthetic Peptide-Derived Antibodies," in MONOCLONAL ANTIBODIES: PRODUCTION, ENGINEERING AND CLINICAL APPLICATION, Ritter et al. (eds.), pages 60-84 (Cambridge University Press 1995). Alternatively, the therapeutic or diagnostic agent can be conjugated via a carbohydrate moiety in the Fc region of the antibody. The carbohydrate group can be used to increase the loading of the same peptide that is bound to a thiol group, or the carbohydrate moiety can be used to bind a different peptide.

Methods for conjugating peptides to antibody components via an antibody carbohydrate moiety are well known to those of skill in the art. See, for example, Shih et al., *Int. J. Cancer* 41: 832 (1988); Shih et al., *Int. J. Cancer* 46: 1101 (1990); and Shih et al., U.S. Pat. No. 5,057,313, all of which are incorporated in their entirety by reference. The general method involves reacting an antibody component having an oxidized carbohydrate portion with a carrier polymer that has at least one free amine function and that is loaded with a plurality of peptide. This reaction results in an initial Schiff base (imine) linkage, which can be stabilized by reduction to a secondary amine to form the final conjugate.

However, if the Fc region is absent, for example, if the antibody used as the antibody component of the immunoconjugate is an antibody fragment, it is still possible to attach a diagnostic/detection a therapeutic agent. A carbohydrate moiety can be introduced into the light chain variable region of a full-length antibody or antibody fragment. See, for example, Leung et al., *J. Immunol.* 154: 5919 (1995); Hansen et al., U.S. Pat. No. 5,443,953 (1995), Leung et al., U.S. Pat. No. 6,254,868, all of which are incorporated in their entirety by reference. The engineered carbohydrate moiety is used to attach the therapeutic or diagnostic agent.

Targetable Constructs

The targetable construct can be of diverse structure, but is selected not only to avoid eliciting an immune responses, but also for rapid in vivo clearance when used within the bsAb targeting method. Hydrophobic agents are best at eliciting strong immune responses, whereas hydrophilic agents are preferred for rapid in vivo clearance; thus, a balance between hydrophobic and hydrophilic needs to be established. This is accomplished, in part, by relying on the use of hydrophilic chelating agents to offset the inherent hydrophobicity of many organic moieties. Also, subunits of the targetable construct may be chosen which have opposite solution properties, for example, peptides, which contain amino acids, some of which are hydrophobic and some of which are hydrophilic. Aside from peptides, carbohydrates may be used.

Peptides having as few as two amino-acid residues may be used, preferably two to ten residues, if also coupled to other moieties such as chelating agents. The linker should be a low molecular weight conjugate, preferably having a molecular weight of less than 50,000 daltons, and advantageously less than about 20,000 daltons, 10,000 daltons or 5,000 daltons, including the metal ions in the chelates. For instance, the known peptide DTPA-Tyr-Lys(DTPA)-OH (wherein DTPA is diethylenetriaminepentaacetic acid) has been used to generate antibodies against the indium-DTPA portion of the molecule. However, by use of the non-indium-containing molecule, and appropriate screening steps, new Abs against the tyrosyl-lysine dipeptide can be made. More usually, the antigenic peptide will have four or more residues, such as the peptide DOTA-Phe-Lys(HSG)-Tyr-Lys(HSG)-$NH_2$ (SEQ ID NO: 7), wherein DOTA is 1,4,7,10-tetraazacyclododecanetetraacetic acid and HSG is the histamine succinoyl glycyl group of the formula:

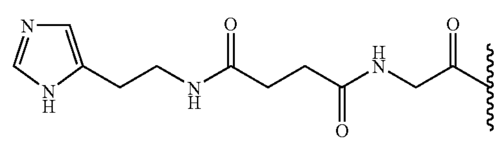

The non-metal-containing peptide may be used as an immunogen, with resultant Abs screened for reactivity against the Phe-Lys-Tyr-Lys (SEQ ID NO: 36) backbone.

The invention also contemplates the incorporation of unnatural amino acids, e.g., D-amino acids, into the backbone structure to ensure that, when used with the final bsAb/linker system, the arm of the bsAb which recognizes the linker moiety is completely specific. The invention further contemplates other backbone structures such as those constructed from non-natural amino acids and peptoids. Examples of targetable constructs that have D-amino acid backbones that can be used with the present methods include those disclosed in U.S. Patent Application No. 60/478,403.

The peptides to be used as immunogens are synthesized conveniently on an automated peptide synthesizer using a solid-phase support and standard techniques of repetitive orthogonal deprotection and coupling. Free amino groups in the peptide, that are to be used later for chelate conjugation, are advantageously blocked with standard protecting groups such as an acetyl group. Such protecting groups will be known to the skilled artisan. See Greene and Wuts *Protective Groups in Organic Synthesis,* 1999 (John Wiley and Sons, N.Y.). When the peptides are prepared for later use within the bsAb system, they are advantageously cleaved from the resins to generate the corresponding C-terminal amides, in order to inhibit in vivo carboxypeptidase activity.

The haptens of the immunogen comprise an immunogenic recognition moiety, for example, a chemical hapten. Using a chemical hapten, preferably the HSG hapten, high specificity of the linker for the antibody is exhibited. This occurs because antibodies raised to the HSG hapten are known and can be easily incorporated into the appropriate bispecific antibody. Thus, binding of the linker with the attached hapten would be highly specific for the antibody or antibody fragment.

Chelate Moieties

The presence of hydrophilic chelate moieties on the linker moieties helps to ensure rapid in vivo clearance. In addition to hydrophilicity, chelators are chosen for their metal-binding properties, and are changed at will since, at least for those linkers whose bsAb epitope is part of the peptide or is a non-chelate chemical hapten, recognition of the metal-chelate complex is no longer an issue.

A chelator such as DTPA, DOTA, TETA, or NOTA or a suitable peptide, to which a detectable label, such as a fluorescent molecule, or cytotoxic agent, such as a heavy metal or radionuclide, can be conjugated. For example, a therapeutically useful immunoconjugate can be obtained by conjugating a photoactive agent or dye to an antibody fusion protein. Fluorescent compositions, such as fluorochrome, and other chromogens, or dyes, such as porphyrins sensitive to visible light, have been used to detect and to treat lesions by directing the suitable light to the lesion. In therapy, this has been termed photoradiation, phototherapy, or photodynamic therapy (Jori et al. (eds.), PHOTODYNAMIC THERAPY OF TUMORS AND OTHER DISEASES (Libreria Progetto 1985); van den Bergh, *Chem. Britain* 22:430 (1986)). Moreover, monoclonal antibodies have been coupled with photoactivated dyes for achieving phototherapy. Mew et al., *J. Immunol.* 130:1473 (1983); idem., *Cancer Res.* 45:4380 (1985); Oseroffet al., *Proc. Natl. Acad. Sci. USA* 83:8744 (1986); idem., *Photochem. Photobiol.* 46:83 (1987); Hasan et al., *Prog. Clin. Biol. Res.* 288:471 (1989); Tatsuta et al., *Lasers Surg. Med.* 9:422 (1989); Pelegrin et al., *Cancer* 67:2529 (1991). However, these earlier studies did not include use of endoscopic therapy applications, especially with the use of antibody fragments or subfragments. Thus, the present invention contemplates the therapeutic use of immunoconjugates comprising photoactive agents or dyes.

Particularly useful metal-chelate combinations include 2-benzyl-DTPA and its monomethyl and cyclohexyl analogs, used with $^{47}$Sc, $^{52}$Fe, $^{55}$Co, $^{67}$Ga, $^{68}$Ga, $^{111}$In, $^{89}$Zr, $^{90}$Y, $^{161}$Tb, $^{177}$Lu, $^{212}$Bi, $^{213}$Bi, and $^{225}$Ac for radio-imaging and RAIT. The same chelators, when complexed with non-radioactive metals, such as Mn, Fe and Gd can be used for MRI, when used along with the bsAbs of the invention. Macrocyclic chelators such as NOTA (1,4,7-triaza-cyclononane-N,N',N"-triacetic acid), DOTA, and TETA (p-bromoacetamido-benzyl-tetraethylaminetetraacetic acid) are of use with a variety of metals and radiometals, most particularly with radionuclides of Ga, Y and Cu, respectively.

DTPA and DOTA-type chelators, where the ligand includes hard base chelating functions such as carboxylate or amine groups, are most effective for chelating hard acid cations, especially Group Ia and Group IIIa metal cations. Such metal-chelate complexes can be made very stable by tailoring the ring size to the metal of interest. Other ring-type chelators such as macrocyclic polyethers are of interest for stably binding nuclides such as $^{223}$Ra for RAIT. Porphyrin chelators may be used with numerous radiometals, and are also useful as certain cold metal complexes for bsAb-directed immuno-phototherapy. More than one type of chelator may be conjugated to a carrier to bind multiple metal ions, e.g., cold ions, diagnostic radionuclides and/or therapeutic radionuclides. Particularly useful therapeutic radionuclides include, but are not limited to, $^{32}$P, $^{33}$P, $^{47}$Sc, $^{64}$Cu, $^{67}$Cu, $^{67}$Ga, $^{90}$Y, $^{111}$Ag, $^{111}$In, $^{125}$I, $^{131}$I, $^{142}$Pr, $^{153}$Sm, $^{161}$Tb, $^{166}$Dy, $^{166}$Ho, $^{177}$Lu, $^{186}$Re, $^{188}$Re, $^{189}$Re, $^{212}$Pb, $^{212}$Bi, $^{213}$Bi, $^{211}$At, $^{223}$Ra and $^{225}$Ac. Particularly useful diagnostic/detection radionuclides include, but are not limited to, $^{18}$F, $^{52}$Fe, $^{62}$Cu, $^{64}$Cu, $^{67}$Cu, $^{67}$Ga, $^{68}$Ga, $^{86}$Y, $^{89}$Zr, $^{94m}$Tc, $^{94}$Tc, $^{99m}$Tc, $^{111}$In, $^{123}$I, $^{124}$I, $^{125}$I, $^{131}$I, $^{154-158}$Gd and $^{175}$Lu.

Chelators such as those disclosed in U.S. Pat. No. 5,753,206, especially thiosemi-carbazonylglyoxylcysteine (Tscg-Cys) and thiosemicarbazinyl-acetylcysteine (Tsca-Cys) chelators are advantageously used to bind soft acid cations of Tc, Re, Bi and other transition metals, lanthanides and actinides that are tightly bound to soft base ligands, especially sulfur- or phosphorus-containing ligands. It can be useful to link more than one type of chelator to a peptide, e.g., a DTPA or similar chelator for, say In(III) cations, and a thiol-containing chelator, e.g., Tscg-Cys, for Tc cations. Because antibodies to a di-DTPA hapten are known (Barbet '395, supra) and are readily coupled to a targeting antibody to form a bsAb, it is possible to use a peptide hapten with cold di-DTPA chelator and another chelator for binding a radioisotope, in a pretargeting protocol, for targeting the radioisotope. One example of such a peptide is Ac-Lys(DTPA)-Tyr-Lys(DTPA)-Lys(Tscg-Cys-)-$NH_2$ (SEQ ID NO: 37). This peptide can be preloaded with In(III) and then labeled with 99-m-Tc cations, the In(III) ions being preferentially chelated by the DTPA and the Tc cations binding preferentially to the thiol-containing Tscg-Cys. Other hard acid chelators such as NOTA, DOTA, TETA and the like can be substituted for the DTPA groups, and Mabs specific to them can be produced using analogous techniques to those used to generate the anti-di-DTPA Mab.

It will be appreciated that two different hard acid or soft acid chelators can be incorporated into the linker, e.g., with different chelate ring sizes, to bind preferentially to two different hard acid or soft acid cations, due to the differing sizes of the cations, the geometries of the chelate rings and the preferred complex ion structures of the cations. This will permit two different metals, one or both of which may be radioactive or useful for MRI enhancement, to be incorporated into a linker for eventual capture by a pretargeted bsAb.

Preferred chelators include NOTA, DOTA and Tscg and combinations thereof. These chelators have been incorporated into a chelator-peptide conjugate motif as exemplified as described herein, such as in the following constructs:

(a) DOTA-Phe-Lys(HSG)-D-Tyr-Lys(HSG)-$NH_2$;

(b) DOTA-Phe-Lys(HSG)-Tyr-Lys(HSG)-$NH_2$ (SEQ ID NO: 7);

(c) Ac-Lys(HSG)D-Tyr-Lys(HSG)-Lys(Tscg-Cys)-$NH_2$;

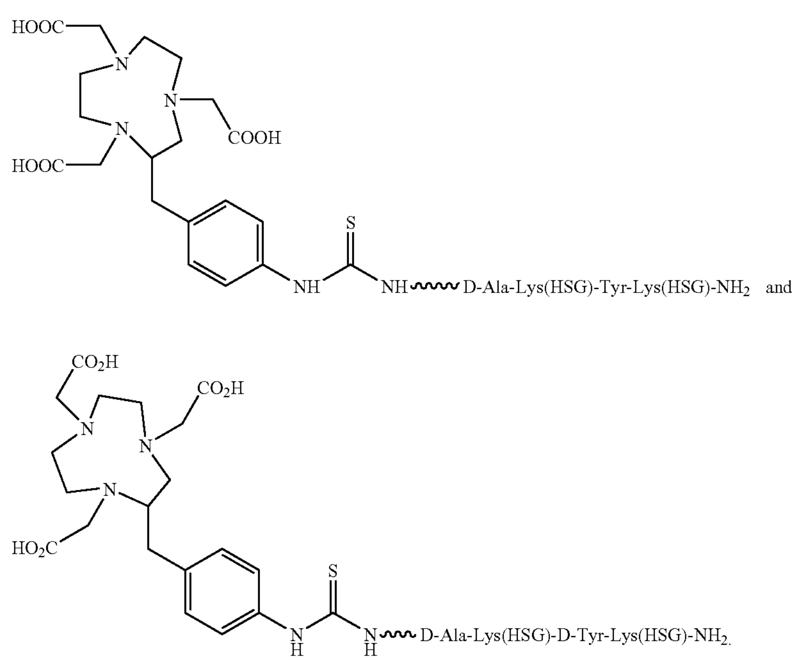

The chelator-peptide conjugates (d) and (e), above, has been shown to bind $^{68}$Ga and is thus useful in positron emission tomography (PET) applications.

Chelators are coupled to the linker moieties using standard chemistries which are discussed more fully in the working Examples below. Briefly, the synthesis of the peptide Ac-Lys(HSG)D-Tyr-Lys(HSG)-Lys(Tscg-Cys-)-$NH_2$ was accomplished by first attaching Aloc-Lys(Fmoc)-OH to a Rink amide resin on the peptide synthesizer. The protecting group abbreviations "Aloc" and "Fmoc" used herein refer to the groups allyloxycarbonyl and fluorenylmethyloxy carbonyl. The Fmoc-Cys(Trt)-OH and TscG were then added to the side chain of the lysine using standard Fmoc automated synthesis protocols to form the following peptide: Aloc-Lys(Tscg-Cys(Trt)-rink resin. The Aloc group was then removed. The peptide synthesis was then continued on the synthesizer to make the following peptide: (Lys(Aloc)-D-Tyr-Lys(Aloc)-Lys(Tscg-Cys(Trt)-)-rink resin. Following N-terminus acylation, and removal of the side chain Aloc protecting groups. The resulting peptide was then treated with activated N-trityl-HSG-OH until the resin gave a negative test for amines using the Kaiser test. See Karacay et al. *Bioconjugate Chem.* 11:842-854 (2000). The synthesis of Ac-Lys(HSG)D-Tyr-Lys(HSG)-Lys(Tscg-Cys-)-$NH_2$, as well as the syntheses of DOTA-Phe-Lys(HSG)-D-Tyr-Lys(HSG)-$NH_2$; and DOTA-Phe-Lys(HSG)-Tyr -Lys(HSG)-$NH_2$ (SEQ ID NO: 7) are described in greater detail below.

Preparation of Metal Chelates

Chelator-peptide conjugates may be stored for long periods as solids. They may be metered into unit doses for metal-binding reactions, and stored as unit doses either as solids, aqueous or semi-aqueous solutions, frozen solutions or lyophilized preparations. They may be labeled by well-known procedures. Typically, a hard acid cation is introduced as a solution of a convenient salt, and is taken up by the hard acid chelator and possibly by the soft acid chelator. However, later addition of soft acid cations leads to binding thereof by the soft acid chelator, displacing any hard acid cations which may be chelated therein. For example, even in the presence of an excess of cold $^{111}InCl_3$, labeling with 99m-Tc(V) glucoheptonate or with Tc cations generated in situ with stannous chloride and Na99m-$TcO_4$ proceeds quantitatively on the soft acid chelator. Other soft acid cations such as $^{186}$Re, $^{188}$Re, $^{213}$Bi and divalent or trivalent cations of Mn, Co, Ni, Pb, Cu, Cd, Au, Fe, Ag (monovalent), Zn and Hg, especially $^{64}$Cu and $^{67}$Cu, and the like, some of which are useful for radioimmunodiagnosis or radioimmunotherapy, can be loaded onto the linker peptide by analogous methods. Re cations also can be generated in situ from perrhenate and stannous ions or a prereduced rhenium glucoheptonate or other transchelator can be used. Because reduction of perrhenate requires more stannous ion (typically above 200 μg/mL final concentration) than is needed for the reduction of Tc, extra care needs to be taken to ensure that the higher levels of stannous ion do not reduce sensitive disulfide bonds such as those present in disulfide-cyclized peptides. During radiolabeling with rhenium, similar procedures are used as are used with the Tc-99m. A preferred method for the preparation of ReO metal complexes of the Tscg-Cys-ligands is by reacting the peptide with $ReOCl_3(P(Ph_3)_2$ but it is also possible to use other reduced species such as $ReO(ethylenediamine)_2$.

8. Humanized, Chimeric and Human Antibodies Use for Treatment and Diagnosis

Contemplated in the present invention is the use of murine, humanized, chimeric and human MN3 antibodies and fragments thereof in delivery methods of therapeutic and diagnostic/detection agents, and therapeutic and diagnostic/detection methods. Preferably, the MN3 antibodies and fragments thereof are chimeric, humanized or human MN3 antibodies.

For example, a method of delivering a diagnostic/detection agent, a therapeutic agent, or a combination thereof to a target comprising (i) administering to a subject the antibody or fragment thereof an antibody, fusion protein, or fragment thereof; (ii) waiting a sufficient amount of time for an amount of the non-binding protein to clear the subject's blood stream; and (iii) administering to said subject a carrier molecule comprising a diagnostic/detection agent, a therapeutic agent, or a combination thereof, that binds to a binding site of said antibody. Preferably, the carrier molecule binds to more than one binding site of the antibody.

The present invention also contemplates methods of diagnosing or detecting a malignancy in a subject. Diagnosis/detection may be accomplished by administering a diagnostically effective amount of a diagnostic/detection immunoconjugate, comprising an MN3 monoclonal antibody or fragment thereof or a fusion protein or fragment thereof, wherein said MN3 MAb or fragment thereof or fusion protein or fragment thereof is bound to at least one diagnostic/detection agent, formulated in a pharmaceutically acceptable excipient, and detecting said label. Preferably, the MN3 antibody, fusion protein, or fragment thereof is an MN3 antibody.

In a related vein, a method of diagnosing or detecting a malignancy in a subject comprising (i) performing an in vitro diagnosis assay on a specimen from said subject with a composition comprising a MN3 MAb or fragment thereof or a antibody fusion protein or fragment thereof of any one of the antibodies, fusion proteins, or fragments thereof of the present invention, is also considered. Preferably, the in vitro diagnosis assay is selected from the group consisting of immunoassays, RT-PCR and immunohistochemistry.

In the methods described herein, radioactive and non-radioactive agents can be used as diagnostic agents. A suitable non-radioactive diagnostic agent is a contrast agent suitable for magnetic resonance imaging, a radiopaque compound for X-rays or computed tomography, or a contrast agent suitable for ultrasound. Magnetic imaging agents include, for example, non-radioactive metals, such as manganese, iron and gadolinium, complexed with metal-chelate combinations that include 2-benzyl-DTPA and its monomethyl and cyclohexyl analogs, when used along with the antibodies of the invention. See U.S. Ser. No. 09/921,290 filed on Oct. 10, 2001, which is incorporated in its entirety by reference. In a preferred embodiment, the contrast agent is an ultrasound-enhancing agent. Still preferred, the ultrasound-enhancing agent is a liposome. Radiopaque and contrast materials are used for enhancing X-rays and computed tomography, and include iodine compounds, barium compounds, gallium compounds, thallium compounds, etc. Specific compounds include barium, diatrizoate, ethiodized oil, gallium citrate, iocarmic acid, iocetamic acid, iodamide, iodipamide, iodoxamic acid, iogulamide, iohexol, iopamidol, iopanoic acid, ioprocemic acid, iosefamic acid, ioseric acid, iosulamide meglumine, iosemetic acid, iotasul, iotetric acid, iothalamic acid, iotroxic acid, ioxaglic acid, ioxotrizoic acid, ipodate, meglumine, metrizamide, metrizoate, propyliodone, and thallous chloride.

Also described in the present invention is the use of murine, chimeric, humanized and human MN3 antibodies and fragments thereof in methods for treating malignancies. For example, a malignancy of particular interest in this patent is a myeloid leukemia. The method comprises administering to a subject a therapeutically effective amount of an antibody or fragment thereof or an antibody fusion protein or fragment thereof comprising at least two MAbs or fragments thereof, wherein at least one MN3 MAb or fragment thereof or fusion proteins or fragments thereof are any one of the antibodies of the present invention, formulated in a pharmaceutically suitable excipient. In another embodiment, a second MAb, fusion protein or fragment thereof is not an MN3 antibody, fusion protein or fragment thereof.

In a related vein, a method of treating a cancer cell in a subject comprising (i) administering to said subject a therapeutically effective amount of a composition comprising a naked or conjugated MN3 MAb or fragment thereof or antibody fusion protein or fragment thereof, of any one of the antibodies, fusion proteins, or fragments thereof of the present invention, (ii) formulating said MN3 MAb or fragment thereof or antibody fusion protein or fragment thereof in a pharmaceutically suitable excipient, is contemplated. Preferably, such a composition further comprises a second antibody, fusion protein, or fragment thereof. The second antibody, fusion protein, or fragment thereof can, but need not be an MN3 antibody, fusion protein or fragment thereof. The preferred mode of administration is parenterally. Examples of parental administration include through intravenous, subcutaneous, intramuscular, intradermal, intrathecal/intraspinal routes or the like. Administration can also occur through an inhalant, such as by nasal route or aerosol, which can be important when a subject is suffering from cystic fibrosis. Also preferred, the dosage is repeatedly administered. Still preferred, the MN3 antibody is administered in a dosage of 20 to 2000 milligrams protein per dose. Even more preferred, the MN3 antibody is administered in a dosage of 50 to 500 mg protein dose per injection.

The compositions for treatment contain at least one naked murine, humanized, chimeric or human MN3 antibody described herein or fragment thereof alone or in combination with other MN3 antibodies or antibody fragments thereof, such as other MN3 humanized, chimeric or human antibodies. Preferably, the MN3 antibody, fusion protein, or fragment thereof in the composition for treatment is administered in a dosage of 20-2000 milligrams per dose. Also preferred, the MN3 antibody or fragment thereof in the composition for treatment is an MN3 antibody or fragment thereof. The present invention also contemplates treatment with at least one naked humanized, chimeric or human MN3 antibody or fragment thereof in combination with other antibodies or antibody fragments thereof that are not MN3 antibodies, whereby these other antibodies can be administered unconjugated (naked) or conjugated with at least one diagnostic/detection or therapeutic agent. For example, other antibodies suitable for combination therapy include, but are not limited to, granulocyte associated antibodies and fragments thereof such as antibodies reactive with MAbs reactive with NCA-90, NCA-95, CD15, CD33, and from the MAbs MN2, MN3, MN-15, NP-1, NP-2, BW 250/183, and MAb 47, or a combination thereof. Suitable antibodies could also include those targeted against myeloid leukemias. Additionally, treatment can be effected with at least one humanized, chimeric or human MN3 immunoconjugate or fragment thereof alone or in combination with anti-granulocyte antibodies or antibody fragments thereof. Still preferred, compositions for treatment can contain at least one humanized, chimeric or human MN3 immunoconjugate or fragment thereof in combination with other antibodies or antibody fragments thereof that are not anti-granulocyte antibodies, these being either naked or conjugated to a therapeutic agent.

Similarly, conjugated and naked MN3 humanized, chimeric or human antibodies or fragments thereof may be used alone or may be administered with, but unconjugated to, the various diagnostic/detection or therapeutic agents described herein. Also, naked or conjugated MN3 antibodies to the same or different epitope or antigen may be also combined with one or more of the antibodies of the present invention.

Accordingly, the present invention contemplates the administration of murine, humanized, chimeric and human MN3 antibodies and fragments thereof alone, as a naked antibody, or administered as a multimodal therapy. Multimodal therapies of the present invention further include immunotherapy with naked or conjugated MN3 antibodies supplemented with administration of other conjugated or unconjugated antibody, fusion protein, or fragment thereof. For example, a humanized, chimeric or human MN3 antibody may be combined with another naked humanized, naked chimeric or naked human MN3 antibody, or a humanized, chimeric or human MN3 antibody immunoconjugate, such as a humanized, chimeric or human MN3 antibody conjugated to an isotope, one or more chemotherapeutic agents, cytokines, enzymes, enzyme-inhibitors, hormones or hormone antagonists, metals, toxins, or a combination thereof. For example, the present invention contemplates treatment of a naked or conjugated MN3 antibody or fragment thereof before, in combination with, or after other anti-granulocyte associated antibodies. A fusion protein of a murine, humanized, chimeric or human MN3 antibody and a toxin or may also be used in this invention. Many different antibody combinations may be constructed, either as naked antibodies or as partly naked and partly conjugated with a therapeutic agent or immunomodulator, or merely in combination with another therapeutic agents, such as a cytotoxic drug or with radiation.

The compositions for treatment contain at least one humanized, chimeric or human monoclonal MN3 antibody or fragment thereof alone or in combination with other antibodies and fragments thereof, such as other naked or conjugated, murine, humanized, chimeric, or human antibodies, or fragments thereof, or fusion proteins or fragments thereof, or therapeutic agents. In particular, combination therapy with a fully human antibody is also contemplated and is produced by the methods as set forth above.

Naked or conjugated antibodies, fusion proteins, or fragments thereof may be also combined with one or more of the antibodies, fusion proteins, or fragments thereof to the same or different epitope or antigen. For example, a naked, murine, humanized, chimeric or human MN3 antibody may be combined with a naked murine, humanized, naked chimeric or naked human MN3 antibody; a murine, humanized, chimeric or human naked MN3 antibody may be combined with a MN3 immunoconjugate; a naked murine, humanized, chimeric, human MN3 antibody may be combined with a different antibody radioconjugate or a different naked antibody; a murine, humanized, chimeric or fully human MN3 antibody may be combined with a murine, humanized, chimeric or human MN3 antibody conjugated to an isotope, or to one or more chemotherapeutic agents, cytokines or other immunomodulator, toxins, enzymes, enzyme inhibitors, hormones, hormone antagonists, or a combination thereof. A fusion protein of a murine, humanized, chimeric or human MN3 antibody and a toxin or immunomodulator may also be used in this invention. Many different antibody combinations, targeting at least two different antigens may be constructed, either as naked antibodies or as partly naked and partly conjugated with a therapeutic agent or immunomodulator, or merely in combination with another therapeutic agents, such as a cytotoxic drug or with radiation.

Multimodal therapies of the present invention further include immunotherapy with naked MN3 antibodies or fragments thereof supplemented with administration of granulocyte associated antibodies in the form of a conjugated or unconjugated antibody, fusion proteins, or fragment thereof. In a preferred embodiment, antibodies or fragments thereof for multimodal therapy include, but are not limited to, antibodies reactive with NCA-90, NCA-95, CD15, CD33, and from the MAbs MN2, MN3, MN-15, NP-1, NP-2, BW 250/183, and MAb 47, or a combination thereof. These antibodies include polyclonal, monoclonal, chimeric, human or humanized antibodies and fragments thereof that recognize at least one epitope on these antigenic determinants.

In another form of multimodal therapy, subjects receive naked MN3 antibodies or fragments thereof, and/or MN3 immunoconjugates or fragments thereof, in conjunction with standard cancer chemotherapy. Fludarabine, alone or in combination with cytosine arabinoside, is a regimen used to treat myeloid leukemia. Other suitable combination chemotherapeutic regimens are well known, such as with chlorambucil alone, or in combination with these other drugs, to those of skill in the art. In a preferred multimodal therapy, both chemotherapeutic drugs and cytokines are co-administered with a conjugated or unconjugated MN3 antibody, fusion protein, or fragment thereof, according to the present invention. Preferably, the MN3 antibody or fragment thereof is an MN3 antibody or fragment thereof. The cytokines, chemotherapeutic drugs and antibody, fusion protein, or fragment thereof, can be administered in any order, or together.

The present invention also encompasses the use of the bsAb and at least one therapeutic or diagnostic/detection agent associated with the linker moieties discussed above in intraoperative, intravascular, and endoscopic tumor and lesion detection, biopsy and therapy as described in U.S. Pat. No. 6,096,289, and incorporated herein by reference. Preferably, the bispecific antibody has at least one arm that binds the epitope recognized by MN3.

The MN3 antibodies, fusion proteins, and fragments thereof of the present invention can be employed not only for therapeutic or imaging purposes, but also as aids in performing research in vitro. For example, the bsAbs of the present invention can be used in vitro to ascertain if a targetable construct can form a stable complex with one or more bsAbs. Such an assay would aid the skilled artisan in identifying targetable constructs which form stable complexes with bsAbs. This would, in turn, allow the skilled artisan to identify targetable constructs which are likely to be superior as therapeutic and/or imaging agents.

The assay is advantageously performed by combining the targetable construct in question with at least two molar equivalents of a bsAb. Following incubation, the mixture is analyzed by size-exclusion HPLC to determine whether or not the construct has bound to the bsAb. Alternatively, the assay is performed using standard combinatorial methods wherein solutions of various bsAbs are deposited in a standard 96-well plate. To each well, is added solutions of targetable construct(s). Following incubation and analysis, one can readily determine which construct(s) bind(s) best to which bsAb(s).

It should be understood that the order of addition of the bsAb to the targetable construct is not crucial; that is, the bsAb may be added to the construct and vice versa. Likewise, neither the bsAb nor the construct needs to be in solution; that is, they may be added either in solution or neat, whichever is most convenient. Lastly, the method of analysis for binding is not crucial as long as binding is established. Thus, one may analyze for binding using standard analytical methods including, but not limited to, FABMS, high-field NMR or other appropriate method in conjunction with, or in place of, size-exclusion HPLC.

Bispecific Antibody Therapy and Diagnosis

The present invention provides a bispecific antibody or antibody fragment having at least one binding region that specifically binds a targeted cell marker and at least one other binding region that specifically binds a targetable conjugate. The targetable conjugate comprises a carrier portion which comprises or bears at least one epitope recognized by at least one binding region of the bispecific antibody or antibody fragment.

For example, a method of treating or identifying diseased tissues in a subject, comprising: (A) administering to said subject a bi-specific antibody or antibody fragment having at least one arm that specifically binds a targeted tissue and at least one other arm that specifically binds a targetable conjugate, wherein said one arm that specifically binds a targeted tissue is an MN3 antibody; (B) optionally, administering to said subject a clearing composition, and allowing said composition to clear non-localized antibodies or antibody fragments from circulation; (C) administering to said subject a first targetable conjugate which comprises a carrier portion which comprises or bears at least one epitope recognizable by said at least one other arm of said bi-specific antibody or antibody fragment, and one or more conjugated therapeutic or diagnostic agents; and (D) when said therapeutic agent is an enzyme, further administering to said subject 1) a prodrug, when said enzyme is capable of converting said prodrug to a drug at the target site; or 2) a drug which is capable of being detoxified in said subject to form an intermediate of lower toxicity, when said enzyme is capable of reconverting said detoxified intermediate to a toxic form, and, therefore, of increasing the toxicity of said drug at the target site, or 3) a prodrug which is activated in said subject through natural processes and is subject to detoxification by conversion to an intermediate of lower toxicity, when said enzyme is capable of reconverting said detoxified intermediate to a toxic form, and, therefore, of increasing the toxicity of said drug at the target site, or 4) a second targetable conjugate which comprises a carrier portion which comprises or bears at least one epitope recognizable by said at least one other arm of said bi-specific antibody or antibody fragment, and a prodrug, when said enzyme is capable of converting said prodrug to a drug at the target site, is described. Optionally, when said first targetable conjugate comprises a prodrug, administering a second targetable conjugate which comprises a carrier portion which comprises or bears at least one epitope recognizable by said at least one other arm of said bi-specific antibody or antibody or antibody fragment, and an enzyme capable of converting said prodrug to a drug or of reconverting a detoxified intermediate of said drug to a toxic form. Preferably, the targetable conjugate comprises at least two HSG haptens.

In a related vein, a method for detecting or treating neoplasms expressing an antigen recognized by MN3 in a mammal is described. This method comprises (A) administering an effective amount of a bispecific antibody or antibody fragment comprising at least one arm that specifically binds a targeted tissue and at least one other arm that specifically binds a targetable conjugate, wherein said one arm that specifically binds a targeted tissue is an MN3 antibody or fragment thereof; and (B) administering a targetable conjugate selected from the group consisting of (i) DOTA-Phe-Lys(HSG)-D-Tyr-Lys(HSG) -$NH_2$; (ii) DOTA-Phe-Lys(HSG)-Tyr-Lys(HSG)-$NH_2$ (SEQ ID NO: 7); (iii) Ac-Lys(HSG)D-Tyr -Lys(HSG)-Lys(Tscg-Cys)-$NH_2$;

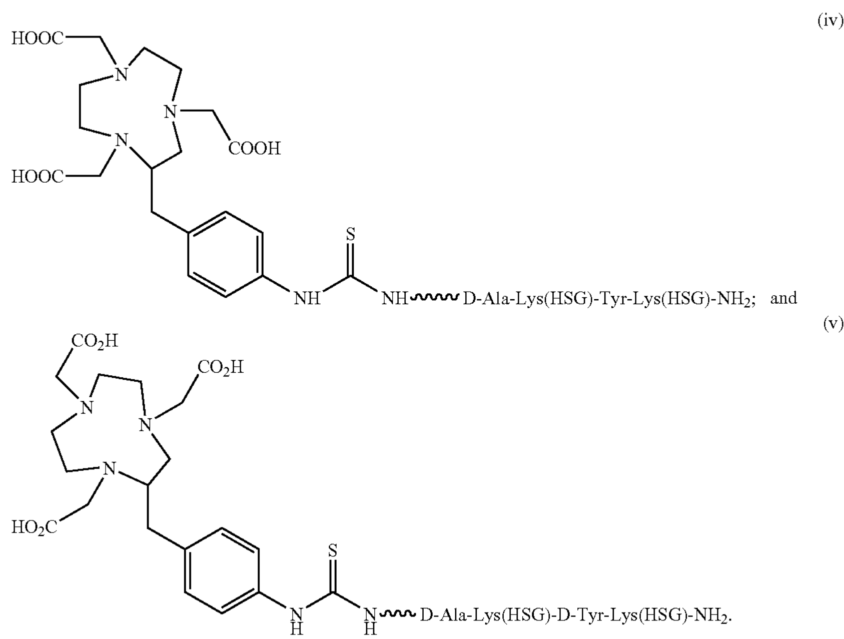

Optionally, the method further comprises administering to a subject a clearing composition, and allowing the composition to clear non-localized antibodies or antibody fragments from the circulation.

Bispecific antibodies and fragments thereof of the present invention are useful in pretargeting methods and provide a preferred way to deliver two therapeutic agents or two diagnostic/detection agents to a subject. U.S. Ser. No. 09/382,186 discloses a method of pretargeting using a bispecific antibody, in which the bispecific antibody is labeled with $^{125}$I and delivered to a subject, followed by a divalent peptide labeled with $^{99m}$Tc. The delivery results in excellent tumor/normal tissue ratios for $^{131}$I and $^{99m}$Tc, thus showing the utility of two diagnostic radioisotopes. Any combination of known therapeutic agents or diagnostic agents can be used to label the MN3 antibodies, MN3 fusion proteins, and fragments thereof of the present invention. The binding specificity of the MN3 immunoconjugate, the efficacy of the therapeutic agent or diagnostic agent and the effector activity of the Fc portion of the antibody can be determined by standard testing of the conjugates.

The administration of a bsAb and a therapeutic agent associated with the linker moieties discussed above may be conducted by administering the bsAb at some time prior to administration of the therapeutic agent which is associated with the linker moiety. The doses and timing of the reagents can be readily devised by a skilled artisan, and are dependent on the specific nature of the reagents employed. If a bsAb-F(ab')$_2$ derivative is given first, then a waiting time of 24-72 hr before administration of the linker moiety would be appropriate. If an IgG-Fab' bsAb conjugate is the primary targeting vector, then a longer waiting period before administration of the linker moiety would be indicated, in the range of 3-10 days.

After sufficient time has passed for the bsAb to target to the diseased tissue, the diagnostic/detection agent is administered. Subsequent to administration of the diagnostic/detection agent, imaging can be performed. Tumors can be detected in body cavities by means of directly or indirectly viewing various structures to which energy of the appropriate wavelength is delivered and then collected. Lesions at any body site can be viewed so long as nonionizing radiation or energy can be delivered and recaptured from these structures. For example, PET, which is a high resolution, non-invasive, imaging technique, can be used with the inventive antibodies for the visualization of human disease. In PET, 511 keV gamma photons produced during positron annihilation decay are detected.

The linker moiety may also be conjugated to an enzyme capable of activating a prodrug at the target site or improving the efficacy of a normal therapeutic by controlling the body's detoxification pathways. Following administration of the bsAb, an enzyme conjugated to the linker moiety, a low MW hapten recognized by the second arm of the bsAb, is administered. After the enzyme is pretargeted to the target site, a cytotoxic drug is injected, which is known to act at the target site. The drug may be one which is detoxified by the mammal's ordinary detoxification processes. For example, the drug may be converted into the potentially less toxic glucuronide in the liver. The detoxified intermediate can then be reconverted to its more toxic form by the pretargeted enzyme at the target site. Alternatively, an administered prodrug can be converted to an active drug by the pretargeted enzyme. The pretargeted enzyme improves the efficacy of the treatment by recycling the detoxified drug. This approach can be adopted for use with any enzyme-drug pair.

The enzyme capable of activating a prodrug at the target site or improving the efficacy of a normal therapeutic by controlling the body's detoxification pathways may alternatively be conjugated to the hapten. The enzyme-hapten conjugate is administered to the subject following administration of the pre-targeting bsAb and is directed to the target site. After the enzyme is localized at the target site, a cytotoxic drug is injected, which is known to act at the target site, or a prodrug form thereof which is converted to the drug in situ by the pretargeted enzyme. As discussed above, the drug is one which is detoxified to form an intermediate of lower toxicity, most commonly a glucuronide, using the mammal's ordinary detoxification processes. The detoxified intermediate, e.g., the glucuronide, is reconverted to its more toxic form by the pretargeted enzyme and thus has enhanced cytotoxicity at the target site. This results in a recycling of the drug. Similarly, an administered prodrug can be converted to an active drug through normal biological processes. The pretargeted enzyme improves the efficacy of the treatment by recycling the detoxified drug. This approach can be adopted for use with any enzyme-drug pair.

The invention further contemplates the use of the inventive bsAb and the diagnostic agent(s) in the context of Boron Neutron Capture Therapy (BNCT) protocols. BNCT is a binary system designed to deliver ionizing radiation to tumor cells by neutron irradiation of tumor-localized $^{10}$B atoms. BNCT is based on the nuclear reaction which occurs when a stable isotope, isotopically enriched $^{10}$B (present in 19.8% natural abundance), is irradiated with thermal neutrons to produce an alpha particle and a $^{7}$Li nucleus. These particles have a path length of about one cell diameter, resulting in high linear energy transfer. Just a few of the short-range 1.7 MeV alpha particles produced in this nuclear reaction are sufficient to target the cell nucleus and destroy it. Success with BNCT of cancer requires methods for localizing a high concentration of $^{10}$B at tumor sites, while leaving non-target organs essentially boron-free. Compositions and methods for treating tumors in subjects using pre-targeting bsAb for BNCT are described in co-pending patent application Ser. No. 09/205,243, incorporated herein in its entirety and can easily be modified for the purposes of the present invention.

A clearing agent may be used which is given between doses of the bsAb and the linker moiety. The present inventors have discovered that a clearing agent of novel mechanistic action may be used with the invention, namely a glycosylated anti-idiotypic (anti-Id) Fab' fragment targeted against the disease targeting amm(s) of the bsAb. For example, anti-CSAp (Mu-9 Ab)×anti-peptide bsAb is given and allowed to accrete in disease targets to its maximum extent. To clear residual bsAb, an anti-idiotypic (anti-Id) Ab to Mu-9 is given, preferably as a glycosylated Fab' fragment. The clearing agent binds to the bsAb in a monovalent manner, while its appended glycosyl residues direct the entire complex to the liver, where rapid metabolism takes place. Then the therapeutic which is associated with the linker moiety is given to the subject. The anti-Id Ab to the Mu-9 arm of the bsAb has a high affinity and the clearance mechanism differs from other disclosed mechanisms (see Goodwin et al., ibid), as it does not involve cross-linking, because the anti-Id-Fab' is a monovalent moiety. The same is accomplished with MN3 Mabs and corresponding anti-MN3 anti-Id antibodies.

Also contemplated herein is a kit useful for treating or identifying diseased tissues in a subject comprising: (A) a bi-specific antibody or antibody fragment having at least one arm that specifically binds a targeted tissue and at least one other arm that specifically binds a targetable conjugate, wherein said one arm that specifically binds a targeted tissue is an MN3 antibody or fragment thereof; (B) a first targetable conjugate which comprises a carrier portion which comprises or bears at least one epitope recognizable by said at least one other arm of said bi-specific antibody or antibody fragment, and one or more conjugated therapeutic or diagnostic agents; and (C) optionally, a clearing composition useful for clearing non-localized antibodies and antibody fragments; and (D) optionally, when said therapeutic agent conjugated to said first targetable conjugate is an enzyme, 1) a prodrug, when said enzyme is capable of converting said prodrug to a drug at the target site; or 2) a drug which is capable of being detoxified in said subject to form an intermediate of lower toxicity, when said enzyme is capable of reconverting said detoxified intermediate to a toxic form, and, therefore, of increasing the toxicity of said drug at the target site, or 3) a prodrug which is activated in said subject through natural processes and is subject to detoxification by conversion to an intermediate of lower toxicity, when said enzyme is capable of reconverting said detoxified intermediate to a toxic form, and, therefore, of increasing the toxicity of said drug at the target site, or 4) a second targetable conjugate which comprises a carrier portion which comprises or bears at least one epitope recognizable by said at least one other arm of said bi-specific antibody or antibody fragment, and a prodrug, when said enzyme is capable of converting said prodrug to a drug at the target site. Preferably, the targetable conjugate is selected from the group consisting of (i) DOTA-Phe-Lys(HSG)-D-Tyr-Lys(HSG)-$NH_2$; (ii) DOTA-Phe-Lys(HSG)-Tyr-Lys(HSG)-$NH_2$ (SEQ ID NO: 7); (iii) Ac-Lys(HSG)D-Tyr-Lys(HSG)-Lys(Tscg-Cys)-$NH_2$;

(iv)

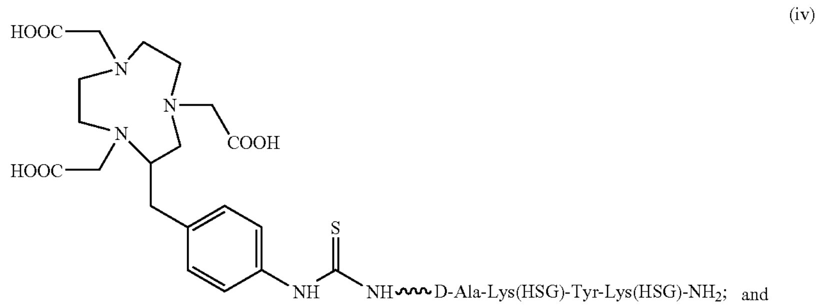

and (v)

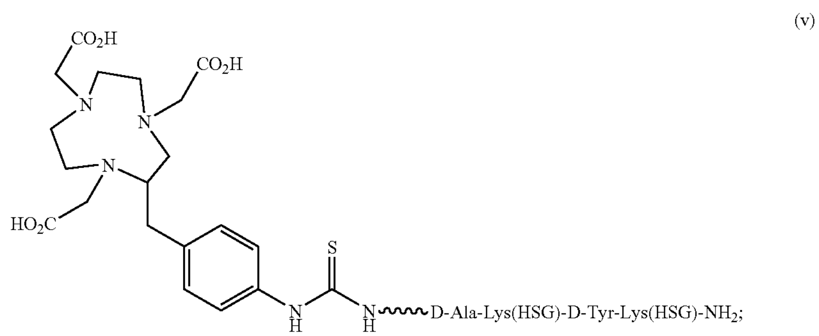

A method of screening for a targetable conjugate is also described, comprising (A) contacting said targetable construct with a bi-specific antibody or antibody fragment having at least one arm that specifically binds a targeted tissue and at least one other arm that specifically binds said targetable conjugate to give a mixture, wherein said one arm that specifically binds a targeted tissue is a MN3 antibody or fragment thereof; and (B) optionally incubating said mixture; and (C) analyzing said mixture.

The present invention further provides a method for imaging malignant tissue or cells in a mammal expressing an antigen recognized by MN3; a method of intraoperatively identifying/disclosing diseased tissues expressing an antigen recognized by MN3, in a subject; a method for endoscopic identification of diseased tissues expressing an antigen recognized by MN3, in a subject and a method for the intravascular identification of diseased tissues expressing an antigen recognized by MN3, in a subject. Such methods comprise (A) administering an effective amount of a bispecific antibody or antibody fragment comprising at least one arm that specifically binds a targeted tissue expressing an antigen recognized by MN3 and at least one other arm that specifically binds a targetable conjugate, wherein said one arm that specifically binds a targeted tissue is an MN3 antibody or fragment thereof; and (B) administering a targetable conjugate selected from the group consisting of (i) DOTA-Phe-Lys(HSG)-D-Tyr-Lys(HSG)-$NH_2$; (ii) DOTA-Phe-Lys(HSG)-Tyr -Lys (HSG)-$NH_2$ (SEQ ID NO: 7); (iii) Ac-Lys(HSG)D-Tyr-Lys (HSG)-Lys(Tscg-Cys)-$NH_2$;

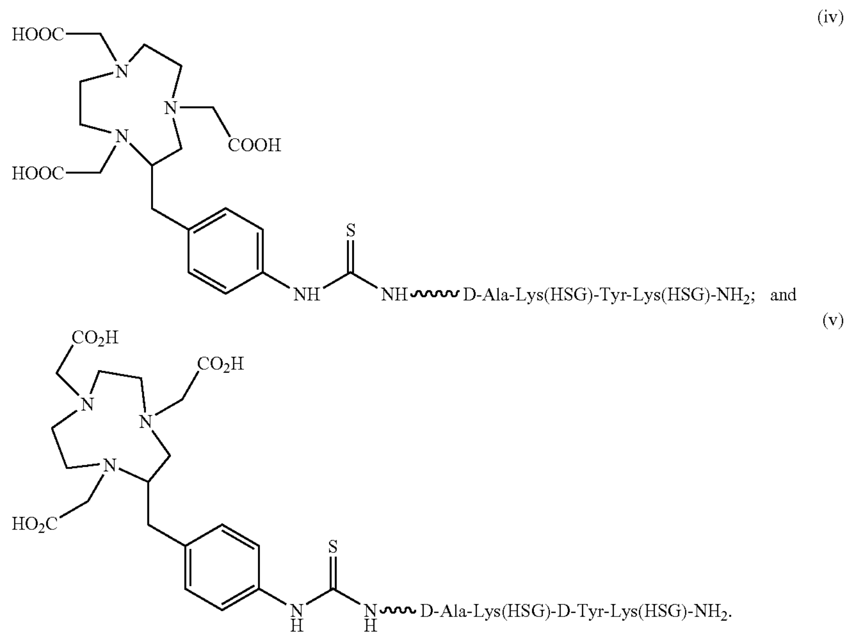

Also considered herein is a method of detection of lesions during an endoscopic, laparoscopic, intravascular catheter, or surgical procedure, wherein the method comprises: (A) injecting a subject who is to undergo such a procedure with a bispecific antibody $F(ab)_2$ or $F(ab')_2$ fragment, wherein the bispecific antibody or fragment has a first antibody binding site which specifically binds to an antigen recognized by MN3, and has a second antibody binding site which specifically binds to a hapten, and permitting the antibody fragment to accrete at target sites; (B) optionally clearing non-targeted antibody fragments using a galactosylated anti-idiotype clearing agent if the bispecific fragment is not largely cleared from circulation within about 24 hours of injection, and injecting a bivalent labeled hapten, which quickly localizes at the target site and clears through the kidneys; (C) detecting the presence of the hapten by close-range detection of elevated levels of accreted label at the target sites with detection means, within 48 hours of the first injection, and conducting said procedure, wherein said detection is performed without the use of a contrast agent or subtraction agent. Preferably, the hapten is labeled with a diagnostic/detection radioisotope, a MRI image-enhancing agent or a fluorescent label.

In a related vein, a method for close-range lesion detection, during an operative, intravascular, laparoscopic, or endoscopic procedure, wherein the method comprises: (A) injecting a subject to such a procedure parenterally with an effective amount of an MN3 immunoconjugate or fragment thereof, (B) conducting the procedure within 48 hours of the injection; (C) scanning the accessed interior of the subject at close range with a detection means for detecting the presence of said labeled antibody or fragment thereof; and (D) locating the sites of accretion of said labeled antibody or fragment thereof by detecting elevated levels of said labeled antibody or fragment thereof at such sites with the detection means, is also described.

9. Pharmaceutically Suitable Excipients

The murine, humanized, chimeric and human MN3 MAbs to be delivered to a subject can consist of the MAb alone, immunoconjugate, fusion protein, or can comprise one or more pharmaceutically suitable excipients, one or more additional ingredients, or some combination of these.

The conjugated or unconjugated MN3 antibodies and fragments thereof, or fusion proteins and fragments thereof, of the present invention can be formulated according to known methods to prepare pharmaceutically useful compositions. Preferably, the MN3 antibody or fragment thereof is an MN3 antibody or fragment thereof. Sterile phosphate-buffered saline is one example of a pharmaceutically suitable excipient. Other suitable excipients are well-known to those in the art. See, for example, Ansel et al., PHARMACEUTICAL DOSAGE FORMS AND DRUG DELIVERY SYSTEMS, 5th Edition (Lea & Febiger 1990), and Gennaro (ed.), REMINGTON'S PHARMACEUTICAL SCIENCES, 18th Edition (Mack Publishing Company 1990), and revised editions thereof.

The conjugated or unconjugated MN3 antibody, fusion protein, or fragments thereof of the present invention can be formulated for intravenous administration via, for example, bolus injection or continuous infusion. Preferably, the MN3 antibody or fragments is an MN3 antibody or fragment thereof. Formulations for injection can be presented in unit dosage form, e.g., in ampules or in multi-dose containers, with an added preservative. The compositions can take such forms as suspensions, solutions or emulsions in oily or aqueous vehicles, and can contain formulatory agents such as suspending, stabilizing and/or dispersing agents. Alternatively, the active ingredient can be in powder form for constitution with a suitable vehicle, e.g., sterile pyrogen-free water, before use.

Additional pharmaceutical methods may be employed to control the duration of action of the therapeutic or diagnostic/detection immunoconjugate or naked antibody, fusion protein, or fragments thereof. Control release preparations can be prepared through the use of polymers to complex or adsorb the immunoconjugate or naked antibody. For example, biocompatible polymers include matrices of poly(ethylene-co-vinyl acetate) and matrices of a polyanhydride copolymer of a stearic acid dimer and sebacic acid. Sherwood et al., *Bio/Technology* 10: 1446 (1992). The rate of release of an immunoconjugate or antibody from such a matrix depends upon the molecular weight of the immunoconjugate or antibody, the amount of immunoconjugate, antibody within the matrix, and the size of dispersed particles. Saltzman et al., *Biophys. J* 55: 163 (1989); Sherwood et al., supra. Other solid dosage forms are described in Ansel et al., PHARMACEUTICAL DOSAGE FORMS AND DRUG DELIVERY SYSTEMS, 5th Edition (Lea & Febiger 1990), and Gennaro (ed.), REMINGTON'S PHARMACEUTICAL SCIENCES, 18th Edition (Mack Publishing Company 1990), and revised editions thereof.

The conjugated or unconjugated MN3 antibody, fusion protein, or fragments thereof may also be administered to a mammal subcutaneously or even by other parenteral routes. Moreover, the administration may be by continuous infusion or by single or multiple boluses. In general, the dosage of an administered immunoconjugate, or naked antibody, fusion protein or fragments thereof for humans will vary depending upon such factors as the patient's age, weight, height, sex, general medical condition and previous medical history. Typically, it is desirable to provide the recipient with a dosage of immunoconjugate, naked antibody fusion protein, naked antibody, or fragments thereof that is in the range of from about 0.3 mg/kg to 30 mg/kg as a single intravenous infusion, although a lower or higher dosage also may be administered as circumstances dictate. This dosage may be repeated as needed, for example, once per week for 4-10 weeks, preferably once per week for 8 weeks, and more preferably, once per week for 4 weeks. It may also be given less frequently, such as every other week for several months. The dosage may be given through various parenteral routes, with appropriate adjustment of the dose and schedule.

For purposes of therapy, the conjugated or unconjugated antibody, fusion protein, or fragment thereof is administered to a mammal in a therapeutically effective amount. Preferably, the MN3 antibody or fragment thereof is an MN3 antibody or fragment thereof. A suitable subject for the present invention is usually a human, although a non-human animal subject is also contemplated. An antibody preparation is said to be administered in a "therapeutically effective amount" if the amount administered is physiologically significant. An agent is physiologically significant if its presence results in a detectable change in the physiology of a recipient mammal. In particular, an antibody preparation of the present invention is physiologically significant if its presence invokes an antitumor response or mitigates the signs and symptoms of an autoimmune disease state. A physiologically significant effect could also be the evocation of a humoral and/or cellular immune response in the recipient mammal.

10. Expression Vectors

The DNA sequence encoding a murine, humanized, chimeric or human MN3 MAb can be recombinantly engineered into a variety of known host vectors that provide for replication of the nucleic acid. These vectors can be designed, using known methods, to contain the elements necessary for directing transcription, translation, or both, of the nucleic acid in a cell to which it is delivered. Known methodology can be used to generate expression constructs the have a protein-coding sequence operably linked with appropriate transcriptional/translational control signals. These methods include in vitro recombinant DNA techniques and synthetic techniques. For example, see Sambrook et al., 1989, MOLECULAR CLONING: A LABORATORY MANUAL, Cold Spring Harbor Laboratory (New York); Ausubel et al., 1997, CURRENT PROTOCOLS IN MOLECULAR BIOLOGY, John Wiley & Sons (New York). Also provided for in this invention is the delivery of a polynucleotide not associated with a vector.

Vectors suitable for use in the instant invention can be viral or non-viral. Particular examples of viral vectors include adenovirus, AAV, herpes simplex virus, lentivirus, and retrovirus vectors. An example of a non-viral vector is a plasmid. In a preferred embodiment, the vector is a plasmid.

An expression vector, as described herein, is a polynucleotide comprising a gene that is expressed in a host cell. Typically, gene expression is placed under the control of certain regulatory elements, including constitutive or inducible promoters, tissue-specific regulatory elements, and enhancers. Such a gene is said to be "operably linked to" the regulatory elements.

Preferably, the expression vector of the instant invention comprises the DNA sequence encoding a humanized, chimeric or human MN3 MAb, which includes both the heavy and the light chain variable and constant regions. However, two expression vectors may be used, with one comprising the heavy chain variable and constant regions and the other comprising the light chain variable and constant regions. Still preferred, the expression vector further comprises a promoter, a DNA sequence encoding a secretion signal peptide, a genomic sequence encoding a human Ig light or heavy chain constant region, an Ig enhancer element and at least one DNA sequence encoding a selection marker.

The following applications, which describe methods in which the present antibodies and fragments can be used and alternative embodiments for the present antibodies and fragments, are also incorporated herein by reference: 60/328,835; 60/341,881; 60/342,103; 60/345,641; 60/404,919; 60/436,359; 60/464,532; U.S. Ser. Nos. 10/270,071; 10/270,073; 10/328,190; PCT/U502/32717; PCT/US02/32718; and PCT/US02/38985.

The invention is further described by reference to the following examples, which are provided for illustration only. The invention is not limited to the examples but rather includes all variations that are evident from the teachings provided herein. All citations made to published articles, as well as to patents and patent applications, are incorporated herein in their entirety.

EXAMPLES

Example 1

Molecular Cloning and Sequence Elucidation for MN3 Heavy and Light Chain Variable Regions The VH and Vκ genes of MN3 were obtained by RT-PCR as described by Orlandi et al. (PNAS 86:3833-3837 (1989) and Leung et al. (Hybridoma 13:469-476 (1994). Multiple independent clones were sequenced to eliminate possible errors resulted from PCR reaction. The coding sequences for murine VH and Vκ were found in the cloned PCR products and designated as MN3Vκ (FIG. 1A) and MN3VH (FIG. 1B), respectively. To confirm the authenticity of V genes for MN3, a chimeric MN3 antibody was constructed and expressed in Sp2/0 cell. The cloned Vκ and VH fragments were first subcloned into the respective staging vectors, VKpBR and VHpBS (FIGS. 2A and 2B). The 650 bp fragment containing the Vκ, along with the promoter and signal peptide sequences, were then excised from the VKpBR staging vector by HindIII and BamHI restriction endonucleases digestion and subcloned into pKh, which is a pSVhyg-based expression vector containing the genomic sequence of the human kappa constant region, an Ig enhancer, a kappa enhancer and the hyg-resistant gene, resulting in the final expression vector for the light chain of cMN3. Similarly, the about 850 bp VH fragments was subcloned into pG1g, a pSVgpt-based expression vector carrying the genomic sequence of the human IgG1 constant region, an Ig enhancer and the xanthine-guanine phosphoribosyl transferase (gpt) gene, resulting in the final expression vector for the heavy chain of cMN3. The two expression vectors were co-transfected into Sp2/0-Ag14 cells by electroporation and selected for hygromycin resistance. Stable transfectoma clones were expanded and confirmed to produce chimeric antibodies by ELISA assay (Example 3). The antigen binding specificity and affinity of purified cMN3 were evaluated by a competitive binding ELISA assay. Briefly, varying concentrations of cMN3 or mMN3 were mixed with a constant amount of biotinylated murine MN3 and incubated in 96-well ELISA plate coated with CEA. The residual binding of the biotinylated MN3 was measured by HRP-conjugated streptavidin and a substrate solution containing ortho-phenylenediamine dihydrochloride and $H_2O_2$. As shown in FIG. 3, cMN3 competed with with radiolabeled HRP-conjugated MN3 for antigen binding and the binding activity of cMN3 is comparable with that of MN3.

Example 2

Choice of Human Frameworks and Sequence Design for hMN3

The light and heavy chain variable region sequences encoding the humanized MN3 antibody (hMN3) were designed and constructed. By comparing the murine MN3 V region FR sequences to that of human Abs in the Kabat database (Sequences of Proteins of Immunological Interest (Bethesda, Md.: U.S. Department of Health and Human Services, Public Health Service, National Institute of Health, 1991), the FRs of human REI and EU VH were found to exhibit the highest degree of sequence homology to that of MN3Vκ and MN3VH, respectively (FIG. 4). One exception is the FR4 of MN3VH, which showed the highest sequence homology with that of KOL VH (FIG. 4B). Thus, the human REI framework sequences was used for Vκ, and a combination of EU (FR1-3) and KOL (FR4) for VH as shown in FIGS. 4A and 4B, respectively. A variable number of murine amino acid residues in each chain outside of the CDR regions were maintained in the humanized design when compared to the starting human antibody frameworks. The light chain of hMN3 contains six amino acid changes from the REI framework: T20S, T22S, T39K, S60D, Y71F, and Q100G (FIG. 4A). The heavy chain of hMN3 also contains six changes from the human EU frameworks: G27Y, S30R, V67F, T68A, I69F, and G94R, (FIG. 4B).

Example 3

Method of hMN3 Construction

Each humanized variable chain was constructed in two parts, a 5'- and a 3'-half, designated as "A" and "B", respectively. Each half was produced by PCR amplification of a single stranded long synthetic oligonucleotide template with two short flanking primers using Taq polymerase. The amplified fragments were first cloned into the pCR4 TA cloning vector from Invitrogen and subjected to DNA sequencing. The templates and primer pairs are listed as follows:

| Template | Primers | Product |
|---|---|---|
| Oligo G | Oligo 13/Oligo 14 | VHA |
| Oligo H | Oligo 15/Oligo 16 | VHB |
| Oligo I | Oligo 17/Oligo 18 | VKA |
| Oligo J | Oligo 19/Oligo 20 | VKB |

The sequence information for the above identified oligonucleotides is as follows:

```
Oligo G (represents the minus strand of hMN3VH
domain complementary to nt 25-173, 149 bp)
(SEQ ID NO: 38)
5'-GGCTCACCGG TGTAGGTGTT TATCCAGCCC ATCCACTCTA

AACCCTGTCC TGGAGCCTGT CTCACCCAGT TCATTCCATA

GTTTCTGAAG GTATACCCAG AAGCCTTGCA GGAGACCTTG

ACGCTAGATC CAGGCTTCTT GACCTCAGC-3'

Oligo H (represents the minus strand of hMN3VH
domain complementary to nt 181-329, 149 bp)
(SEQ ID NO: 39)
5'-TCGAGGCTAC TACCGTTGAA ATCCATCCAT CCCTTTCTTG

CACAGAAATA GAAAGCCGTG TCCTCAGATC TCAAGCTAGA

CAGCTCCATA TAGGCAGTGT TGGTAGATTC GTCGGCTGTG

AAGGCAAACC GTCCCTTGAA GTCATCAGC-3'

Oligo 13 (SEQ ID NO: 40)
5'-CCAACTGCAG CAGTCTGGAG CTGAGGTCAA GAAGCCT-3'

Oligo 14 (SEQ ID NO: 41)
5'-GGCTCACCGG TGTAGGTGTT-3'

Oligo 15 (SEQ ID NO: 42)
5'-ACCTACACCG GTGAGCCAAC ATATGCTGAT GACTTCAAGG

GACG-3'

Oligo 16 (SEQ ID NO: 43)
5'-GGTGACCGGG GTCCCTTGGC CCCAGTAGTC GAGGCTACTA

CCGTTGA-3'

Oligo I (represents the minus strand of hMN3Vk
domain complementary to nt 31-170, 140 bp)
(SEQ ID NO: 44)
5'-GAAACTTTGT AGATCAGCAG CTTTGGAGCC TTACCTGGCT

TCTGCTGGTA CCATTCTAAA TAGGTGTTTC CATTACTATG

TACAATGCTC TGACTGGATC TACAAGAGAT GGACACTCTG

TCACCCACGC TGGCGCTCAG-3'

Oligo J (represents the minus strand of hMN3VH
domain complementary to nt 191-321, 131 bp)
(SEQ ID NO: 45)
5'-GGTCCCGCCG CCGAACGTCG GAGGAACATG TGAACCTTGA

AAGCAGTAGT AGGTGGCGAT GTCCTCTGGC TGGAGGCTGC

TGATGGTGAA GGTGAAGTCG GTACCGCTAC CGCTACCGCT

GAATCTGTCT G-3'

Oligo 17 (SEQ ID NO: 46)
5'-CAGCTGACCC AGAGCCCAAG CAGCCTGAGC GCCAGCGTGG

G-3'
```

-continued

```
Oligo 18 (SEQ ID NO: 47)
5'-CTGGCACTCC GGAAAATCGG TTGGAAACTT TGTAGATCAG

CAG-3'

Oligo 19 (SEQ ID NO: 48)
5'-CAACCGATTT TCCGGAGTGC CAGACAGATT CAGCGGT-3'

Oligo 20 (SEQ ID NO: 49)
5'-GATCTCCACC TTGGTCCCGC CGCCGAACGT CGG-3'
```

1. Light Chain

Unique restriction sites were included at the ends of each fragment to facilitate joining through DNA ligation. The amplified VKA fragment contained a PvuII restriction site, CAGCTG, at its 5'-end and a BspEI restriction site, TCCGGA, at the 3'-end. The amplified VKB fragment contained a BspEI restriction site at its 5'-end and a BglII restriction site, AGATCT, at the 3'-end. Assembly of the full-length Vκ chain was accomplished by restriction enzyme digestion of each fragment with the appropriate 5'- and 3'-enzymes and ligation into the VKpBR2 vector previously digested with PvuII and BclI (BclI digested end is compatible with that of BglII). The resulting ligated product contains the A fragment ligated to the PvuII site, the B fragment ligated to the BclI site, and the A and B fragments joined together at the BstBI site (FIG. 5A). Upon confirmation of a correct open reading frame by DNA sequencing, the intact chain was removed from VKpBR2 as a XbaI to BamHI fragment and ligated into the pdHL2 expression vector. The vector containing only Vκ sequence was designated as hMN3VkpdHL2.

2. Heavy Chain

The same construction method as done for Vκ was carried out VH with the following modifications. The 5'-end restriction site of the A fragments was Pstl (CTGCAG) and the 3'-end restriction site of B fragments was BstEll (GGTCACC). These fragments were joined together upon ligation into the VHpBS2 vector at a common Agel site (ACCGGT), resulting in full-length VH sequences (FIG. 5B), which were confirmed by DNA sequencing. The assembled VH genes were subcloned as XhoI-BamHI restriction fragments into the expression vector containing the VK sequence, hMN3VkpdHL2, predigested with XhoI and HindIII. To ligate the BamHI end of the VH fragment to the HindIII end of the vector, a linker, designated as HNB was used. The resulting expression vectors were designated as hMN3pdHL2.

```
HNB linker
5'-AGCTTGCGGCCGC-3' (SEQ ID NO: 50)

3'-ACGCCGGCGCTAG-5' (SEQ ID NO: 51)
```

Example 4

Transfection and Expression of hMN3 Antibodies

The procedure employed to express hMN3 using pdHL2 based vecto in Sp2/0 cells by transfection was the same as described by Qu et al. Clin. Cancer Res. 5:3095s-3100s (1999). Briefly, 30 ug of hMN3pdHL2 were linearized by digestion with SalI and transfected into Sp2/0-Ag14 cells by electroporation (450V and 25 uF). The transfected cells were plated into 96-well plate for 2 days and then selected for MTX resistance. Supernatants from colonies surviving selection were monitored for human antibody secretion by ELISA assay. Positive cell clones were expanded and hMN3 was purified from cell culture supernatant by affinity chromatography on a Protein A column.

Example 5

Binding Activity Assays

Figure 6:
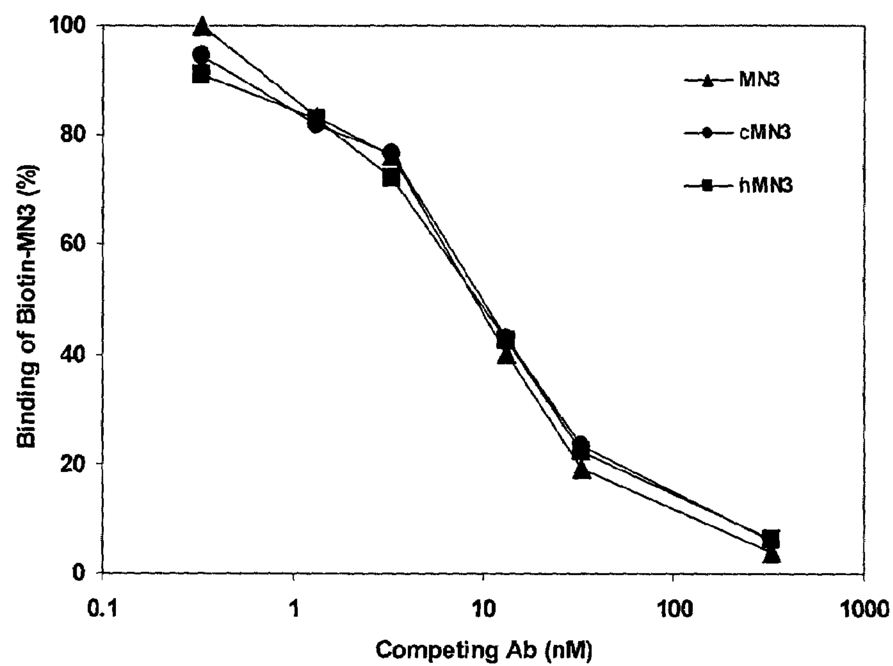
FIG. 6 shows the results of a competitive ELISA assay to compare the binding activity of MN3, cMN3 and hMN3. Varying concentrations of cMN3 (closed circles), hMN3 (closed squares) or mMN3 (closed triangles) were mixed with a constant amount of biotinylated murine MN3 and incubated in microplate wells coated with CEA. The residual binding of the biotinylated MN3 was measured by HRP-conjugated streptavidin and substrate. The results indicated that cMN3 and hMN3 and the murine MN3 antibody, MN3 competed equally well for the binding of antigen.

A competition ELISA binding assay was carried out to assess the immunoreactivity of hMN3 relative to the parent MN3, and cMN3. 96-well microtitration plate was coated with CEA. Varying concentrations of MN3, cMN3 or hMN3 (0.01-100 ug/ml) was made to compete with a constant amount of biotinylated murine MN3 (0.5 ug/ml) for binding to CEA, and the residual binding of the biotinylated MN3 in the presence of the competing antibodies was measured. As shown in FIG. 6, hMN3 exhibited comparable binding activity as that of murine MN3 and cMN3.

Example 6

Therapy of Acute Myeloid Leukemia

A 71-year-old man with a history of acute myeloid leukemia relapses following 2 courses of chemotherapy, and presents with a high number of immature, granulocytic leukemia cells in his blood and marrow, and also with an enlarged spleen, anemia, malaise, lethargy, diffuse bone pain, and some increased bruising and bleeding. He is first given a 100 mCi dose of I-131 conjugated to the humanized MN3 antibody (50 mg of antibody given as part of the dose). Peripheral blood counts 4 weeks later indicate a fall in myeloid leukemic cells by 60% and an improvement in his splenomegaly. He is then given, 2 weeks later, 4 weekly doses of naked, humanized MN3 antibody in 3-hr i.v. infusions, each dose being 450 mg of the antibody. This cycle of 4 doses is then repeated 3 months later. His myeloid leukemia cells in the blood are not reduced by another 30% from the last measurement, and a bone marrow biopsy shows, in contrast to the pre-treatment biopsy, a marked reduction in infiltration with leukemic cells. The patient's other signs and symptoms improve over the next 2 months.

The present methods can involve any or all of the steps or conditions discussed above in various combinations, as desired. Accordingly, it will be readily apparent to the skilled artisan that in some of the disclosed methods certain steps can be deleted or additional steps performed without affecting the viability of the methods.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," "more than" and the like include the number recited and refer to ranges which can be subsequently broken down into subranges as discussed above. In the same manner, all ratios disclosed herein also include all subratios falling within the broader ratio.

One skilled in the art will also readily recognize that where members are grouped together in a common manner, such as in a Markush group, the present invention encompasses not only the entire group listed as a whole, but each member of the group individually and all possible subgroups of the main group. Accordingly, for all purposes, the present invention encompasses not only the main group, but also the main group absent one or more of the group members. The present invention also envisages the explicit exclusion of one or more of any of the group members in the claimed invention.

All references disclosed herein are specifically incorporated by reference thereto. Unless otherwise specified, "a" or "an" means "one or more". While preferred embodiments have been illustrated and described, it should be understood that changes and modifications can be made therein in accordance with ordinary skill in the art without departing from the invention in its broader aspects as defined in the claims.

What is claimed is:

1. A chimeric or humanized MN-3 antibody or fragment thereof that binds NCA90 comprising the MN-3 light chain CDR sequences CDR1 (RSSQSIVHSNGNTYLE, SEQ ID NO:1), CDR2 (KVSNRFS, SEQ ID NO:2) and CDR3 (FQGSHVPPT, SEQ ID NO:3) and the MN-3 heavy chain CDR sequences CDR1 (NYGMN, SEQ ID NO:4), CDR2 (WINTYTGEPTYADDFKG, SEQ ID NO:5) and CDR3 (KGWMDFNSSLDY, SEQ ID NO:6).

2. The humanized antibody or fragment thereof of claim 1, wherein the antibody or fragment comprises the framework (FR) region sequences of the light and heavy chain variable regions of a human antibody and at least one light and heavy chain constant regions of a human antibody.

3. The humanized antibody or fragment thereof of claim 2, wherein at least one of the FRs of the light and heavy chain variable regions of the humanized MN-3 antibody or fragment thereof comprises at least one amino acid substituted with the corresponding amino acid of the murine MN-3 antibody.

4. The humanized antibody or fragment thereof of claim 3, wherein the at least one amino acid from the murine MN-3 antibody is selected from the group consisting of amino acid residue 27, 30, 67, 68, 69 and 94 of the murine MN-3 heavy chain variable region sequence (SEQ ID No. 11) or amino acid residue 20, 22, 39, 60, 70 and 100 of the murine MN-3 light chain variable region sequence (SEQ ID No. 9).

5. The chimeric antibody or fragment thereof of claim 1, wherein the antibody or fragment thereof comprises the amino acid sequences of cMN-3VK (SEQ ID NO:13) and cMN-3VH (SEQ ID NO:15).

6. The humanized antibody or fragment thereof of claim 2, wherein the antibody or fragment thereof comprises the amino acid sequences of hMN-3VK (SEQ ID NO:18) and hMN-3VH (SEQ ID NO:21).

7. The chimeric or humanized antibody or fragment thereof claim 1, wherein the fragment is selected from the group consisting of Fv, $F(ab')_2$, Fab' and Fab.

8. The chimeric or humanized antibody or fragment thereof of claim 1, wherein the antibody or fragment is bound to at least one diagnostic/detection agent or at least one therapeutic agent or is part of a fusion protein.

9. The chimeric or humanized antibody or fragment thereof of claim 8, wherein the diagnostic/detection agent comprises a photoactive diagnostic/detection agent, a chromagen or dye, a radionuclide with an energy between 20 and 10,000 keV, a gamma-, beta- or a positron-emitting isotope, a contrast agent, a paramagnetic ion, an ultrasound-enhancing agent, a liposome or a radiopaque compound.

10. The chimeric or humanized antibody or fragment thereof of claim 8, wherein the therapeutic agent is selected from the group consisting of a radionuclide, boron, gadolinium or uranium atoms, an immunomodulator, a cytokine, a hormone, a hormone antagonist, an enzyme, an enzyme inhibitor, a photoactive therapeutic agent, a cytotoxic drug, a toxin, an angiogenesis inhibitor, a different antibody and a combination thereof.

11. The chimeric or humanized antibody or fragment thereof of claim 10, wherein the drug is selected from the group consisting of antimitotic, alkylating, antimetabolite, angiogenesis-inhibiting, apoptotic, alkaloid, COX-2-inhibiting and antibiotic agents and combinations thereof.

12. The chimeric or humanized antibody or fragment thereof of claim 10, wherein the drug is selected from the group consisting of nitrogen mustards, ethylenimine derivatives, alkyl sulfonates, nitrosoureas, triazenes, folic acid analogs, anthracyclines, taxanes, COX-2 inhibitors, pyrimidine analogs, purine analogs, antibiotics, enzymes, epipodophyllotoxins, platinum coordination complexes, vinca alkaloids, substituted ureas, methyl hydrazine derivatives, adrenocortical suppressants, hormone antagonists, enzyme inhibitors, endostatin, taxols and other taxanes, camptothecins, doxorubicin, and a combination thereof.

13. The chimeric or humanized antibody or fragment thereof of claim 10, wherein the toxin is selected from the group consisting of ricin, abrin, alpha toxin, saporin, ribonuclease (RNase), DNase I, *Staphylococcal* enterotoxin-A, pokeweed antiviral protein, gelonin, diphtheria toxin, *Pseudomonas* exotoxin, and *Pseudomonas* endotoxin.

14. The chimeric or humanized antibody or fragment thereof of claim 10, wherein the immunomodulator is selected from the group consisting of a cytokine, a stem cell growth factor, a lymphotoxin, a hematopoietic factor, a colony stimulating factor (CSF), an interferon (IFN), a stem cell growth factor, erythropoietin, thrombopoietin, an antibody and a combination thereof.

15. The chimeric or humanized antibody or fragment thereof of claim 14, wherein the lymphotoxin is tumor necrosis factor (TNF), the hematopoietic factor is an interleukin (IL), the colony stimulating factor is granulocyte-colony stimulating factor (G-CSF) or granulocyte macrophage-colony stimulating factor (GM-CSF), the interferon is interferons-α, -βor -γ, and the stem cell growth factor is designated "S1 factor".

16. The chimeric or humanized antibody or fragment thereof of claim 14, wherein the cytokine is selected from the group consisting of IL-1, IL-2, IL-3, IL-6, IL-10, IL-12, IL-18, IL-21, interferon-γ, TNT-α and a combination thereof.

17. The chimeric or humanized antibody or fragment thereof of claim 10, wherein the radionuclide is selected from the group consisting of P-32, P-33, Sc-47, Fe-59, Cu-64, Cu-67, Se-75, As-77, Sr-89, Y-90, Mo-99, Rh-105, Pd-109, Ag-111, I-125, I-131, Pr-142, Pr-143, Pm-149, Sm-153, Th-161, Ho-166, Er-169, Lu-177, Re-186, Re-188, Re-189, Ir-194, Au-198, Au-199, Pb-211, Pb-212, Bi-213, Co-58, Ga-67, Br-80m, Tc-99m, Rh-103m, Pt-109, In-111, Sb-119, Ho-161, Os-189m, Ir-192, Dy-152, At-211, Bi-212, Ra-223, Rn-219, Po-215, Bi-211, Ac-225, Fr-221, At-217, Fm-255 and combinations thereof.

18. An antibody fusion protein comprising a first humanized or chimeric antibody or fragment according to claim 1, attached to a second antibody or fragment.

19. The antibody fusion protein of claim 18, wherein the second antibody or fragment is a humanized or chimeric antibody or fragment.

20. The antibody fusion protein of claim 18, wherein the second antibody or fragment binds to an antigen other than NCA90.

21. The antibody fusion protein of claim 19, further comprising a diagnostic/detection or therapeutic agent conjugated to the fusion protein.

22. The antibody fusion protein of claim 20, wherein the second antibody or fragment binds to a granulocyte-associated antigen.

23. A kit useful for treating or identifying diseased tissues in a subject comprising: (A) a bi-specific antibody or antibody fragment having at least one arm that specifically binds a targeted tissue and at least one other arm that specifically binds a targetable conjugate, wherein the one arm that specifically binds a targeted tissue is a humanized or chimeric antibody or fragment thereof according to claim 1; (B) a first targetable conjugate which comprises a carrier portion which comprises or bears at least one epitope recognizable by the at least one other arm of the bi-specific antibody or antibody fragment, and one or more conjugated therapeutic or diagnostic agents; and (C) optionally, a clearing composition useful for clearing non-localized antibodies and antibody fragments; and (D) optionally, when the therapeutic agent conjugated to the first targetable conjugate is an enzyme, (i) a prodrug, when the enzyme is capable of converting the prodrug to a drug at the target site; or (ii) a drug which is capable of being detoxified in the subject to form an intermediate of lower toxicity, when the enzyme is capable of reconverting the detoxified intermediate to a toxic form, and, therefore, of increasing the toxicity of the drug at the target site, or (iii) a prodrug which is activated in the subject through natural processes and is subject to detoxification by conversion to an intermediate of lower toxicity, when the enzyme is capable of reconverting the detoxified intermediate to a toxic form, and, therefore, of increasing the toxicity of the drug at the target site, or (iv) a second targetable conjugate which comprises a carrier portion which comprises or bears at least one epitope recognizable by the at least one other arm of the bi-specific antibody or antibody fragment, and a prodrug, when the enzyme is capable of converting the prodrug to a drug at the target site.

24. The kit of claim 23, wherein the targetable conjugate is selected from the group consisting of (i) DOTA-Phe-Lys (HSG)-D-Tyr-Lys(HSG)-NH2; (ii) DOTA-Phe-Lys(HSG)-Tyr-Lys(HSG)-NH2 (SEQ ID NO: 7); (iii) Ac-Lys(HSG)D-Tyr-Lys(HSG)-Lys(Tscg-Cys)-NH2; (iv) DOTA-D-Asp-D-Lys(HSG)-D-Asp-D-Lys(HSG)-NH2; (v) DOTA-D-Glu-D-Lys(HSG)-D-Glu-D-Lys(HSG)-NH2; (vi) DOTA-D-Tyr-D-Lys(HSG)-D-Glu-D-Lys(HSG)-NH2; (vii) DOTA-D-Ala-D-Lys(HSG)-D-Glu-D-Lys(HSG)-NH2; (viii) DOTA-D-Phe-D-Lys(HSG)-D-Tyr-D-Lys(HSG)-NH2; (ix) Ac-D-Phe-D-Lys(DOTA)-D-Tyr-D-Lys(DOTA)- NH2; (x) Ac-D-Phe-D-Lys(DTPA)-D-Tyr-D-Lys(DTPA)-NH2; (xi) Ac-D-Phe-D-Lys(Bz-DTPA)-D-Tyr-D-Lys(Bz-DTPA)-NH2; (xii) Ac-D-Lys(HSG)-D-Tyr-D-Lys(HSG)-D-Lys(Tscg-Cys)-NH2; (xiii) DOTA-D-Phe-D-Lys(HSG)-D-Tyr-D-Lys(HSG)-D-Lys(Tscg-Cys)-NH2; (xiv) (Tscg-Cys)-D-Phe-D-Lys(HSG)-D-Tyr-D-Lys(HSG)-D-Lys(DOTA)-NH2; (xv) Tscg-D-Cys-D-Glu-D-Lys(HSG)-D-Glu-D-Lys(HSG)-NH2; (xvi) (Tscg-Cys)-D-Glu-D-Lys(HSG)-D-Glu-D-Lys(HSG)-NH2; (xvii) Ac-D-Cys-D-Lys(DOTA)-D-Tyr-D-Ala-D-Lys(DOTA)-D-Cys-NH2; (xviii) Ac-D-Cys-D-Lys(DTPA)-D-Tyr-D-Lys (DTPA)-NH2; (xix) Ac-D-Lys(DTPA)-D-Tyr-D-Lys (DTPA)-D-Lys(TscG-Cys)-NH2; (xx) Ac-D-Lys(DOTA)-D-Tyr-D-Lys(DOTA)-D-Lys(TscG-Cys)-NH2;

(xxi)

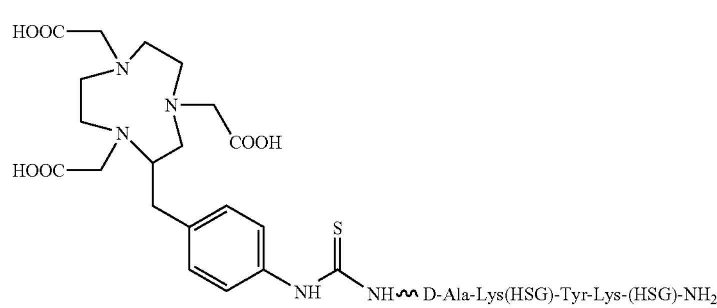

-continued
(xxii)
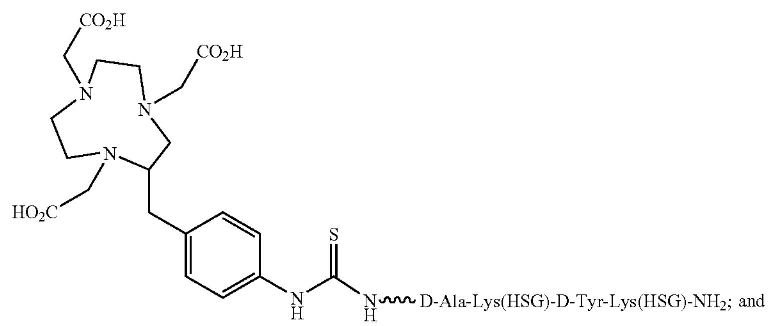
(xxii)
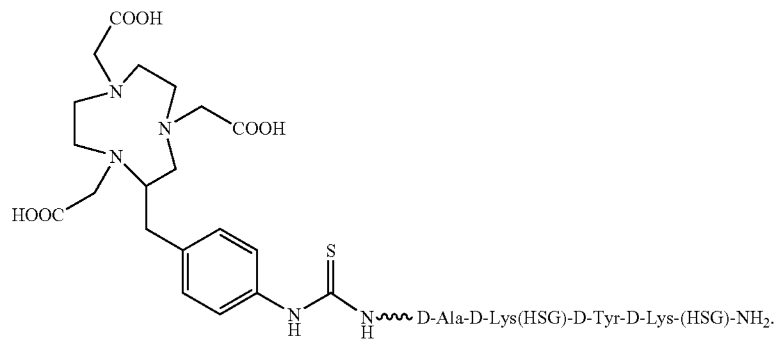
* * * * *